U S007604947B2

(12) United States Patent
Gudas

(10) Patent No.: US 7,604,947 B2
(45) Date of Patent: Oct. 20, 2009

(54) DETECTION AND MODULATION OF CANCER STEM CELLS

(75) Inventor: Lorraine J. Gudas, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 107 days.

(21) Appl. No.: 11/148,149

(22) Filed: Jun. 8, 2005

(65) Prior Publication Data

US 2005/0277162 A1    Dec. 15, 2005

Related U.S. Application Data

(60) Provisional application No. 60/578,461, filed on Jun. 9, 2004.

(51) Int. Cl.
*G01N 33/53* (2006.01)
*C07K 16/00* (2006.01)
(52) U.S. Cl. .................. 435/7.1; 530/387.1; 530/387.7
(58) Field of Classification Search ....................... None
See application file for complete search history.

(56) References Cited

U.S. PATENT DOCUMENTS

| | | | |
|---|---|---|---|
| 4,036,945 A | 7/1977 | Haber | |
| 4,331,647 A | 5/1982 | Goldenberg | |
| 4,376,110 A | 3/1983 | David et al. | |
| 4,411,990 A | 10/1983 | Salmon et al. | |
| 4,683,195 A | 7/1987 | Mullis et al. | |
| 4,683,202 A | 7/1987 | Mullis | |
| 4,816,567 A | 3/1989 | Cabilly et al. | |
| 4,946,778 A | 8/1990 | Ladner et al. | |
| 4,965,188 A | 10/1990 | Mullis et al. | |
| 5,641,673 A | 6/1997 | Haseloff et al. | |
| 5,733,743 A | 3/1998 | Johnson et al. | |
| 5,750,373 A | 5/1998 | Garrard et al. | |
| 6,290,957 B1 | 9/2001 | Lowman et al. | |
| 2002/0019517 A1 | 2/2002 | Koide | |
| 2005/0118582 A1* | 6/2005 | Swarnakar et al. ............. | 435/6 |

FOREIGN PATENT DOCUMENTS

| | | |
|---|---|---|
| EP | 0321201 A2 | 6/1989 |
| EP | 0404097 A2 | 12/1990 |
| WO | WO-93/11161 A1 | 6/1993 |

OTHER PUBLICATIONS

Mongan, N.P., Martin, K.M., and Gudas, L.J. The putative human stem cells marker, Rex-1 (Zfp42): structural classification and expression in normal human epithelial and carcinoma cell cultures. 2006. Molecular Carcinogenesis, vol. 45, pp. 887-900.*
Lederman, De Martino, Daugherty, Foeldvari, Yellin, Cleary, Berkowitz, Lowy, Braunstein, Mark, and Chess. A single amino acid substitution in a common African allele of the CD4 molecule ablates binding of the monoclonal antibody OKT4. Molecular Immunology, 1991. vol. 28, pp. 1171-1181.*

Li, Yamashiro, Tseng, Chang and Ferrara. B-endorphin omission analogs: dissociation of immunoreactivity from other biological activities. Proceedings of the National Academy of Sciences, 1980. vol. 77, pp. 3211-3214.*
"TreeView—Tree Drawing Software for Apple Macintosh and Windows", http://web.archive.org/web/20040606025208/taxonomy.zoology.gla.ac.uk/rod/treeview.html, (archived Jun. 6, 2004), 2 pgs.
Abeyta, M. J., et al., "Unique Gene Expression Signatures of Independently-Derived Human Embryonic Stem Cell Lines", *Human Molecular Genetics*,13(6), (2004), 601-608.
Akashi, K., et al., "A Clonogenic Common Myeloid Piogenitor That Gives Rise to All Myeloid Lineages", *Nature*, 404, (Mar. 9, 2000), 193-197.
Al-Hajj, M., et al., "Prospective Identification of Tumorigenic Breast Cancer Cells", *Proc. Natl. Acad. Sci. USA*, 100(7), (Apr. 1, 2003), 3983-3988.
Al-Hajj, M., et al., "Self-Renewal and Solid Tumor Stem Cells", *Oncogene*, 23, (2004), 7274-7282.
Altschul, S. F., "Basic Local Alignment Search Tool", *J. Mol. Biol.*, 215(3), (Oct. 5, 1990), 403-410.
Altschul, S. F., "Gapped BLAST and PSI-BLAST: A New Generation of Protein Database Search Programs", *Nucleic Acids Research*, 25(17), (1997),3389-3402.
Alzari, P. M., "Three-Dimensional Structure of Antibodies", *Annual Review of Immunology*, 6, (1988), 555-580.
Beachy, P. A., et al., "Tissue Repair and Stem Cell Renewal in Carcinogenesis", *Nature*, 432, (Nov. 18, 2004), 324-331.
Ben-Shushan, E., et al., "*Rex-1*, a Gene Encoding a Transcription Factor Expressed in the Early Embryo, is Regulated via Oct-3/4 and Oct-6 Binding to an Octamer Site and a Novel Protein, Rox-1, Binding to an Adjacent Site", *Molecular & Cellular Biology*, 18(4), (Apr. 1998), 1866-1878.
Bergsagel, D. E., et al., "Growth Characteristics of a Mouse Plasma Cell Tumor", *Cancer Research*, 28(11), (Nov. 1968), 2187-2195.
Bhatt, R. I., et al., "Novel Method for the Isolation and Characterisation of the Putative Prostatic Stem Cell", *Cytometry Part A*, 54A(2), (2003), 83-99.
Bird, R. E., "Single-Chain Antigen-Binding Proteins", *Science*, 242(4877), (Oct. 21, 1988), 423-426.
Bonnet, D., et al., "Human Acute Myeloid Leukemia is Organized as a Hierarchy That Originates From a Primitive Hematopoietic Cell", *Nature Medicine*, 3(7), (Jul. 1997), 730-737.
Boorjian, S. , et al., "Reduced Lecithin: Retinol Acyltransferase Expression Correlates With Increased Pathologic Tumor Stage in Bladder Cancer", *Clinical Cancer Research*, 10, (May 15, 2004), 3429-3437.

(Continued)

*Primary Examiner*—David J. Blanchard
*Assistant Examiner*—Anne M. Gussow
(74) *Attorney, Agent, or Firm*—Schwegman, Lundberg and Woessner, P.A.

(57) ABSTRACT

The invention relates to method for detecting and modulating the expression and activity of REX-1. As described herein, REX-1 is expressed in certain cancer cells, including cancer stem cells. The invention also provides methods for detecting and/or treating cancer.

4 Claims, 12 Drawing Sheets
(6 of 12 Drawing Sheet(s) Filed in Color)

Bork, P., "Proposed Acquisition of an Animal Protein Domain by Bacteria", *Proc. Natl. Acad.Sci.USA*, 89(19), (Oct. 1992), 8990-8994.

Bork, P., "The Immunoglobulin Fold. Structural Classification, Sequence Patterns and Common Core", *Journal of Molecular Biology*, 242(4), (1994), 309-320.

Brivanlou, A. H., et al., "Setting Standards for Human Embryonic Stem Cells", *Science*, 300, (May 9, 2003), 913-916.

Brown, J. L., et al., "The *Drosophila* Polycomb Group Gene *pleiohomeotic* Encodes a DNA Binding Protein with Homology to the Transcription Factor YY1", *Molecular Cell*, 1. (Jun. 1998), 1057-1064.

Bruce, W. R., et al., "A Quantitative Assay for the Number of Murine Lymphoma Cells Capable of Proliferation in vivo", *Nature*, 199(4888), (Jul. 6, 1963), 79-80.

Campbell, I. C., "Building Proteins With Fibronectin Type III Modules", *Structure*, 2(5), (May 15, 1994), 333-337.

Cech, T. R., "Ribozyme Engineering", *Current Opinion in Structural Biology*, 2(4), (Aug. 1992), 605-609.

Cech, T. R., "Self-Splicing of Group I Introns", *Annual Review of Biochemistry*, 59, (1990), 543-568.

Cech, T. R., "The Chemistry of Self-Splicing RNA and RNA Enzymes", *Science*, 236(4808), (1987), 1532-1539.

Chan, R. W., et al., "Clonogenicity of Human Endometrial Epithelial and Stromal Cells", *Biology of Reproduction*, 70, (2004), 1738-1750.

Chang, E. N., et al., "Transplantation: Focus on Kidney, Liver and Islet Cells", *Canadian Journal of Surgery*, 47(2), (2004), 122-129.

Chen, A. C., et al., "An Analysis of Retinoic Acid-Induced Gene Expression and Metabolism in AB1 Embryonic Stem Cells", *The Journal of Biological Chemistry*, 271(25), (1996), 14971-14980.

Chenna, R., et al., "Multiple Sequence Alignment With the Clustal Series of Programs", *Nucleic Acid Research*, 31(13), (2003), 3497-3500.

Chiswell, D. J., "Phage Antibodies: Will New 'Coliclonal' Antibodies Replace Monoclonal Antibodies?", *Trends in Biotechnology*, 10. (1992), 80-84.

Clackson, T., "In vitro Selection From Protein and Peptide Libraries", *Trends in Biotechnology*, 12(5), (May 1994), 173-184.

Clackson, T/, "Making Antibody Fragments Using Phage Display Libraries", *Nature*, 352(6336), (Aug. 15, 1991), 624-628.

Clayton, H., et al., "Growth and Differentiation of Progenitor/Stem Cells Derived From the Human Mammary Gland", *Experimental Cell Research*. 297, (2004), 444-460.

Coles, B. L., et al., "Facile Isolation and the Characterization of Human Retinal Stem Cells", *Proc. Natl. Acad. Sci. USA*, 101(44), (Nov. 2, 2004), 15772-15777.

Cotsarelis, G., et al., "Epithelial Stem Cells in the Skin: Definition, Markers, Localization and Functions", *Experimental Dermatology*, 8(1), (Feb. 1999), 80-88.

Couture, L. A., "Anti-Gene Therapy: The Use of Ribozymes to Inhibit Gene Function", *Trends in Genetics*, 12(12), (1996), 510-515.

Cunningham, B. C., "Production of an Atrial Natriuretic Peptide Variant That is Specific for Type A Receptor", *The EMBO Journal*, 13(11). (1994), 2508-2515.

Cwirla, S. E., "Peptides on Phage: a Vast Library of Peptides for Identifying Ligands", *Proc. Natl. Acad. Sci. USA*, 87(16), (Aug. 1990), 6378-6382.

Dontu, G., et al., "In vitro Propagation and Transcriptional Profiling of Human Mammary Stem/Progenitor Cells", *Genes & Development*, 17, (2003),1253-1270.

Elbashir, S. M., "Duplexes of 21-Nucleotide RNAs Mediate RNA Interference in Cultured Mammalian Cells", *Nature*, 411, (2001), 494-498.

Fuchs, E., et al., "Stem Cells: A New Lease on Life", *Cell*, 100, (2000), 143-155.

Gage, F. H., "Mammalian Neural Stem Cells", *Science*, 287, (Feb. 25, 2000), 1433-1438.

Goldberg, J. S., et al., "Phase I Trial of Interferon α2b and Liposome-Encapsulated All-*Trans* Retinoic Acid in the Treatment of Patients With Advanced Renal Cell Carcinoma", *Cancer*, 95, (2002), 1220-1227.

Gudjonsson, T. , et al., "Isolation, Immortalization, and Characterization of a Human Breast Epithelial Cell Line With Stem Cell Properties", *Genes & Development*, 16, (2002), 693-706.

Guinan, P., et al., "TNM Staging of Renal Cell Carcinoma", *Cancer*, 80, (1997),992-993.

Gupta, S., et al., "A Role for Extrarenal Cells in the Regeneration Following Acute Renal Failure", *Kidney International*, 62, (2002), 1285-1290.

Hamburger, A. W., et al., "Primary Bioassay of Human Tumor Stem Cells", *Science*, 197(4302), (Jul. 29, 1977), 461-463.

Hammerman, M. R., "Treatment for End-Stage Renal Disease: An Organogenesis/Tissue Engineering Odyssey", *Transplant Immunology*, 12, (2004), 211-218.

Hanahan, D., "The Hallmarks of Cancer", *Cell*, 100, (2000), 57-70.

Hanes, J., "In vitro Selection and Evolution of Functional Proteins by Using Ribosome Display", *Proc. Natl. Acad. Sci. USA*, 94(10), (May 13, 1997), 4937-4942.

Harborth, J., "Sequence, Chemical, and Structural Variation of Small Interfering RNAs and Short Hairpin RNAs and the Effect on Mammalian Gene Silencing", *Antisense and Nucleic Acid Drug Development*, 13(2), (2003), 83-105.

Harpaz, Y., et al., "Many of the Immunoglobulin Superfamily Domains in Cell Adhesion Molecules and Surface Receptors Belong to a New Structural Set Which is Close to That Containing Variable Domains", *Journal of Microbiology*, 238, (1994), 528-539.

Haseloff, J., "Simple RNA Enzymes with New and Highly Specific Endoribonuclease Activities", *Nature*, 334, (1988), 585-591.

Hawkins, R. E., "Selection of Phage Antibodies by Binding Affinity—Mimicking Affinity Maturation.", *Journal of Molecular Biology*, 254, (1992), 889-896.

Henderson, J. K., et al., "Preimplantation Human Embryos and Embryonic Stem Cells Show Comparable Expression of Stage-Specific Embryonic Antigens", *Stem Cells*, 20(4), (2002), 329-337.

Hollinger, P., ""Diabodies": Small Bivalent and Bispecific Antibody Fragments.", *Proc. Natl. Acad. Sci. USA*, 90(14), (1993), 6444-6448.

Holmes, M. A., "Structural Consequences of Humanizing an Antibody.", *Journal of Immunolgy*, 158(5), (1997),2192-2201.

Hoogenboom, H. R., et al., "Building Antibodies From Their Genes", *Immunological Reviews*, 130, (Dec. 1992), 41-68.

Hosler, B. A., et al., "An Octamer Motif Contributes to the Expression of the Retinoic Acid-Regulated Zinc Finger Gene Rex-1 (*Zfp*-42) in F9 Teratocarcinoma Cells", *Molecular and Cellular Biology*, 13(5), (1993), 2919-2928.

Hosler, B. A., et al., "Expression of *REX-1*, a Gene Containing Zinc Finger Motifs, Is Rapidly Reduced by Retinoic Acid in F9 Teratocarcinoma Cells", *Molecular and Cellular Biology*. 9(12), (1989),5623-5629.

Houbaviy, H. B., et al., Cocrystal Structure of YY1 Bound to the Adeno-Associated Virus P5 Initiator', *Proc. Natl. Acad. Sci. USA*, 93, (1996),13577-13582.

Humes, H. D., et al., "Tubulogenesis From Isolated Single Cells of Adult Mammalian Kidney: Clonal Analysis With a Recombinant Retrovirus", *American Journal of Physiology—Renal Physiology*, 271, (1996), F42-F49.

Ito, T. , et al., "Bone Marrow Is a Reservoir of Repopulating Mesangial Cells During Glomerular Remodeling", *Journal of the American Society of Nephrology*, 12, (2001), 2625-2635.

Iuchi, S., "Three Classes of $C_2H_2$ Zinc Finger Proteins", *Cellular and Molecular Life Sciences*, 58, (2001), 625-635.

Jemal, A., et al., "Cancer Statistics, 2004", *CA: A Cancer Journal for Clinicians*, 54, (2004), 8-29.

Jiang, Y., et al., "Multipotent Progenitor Cells Can Be Isolated From Postnatal Murine Bone Marrow, Muscle, and Brain", *Experimental Hematology*, 30(8), (Aug. 2002), 896-904.

Jiang, Y., et al., "Pluripotency of Mesenchymal Stem Cells Derived From Adult Marrow", *Nature*, 418(6893), (Jul. 4, 2002), 41-49.

Jones, P. T., "Replacing the Complementarity-Determining Regions in a Human Antibody With Those From a Mouse", *Nature*, 321(6069), (May 29, 1986), 522-525.

Jones, E. Y., "The Immunoglobulin Superfamily", *Current Opinion in Structural Biology*, 3(6), (1993), 846-852.

Jordan, C. T., "Cancer Stem Cell Biology: From Leukemia to Solid Tumors", *Current Opinion in Cell Biology*, 16, (2004), 708-712.

Kale, S., et al., "Bone Marrow Stem Cells Contribute to Repair of the Ischemically Injured Renal Tubule", *The Journal of Clinical Investigation*, 112(1), (2003), 42-49.

Kays, S. E., et al., "Regeneration of Renal Proximal Tubule Cells in Primary Culture Following Toxicant Injury: Response to Growth Factors", *Toxicology and Applied Pharmacology*, 132, (1995), 273-280.

Knight, R. D., et al., "Identification of Conserved C2H2 Zinc-Finger Gene Families in the Bilateria", *Genome Biology*, 2(5), (2001) ,0016.1-0016.8.

Koh, C. J., et al., "Tissue Engineering, Stem Cells, and Cloning: Opportunities for Regenerative Medicine", *Journal of the American Society of Nephrology*, 15, (2004), 1113-1125.

Kohler, G., "Continuous Cultures of Fused Cells Secreting Antibody of Predefined Specificity", *Nature*, 256(5517), (Aug. 7, 1975), 495-497.

Krause, D. S., "Multi-Organ, Multi-Lineage Engraftment by a Single Bone Marrow-Derived Stem Cell", *Cell*, 105, (May 2001), 369-377.

Lagasse, E., et al., "Toward Regenerative Medicine", *Immunity*, 14, (2001), 425-436.

Lane, M. A., et al., "Removal of LIF (Leukemia Inhibitory Factor) Results in Increased Vitamin A (Retinol) Metabolism to 4-Oxoretinal in Embryonic Stem Cells", *Proc. Natl. Acad. Sci. USA*, 96(23), (Nov. 9, 1999), 13524-13529.

Larrick, J. W., "PCR Amplification of Antibody Genes", *Methods: A Companion to Methods in Enzymology*, 2(2), (1991), 106-110.

Lin, F., et al., "Hematopoietic Stem Cells Contribute to the Regeneration of Renal Tubules After Renal Ischemia-Reperfusion Injury in Mice", *Journal of the American Society of Nephrology*, 14, (2003), 1188-1199.

Linehan, W. M., et al., "The Genetic Basis of Cancer of the Kidney", *The Journal of Urology*, 170, (2003), 2163-2172.

Lowman, H. B., "Selecting High-Affinity Binding Proteins by Monovalent Phage Display", *Biochemistry*, 30(45), (Nov. 12, 1991), 10832-10838.

Maeshima, A., et al., "Identification of Renal Progenitor-Like Tubular Cells that Participate in the Regeneration Processes of the Kidney", *Journal of the American Society of Nephrology*, 14, (2003), 3138-3146.

Marks, J. D., "By-passing Immunization. Human Antibodies From V-Gene Libraries Displayed on Phage", *Journal of Molecular Biology*. 222(3), (1991), 581-597.

Marshman, E., et al., "The Intestinal Epithelial Stem Cell", *BioEssays*, 24, (2002), 91-98.

McConnell, S. J., et al., "Tendamistat as a Scaffold for Conformationally Constrained Phage Peptide Libraries", *Journal of Molecular Biology*, 250(4), (Jul. 21, 1995), 460-470.

Mongan, N. P., et al., "Novel α7-like Nicotinic Acetylcholine Receptor Subunits in the Nematode *Caenorhabditis elegans*", *Protein Science*, 11, (2002), 1162-1171.

Morigi, M., et al., "Mesenchymal Stem Cells Are Renotropic, Helping to Repair the Kidney and Improve Function in Acute Renal Failure", *Journal of the American Society of Nephrology*, 15, (2004), 1794-1804.

Morrison, S. L., "Chimeric Human Antibody Molecules: Mouse Antigen-Binding Domains With Human Constant Region Domains", *Proc. Natl. Acad. Sci. USA*, 81(21), (Nov. 1984), 6851-6855.

Okamoto, K., et al., "A Novel Octamer Binding Transcription Factor is Differentially Expressed in Mouse Embryonic Cells", *Cell*. 60(3), (1990), 461-472.

Oliver, J. A., et al., "The Renal Papilla is a Niche for Adult Kidney Stem Cells", *The Journal of Clinical Investigation*, 114(6), (Sep. 2004), 795-804.

Pack, P., "Improved Bivalent Miniantibodies, With Identical Avidity as Whole Antibodies, Produced by High Cell Density Fermentation of *Escherichia coli*", *Bio/Technology*. 11(11), (Nov. 1993),1271-1277.

Palko, L., et al., "The Yin Yang-1 (YY1) Protein Undergoes a DNA-Replication-Associated Switch in Localization From the Cytoplasm to the Nucleus at the Onset of S Phase", *Journal of Cell Science*, 117(3), (2004), 465-476.

Park, C. H., et al., "Mouse Myeloma Tumor Stem Cells: A Primary Cell Culture Assay", *J. Nat. Cancer Inst.*, 46(2), (Feb. 1971), 411-422.

Parmley, S. F., "Antibody-Selectable Filamentous fd Phage Vectors: Affinity Purification of Target Genes", *Gene*, 73(2), (Dec. 1988), 305-318.

Perez-Losada, J., et al., "Stem-Cell Hierarchy in Skin Cancer", *Nature Rewiews*, 3, (Jun. 2003), 434-443.

Poulsom, R., et al., "Bone Marrow Contributes to Renal Parenchymal Turnover and Regeneration", *Journal of Pathology*, 195, (2001), 229-235.

Presta, L. G., "Antibody Engineering", *Current Opinion in Structural Biology*, 3(4), (1992), 593-596.

Ramaltho-Santos, M., et al., ""Stemness": Transcriptional Profiling of Embryonic and Adult Stem Cells", *Science*, 298, (Oct. 18, 2002), 597-600.

Reya, T., et al., "Stem Cells, Cancer, and Cancer Stem Cells", *Nature*, 414, (Nov. 2001), 105-111.

Richards, M., et al., "The Transcriptome Profile of Human Embryonic Stem Cells as Defined by SAGE", *Stem Cells*, 22, (2004), 51-64.

Riechmann, L., "Reshaping Human Antibodies for Therapy.", *Nature*, 332(6162), (Mar. 24, 1988), 323-327.

Roberts, B. L., et al., "Directed Evolution of a Protein: Selection of Potent Neutrophil Elastase Inhibitors Displayed on M13 Fusion Phage", *Proc. Natl. Acad. Sci. USA*, 89, 2429-2433.

Rogers, M. B., et al., "Specific Expression of a Retinoic Acid-Regulated, Zinc-Finger Gene, Rex-1, in Preimplantation Embryos, Trophoblast and Spermatocytes", *Development*, 113, (1991), 815-824.

Rookmaaker, M. B., et al., "Bone-Marrow-Derived Cells Contribute to Glomerular Endothelial Repair in Experimental Glomerulonephritis", *American Journal of Pathology*, 163(2), (Aug. 2003), 553-562.

Rookmaaker, M. B., et al., "Progenitor Cells in the Kidney: Biology and Therapeutic Perspectives", *Kidney International*, 66(2), (2004), 518-522.

Rosner, M. H., et al., "A POU-Domain Transcription Factor in Early Stem Cells and Germ Cells of the Mammalian Embryo", *Nature*, 345, (Jun. 21, 1990), 686-692.

Russell, S. J., "Retroviral Vectors Displaying Functional Antibody Fragments", *Nucleic Acids Research*, 21(5), (1993), 1081-1085.

Russo, P., "Localized Renal Cell Carcinoma", *Current Treatment Options in Oncology*., 2(5), (Oct. 2001), 447-455.

Schöler, H. R., et al., "New Type of POU Domain in Germ Line-Specific Protein Oct-4", *Natures*, 344, (Mar. 29, 1990), 435-439.

Schöler, H. R., et al., "Oct-4: A Germline-Specific Transcription Factor Mapping to the Mouse t-Complex", *The EMBO Journal*, 9(7), (1990), 2185-2195.

Schwede, T., et al., "Swiss-Model: An Automated Protein Homology-Modelling Server", *Nucleic Acids Research*, 31(13), (2003),3381-3385.

Scott, J. K., "Discovering Peptide Ligands Using Epitope Libraries", *Trends in Biochemical Sciences*, 17(7), (Jul. 1992), 241-245.

Sell, S., "Cellular Origin of Cancer: Dedifferentiation or Stem Cell Maturation", *Environmental Health Perspectives*, 101(*Supp. 5*), (Dec. 1993), 15-26.

Singh, S. K., et al., "Cancer Stem Cells in Nervous System Tumors", *Oncogene*, 23, (2004), 7267-7273.

Takahashi, M., et al., "Molecular Subclassification of Kidney Tumors and the Discovery of New Diagnostic Markers", *Oncogene*, 22, (2003), 6810-6818.

Tan, M.-H., et al., "Gene Expression Profiling of Renal Cell Carcinoma", *Clinical Cancer Research*, 10(*Suppl.*), (Sep. 15, 2004), 6315s-6321s.

Thompson, J. R., et al., "Retinoic Acid Induces Parietal Endoderm but not Primitive Endoderm and Visceral Endoderm Differentiation in F9 Teratocarcinoma Stem Cells With a Targeted Deletion of the Rex-1 (Zfp-42) Gene", *Molecular and Cellular Endrocrinology*, 195, (2002), 119-133.

Tickoo, S. K., et al., "Discriminant Nuclear Features of Renal Oncocytoma and Chromophobe Renal Cell Carcinoma", *American Journal of Clinical Pathology*, 110(6), (Dec. 1998), 782-787.

Tighe, A. P., et al., "Retinoic Acid Inhibits Leukemia Inhibitory Factor Signaling Pathways in Mouse Embryonic Stem Cells", *Journal of Cellular Physiology*, 198, (2004), 223-229.

Toubeau, G., et al., "Renal Tissue Expression of EGF and EGF Receptor After Ischaemic Tubular Injury: An Immunohistochemical Study", *Experimental Nephrology*, 2(4), (Jul.-Aug. 1994), 229-239.

Tumbar, T., et al., "Defining the Epithelial Stem Cell Niche in Skin", *Science*, 303, (Jan. 16, 2004), 359-363.

Vaswani, S. K., "Humanized Antibodies as Potential Therapeutic Drugs", *Annals of Allergy, Asthma, & Immunology*, 81(2), (1998), 105-119.

Venturini, F. M., et al., "Phage Display of the Minibody: A β-Scaffold for the Selection of Conformationally-Constrained Peptides", *Protein and Peptide Letters*, 1(1), (1994), 70-75.

Walker, G. T., "Strand Displacement Amplification—an Isothermal, in vitro DNA Amplification Technique", *Nucleic Acids Research*, 20(7), (Apr. 11, 1992), 1691-1696.

Wallin, A., et al., "Mechanism of the Nephrogenic Repair Response—Studies on Proliferation and Vimentin Expression After $^{35}$S-1,2-Dichlorovinyl-L-Cysteine Nephrotoxicity in vivo and in Cultured Proximal Tubule Epithelial Cells", *Laboratory Investigation*, 66(4), (1992), 474-484.

Welm, B. E., et al., "Sca-1$^{pos}$ Cells in the Mouse Mammary Gland Represent an Enriched Progenitor Cell Population", *Developmental Biology*, 245, (2002), 42-56.

Wodinisky, I., et al., "Spleen Colony Studies of Leukemia L1210. I. Growth Kinetics of Lymphocytic L1210 Cells in Vivo as Determined by Spleen Colony Assay", *Cancer Chemotherapy Reports*, 51(7), (Dec. 1967), 415-421.

Young, A. N., et al., "Expression Profiling of Renal Epithelial Neoplasms—A Method for Tumor Classification and Discovery of Diagnostic Molecular Markers", *American Journal of Pathology*, 158(5), (May 2001), 1639-1651.

Zepeda, M. L., et al., "Characterization of Stem Cells in Human Airway Capable of Reconstituting a Fully Differentiated Bronchial Epithelium", *Somatic Cell and Molecular Genetics*, 21(1), (Jan. 1995), 61-73.

"U.S. Appl. No. 11/148,149, Restriction Requirement mailed Jan 19, 2007", 7 pgs.

* cited by examiner

A

B

C

D

SEQUENCE LISTING

<160> NUMBER OF SEQ ID NOS: 16

<210> SEQ ID NO 1
<211> LENGTH: 310
<212> TYPE: PRT
<213> ORGANISM: Homo sapiens

<400> SEQUENCE: 1

```
Met Ser Gln Gln Leu Lys Lys Arg Ala Lys Thr Arg His Gln Lys Gly
 1               5                  10                  15
Leu Gly Gly Arg Ala Pro Ser Gly Ala Lys Pro Arg Gln Gly Lys Ser
                20                  25                  30
Ser Gln Asp Leu Gln Ala Glu Ile Glu Pro Val Ser Ala Val Trp Ala
            35                  40                  45
Leu Cys Asp Gly Tyr Val Cys Tyr Glu Pro Gly Pro Gln Ala Leu Gly
        50                  55                  60
Gly Asp Asp Phe Ser Asp Cys Tyr Ile Glu Cys Val Ile Arg Gly Glu
65                  70                  75                  80
Phe Ser Gln Pro Ile Leu Glu Gly Asp Ser Leu Phe Glu Ser Leu Glu
                85                  90                  95
Tyr Leu Lys Lys Gly Ser Glu Gln Gln Leu Ser Gln Lys Val Phe Glu
                100                 105                 110
Ala Ser Ser Leu Glu Cys Ser Leu Glu Tyr Met Lys Lys Gly Val Lys
            115                 120                 125
Lys Glu Leu Pro Gln Lys Ile Val Gly Glu Asn Ser Leu Glu Tyr Ser
        130                 135                 140
Glu Tyr Met Thr Gly Lys Lys Leu Pro Pro Gly Gly Ile Pro Gly Ile
145                 150                 155                 160
Asp Leu Ser Asp Pro Lys Gln Leu Ala Glu Phe Ala Arg Lys Lys Pro
                165                 170                 175
Pro Ile Asn Lys Glu Tyr Asp Ser Leu Ser Ala Ile Ala Cys Pro Gln
                180                 185                 190
Ser Gly Cys Thr Arg Lys Leu Arg Asn Arg Ala Ala Leu Arg Lys His
            195                 200                 205
Leu Leu Ile His Gly Pro Arg Asp His Val Cys Ala Glu Cys Gly Lys
        210                 215                 220
Ala Phe Val Glu Ser Ser Lys Leu Lys Arg His His Leu Val His Thr
225                 230                 235                 240
Gly Glu Lys Pro Phe Arg Cys Thr Phe Glu Gly Cys Gly Lys Arg Phe
                245                 250                 255
Ser Leu Asp Phe Asn Leu Arg Thr His Val Arg Ile His Thr Gly Glu
                260                 265                 270
Lys Arg Phe Val Cys Pro Phe Gln Gly Cys Asn Arg Arg Phe Ile Gln
            275                 280                 285
Ser Asn Asn Leu Lys Ala His Ile Leu Thr His Ala Asn Thr Asn Lys
        290                 295                 300
Asn Glu Gln Glu Gly Lys
305                 310
```

<210> SEQ ID NO 2
<211> LENGTH: 2649
<212> TYPE: DNA
<213> ORGANISM: Homo sapiens

<400> SEQUENCE: 2

-continued

```
agtttctcct tgttttacg tttgggagga ggtggcattg gaaatagcag agtgcttcgc      60
ggtaacaggg gttggagtgc aatggtgtga tctcagctca ctgcaacccc tgcctcccag    120
gctccagcga tcctcccacc tcagcctcct gaatagctga ccaccagcac actaggcaaa    180
cccaccccac tcaccgcctc ccttgggaat tcagacctaa ccatcgctga gctgaaacaa    240
atgtactgag gctggagcct gtgtgaacag aacagaagag gccttcactc tagtagtgct    300
cacagtccag caggtgtttg ctgaagacag cttactcaga tcactactgc ctggaggtgg    360
ttgatatatc ctggtgtaaa ccttcaagaa gggcacaggc aggaaaacat gagccagcaa    420
ctgaagaaac gggcaaagac aagacaccag aaaggcctgg gtggaagagc ccccagtggg    480
gctaagccca gcaaggcaa gtcaagccaa gacctgcagg cggaaataga acctgtcagc    540
gcggtgtggg ccttatgtga tggctatgtg tgctatgagc ctggccctca ggctctcgga    600
ggggatgatt tctcagactg ttacatagaa tgcgtcataa ggggtgagtt ttctcaaccc    660
atcctggaag gggactcact tttgagtcc ttggaatacc taaagaaagg atcagaacaa    720
cagctttctc aaaaggtttt cgaagcaagc tcccttgaat gttctttgga atacatgaaa    780
aaagggtaa agaaagagct tccacaaaag atagttggag agaattcgct tgagtattct    840
gagtacatga caggcaagaa gcttccgcct ggaggaatac ctggcattga cctatcagat    900
cctaaacagc tcgcagaatt tgctagaaag aagccccca taataaaga atatgacagt    960
ctgagcgcaa tcgcttgtcc tcagagtgga tgcactagga agttgaggaa tagagctgcc   1020
ctgagaaagc atctcctcat tcatggtccc cgagaccacg tctgtgcgga atgtgggaaa   1080
gcgttcgttg agagctcaaa actaaagaga catttcctgg ttcatactgg agagaagccg   1140
tttcggtgca cttttgaagg gtgcggaaag cgcttctctc tggactttaa tttgcgtacg   1200
cacgtgcgca tccacacggg ggagaaacgt ttcgtgtgtc cctttcaagg ctgcaacagg   1260
aggtttattc agtcaaataa cctgaaagcc cacatcctaa cgcatgcaaa tacgaacaag   1320
aatgaacaag agggaaagta gtcctccaac aggatgaagc agattaacag aagagtgatc   1380
agtgacaaac atgcctcatt gattattgtt tctaggaagg aatttttaaa tcaatattgc   1440
aaccccaaaa gcggttataa tttggtgtta ctaagatgct cctacacttt gtgataccgt   1500
tttaaggaca tggtgcattt tttttctt tatttgtttt atttagaact ttttttattt     1560
gttttattta gaactttgtg tgttcttaaa gtgtgcttcc aacaggaagg tcagtgataa   1620
attgacttca aaagcataac cttcaatata ttatctgttg gattattgga tataagactt   1680
attttcatgt actataaata tgaaaataac tttgattttt aattgtgtag tttccatttc   1740
ttagcttttg cctttaaat ttatacttca gccaggcata tgactgatg cctgtaatcc     1800
caacactttg ttgggaggcc aaagcaggag gatagcttga ggccaggagt tccagaccag   1860
cctgggcaac atagtgagat cctgtctcta caaaaaaat tgtttttatt tgtatttata   1920
tattttatt tttgtttttg ttggtaggcg tctcgctctg tcacccaggc tggagtctag    1980
tgtcgtgatc ttggctcact gcaacctcca cctcccgggt tcaagtgatt ctctggcctc   2040
agcctcccaa gtagctggga ctacaggtgt gtgtcaccac gcccggctaa ttttttgtatt  2100
tttagtagag atggggtttc accatgttgg ccaggctagt ctcaaactcc tgacctccag   2160
tgatctgccc acctcggcct cccaaagtgc tgggattaca ggtgtgagcc actgtgcctg   2220
gcccccaca acatgtttaa acttagctag gcctggttgc atacacctgt gttcccagct    2280
actcaggagg ctgaagcagg aggatagctt gagcccagga gtttgaggct acagtgagct   2340
```

```
gtgattgcac cactgtactc cagactggat aacagcaaga gcccatcttt taaaaaaagt    2400
aaaaattaaa aatatacttc atggttcatg tcatagccct agagaatgaa aaatttgcag    2460
tagatagtca ataaatgaat cagtagttaa atattcctta aagtcaactg tatttcattg    2520 tgattttgt tttctttta tcattgtatc aaactatatg gaaatcatat ggttagatgt     2580
gattatttga taatgttagt ccatttgaat ccattttaga tatttcacaa ttaaagaata    2640
tgaaacttc                                                            2649

<210> SEQ ID NO 3
<211> LENGTH: 23
<212> TYPE: RNA
<213> ORGANISM: Artificial Sequence
<220> FEATURE:
<223> OTHER INFORMATION: A synthetic siRNA.

<400> SEQUENCE: 3
aaauagcaga gugcuucgcg guu                                              23

<210> SEQ ID NO 4
<211> LENGTH: 23
<212> TYPE: DNA
<213> ORGANISM: Artificial Sequence
<220> FEATURE:
<223> OTHER INFORMATION: A synthetic siRNA.

<400> SEQUENCE: 4
aaugguguga ucucagcuca cuu                                              23

<210> SEQ ID NO 5
<211> LENGTH: 25
<212> TYPE: DNA
<213> ORGANISM: Artificial Sequence
<220> FEATURE:
<223> OTHER INFORMATION: A synthetic siRNA.

<400> SEQUENCE: 5
aaacccaccc cacucaccgc cucuu                                            25

<210> SEQ ID NO 6
<211> LENGTH: 11
<212> TYPE: DNA
<213> ORGANISM: Artificial Sequence
<220> FEATURE:
<223> OTHER INFORMATION: A synthetic oligonucleotide that binds to
      REX-1.
<220> FEATURE:
<221> NAME/KEY: misc_feature
<222> LOCATION: 5, 8, 9, 10
<223> OTHER INFORMATION: N = A, T, G or C

<400> SEQUENCE: 6
ccatnttnnn a                                                           11

<210> SEQ ID NO 7
<211> LENGTH: 22
<212> TYPE: DNA
<213> ORGANISM: Homo sapiens

<400> SEQUENCE: 7
gctgaccacc agcacactag gc                                               22

<210> SEQ ID NO 8
<211> LENGTH: 24
<212> TYPE: DNA
```

-continued

<210> SEQ ID NO 8
<211> LENGTH: 24
<212> TYPE: DNA
<213> ORGANISM: Homo sapiens

<400> SEQUENCE: 8
tttctggtgt cttgtctttg cccg          24

<210> SEQ ID NO 9
<211> LENGTH: 22
<212> TYPE: PRT
<213> ORGANISM: Homo sapiens

<400> SEQUENCE: 9

Ser Asn Asn Leu Lys Ala His Ile Leu Thr His Ala Asn Thr Asn Lys
1               5                   10                  15

Asn Glu Gln Glu Gly Lys
            20

<210> SEQ ID NO 10
<211> LENGTH: 21
<212> TYPE: DNA
<213> ORGANISM: Homo sapiens

<400> SEQUENCE: 10
gctcgtcgtc gacaacggct c             21

<210> SEQ ID NO 11
<211> LENGTH: 23
<212> TYPE: DNA
<213> ORGANISM: Homo sapiens

<400> SEQUENCE: 11
gtacatggct ggggtgttga agg            23

<210> SEQ ID NO 12
<211> LENGTH: 34
<212> TYPE: DNA
<213> ORGANISM: Artificial Sequence
<220> FEATURE:
<223> OTHER INFORMATION: A synthetic oligonucleotide.

<400> SEQUENCE: 12
cgcggatcca tgagccagca actgaagaaa cggg       34

<210> SEQ ID NO 13
<211> LENGTH: 35
<212> TYPE: DNA
<213> ORGANISM: Artificial Sequence
<220> FEATURE:
<223> OTHER INFORMATION: A synthetic oligonucleotide.

<400> SEQUENCE: 13
gaagatcttc caatgaggca tgtttgtcac tgatc      35

<210> SEQ ID NO 14
<211> LENGTH: 164
<212> TYPE: PRT
<213> ORGANISM: Homo sapiens

<400> SEQUENCE: 14

Met Cys Lys Leu Arg Pro Leu Leu Gln Lys Trp Val Glu Glu Ala Asp
1               5                   10                  15

Asn Asn Glu Asn Leu Gln Glu Ile Cys Lys Ala Glu Thr Leu Val Gln
            20                  25                  30

Ala Arg Lys Arg Lys Arg Thr Ser Ile Glu Asn Arg Val Arg Gly Asn

-continued

```
                35                  40                  45
Leu Glu Asn Leu Phe Leu Gln Cys Pro Lys Pro Thr Leu Gln Gln Ile
    50                  55                  60

Ser His Ile Ala Gln Gln Leu Gly Leu Glu Lys Asp Val Val Arg Val
65                  70                  75                  80

Trp Phe Cys Asn Arg Arg Gln Lys Gly Lys Arg Ser Ser Ser Asp Tyr
                85                  90                  95

Ala Gln Arg Glu Asp Phe Glu Ala Ala Gly Ser Pro Phe Ser Gly Gly
            100                 105                 110

Pro Val Ser Phe Pro Leu Ala Pro Gly Pro His Phe Gly Thr Pro Gly
            115                 120                 125

Tyr Gly Ser Pro His Phe Thr Ala Leu Tyr Ser Ser Val Pro Phe Pro
    130                 135                 140

Glu Gly Glu Ala Phe Pro Pro Val Ser Val Thr Thr Leu Gly Ser Pro
145                 150                 155                 160

Met His Ser Asn

<210> SEQ ID NO 15
<211> LENGTH: 26
<212> TYPE: DNA
<213> ORGANISM: Homo sapiens

<400> SEQUENCE: 15
gctcagcgcc agcatcgccc cacttg                                        26

<210> SEQ ID NO 16
<211> LENGTH: 23
<212> TYPE: DNA
<213> ORGANISM: Homo sapiens

<400> SEQUENCE: 16
cgtcagacac catggggaag gtg                                           23
```

DETECTION AND MODULATION OF CANCER STEM CELLS

CROSS-REFERENCE TO RELATED APPLICATIONS

This patent claims the benefit of priority, under 35 U.S.C. Section 119(e), to U.S. Provisional Patent Application Ser. No. 60/578,461 filed on Jun. 9, 2004, which is incorporated by reference herein in its entirety.

GOVERNMENT FUNDING

The invention described herein was made with support from the United States Government under grant number R01CA39036 awarded by the National Institutes of Health. The United States Government has certain rights in the invention.

FIELD OF THE INVENTION

The invention relates to a cancer stem cell marker, rex-1, a gene that controls stem cell differentiation.

BACKGROUND OF THE INVENTION

Currently available procedures for treating cancer have several drawbacks: (1) existing chemotherapeutic agents are not as effective as required against late stage/metastatic cancers, (2) many chemotherapeutic regimens have significant side effects, and (3) even after a course of chemotherapy, there is a significant possibility that the cancerous growth will re-occur. Accurate methods for identifying and targeting cancer stem cells not only permit improved medical diagnosis and treatment of the associated cancer, but also enable drug screening for developing or identifying drugs effective against cancer regenerating cells such as cancer stem cells.

Evidence is accumulating that primitive cancerous stem cells for hematopoietic cancers and several types of solid tumors exist. See e.g., Cooper, G. M. ELEMENTS OF HUMAN CANCER, Jones and Bartlett Publishers, 1992, ISBN: 0867201916; Bonnet D. and Dick J. E. *Human acute myeloid leukemia is organized as a hierarchy that originates from a primitive hematopoietic cell*, Nature Medicine 3: 730-737 (1997); Park C. H., Bergsagel D. E., and McCulloch E. A. Mouse myeloma tumor stem cells: a primary cell culture assay, J. Nat. Cancer Inst. 46: 411-422 (1971); Hamburger A. W. and Salmon S. E. *Primary bioassay of human tumor stem cells*, Science, 197: pp. 461-463 (1977); and U.S. Pat. No. 4,411,990 to Salmon, et al. entitled Primary bioassay of human tumor stem cells, issued Oct. 25, 1983.

Current methods for diagnosing or treating cancer, removing cancer cells from transplant grafts prior to injection into a patient, or methods to screen the efficacy of anti-cancer agents in completely eliminating cancer cells, do not account for the presence of cancer stem cells, which can propagate, differentiate into mature cancer cells and self-renew, thereby reforming cancers and leading to remissions.

Accordingly, there exists a need for new methods for diagnosing or treating cancer, removing cancer cells from transplant grafts prior to injection into a patient, and methods to screen the efficacy of anti-cancer agents in eliminating cancer cells, which account for and/or are specifically directed to cancer stem cells and/or progenitor cells.

SUMMARY OF THE INVENTION

The invention relates to the discovery that rex-1 is a marker for cancer stem cells. The invention therefore provides compositions and methods for detecting and treating cancer. In some embodiments, cancer is detected by screening a tissue or cell sample for cells that express more or less rex-1 than non-cancer cells of the same cell type. In other embodiments, cancer is treated by administering an agent to a mammalian subject that can modulate the expression of rex-1 or the activity of the REX-1 protein.

One aspect of the invention is a method for detecting cancer in a test tissue sample comprising detecting cancer stem cells in the tissue sample by contacting the test tissue sample with an anti-REX-1 antibody and detecting whether REX-1 protein is present in substantially or significantly different levels in cells in the test tissue sample relative to a control tissue sample. Preferably, the test tissue sample and the control tissue sample are of the same tissue type. The cancer can be a metastatic cancer. For example, the anti-REX-1 antibody can bind to a REX-1 peptide having amino acid sequence SNNLKAHILTHANTNKNEQEGK (SEQ ID NO:9).

Another aspect of the invention is a method for detecting metastatic cancer in a patient comprising detecting cancer stem cells in a test tissue sample obtained from the patient by contacting the test tissue sample with an anti-REX-1 antibody and detecting whether REX-1 protein is present in substantially or significantly different levels in cells in the test tissue sample relative to a control tissue sample; wherein the tissue sample is obtained from a site in the patient that is distinct from a primary cancer site. Preferably, the test tissue sample and the control tissue sample are of the same tissue type. For example, the anti-REX-1 antibody can bind to a REX-1 peptide having amino acid sequence SNNLKAHILTHANTNKNEQEGK (SEQ ID NO:9).

Another aspect of the invention is a method for detecting cancer in a test tissue sample comprising detecting cancer stem cells in the test tissue sample by performing a quantitative nucleic acid amplification assay on RNA isolated from the test tissue sample using amplification primers that are complementary to a human rex-1 nucleic acid having SEQ ID NO:2, and detecting whether a rex-1 nucleic acid amplification product is present in substantially or significantly different levels in cells in the test tissue sample relative to a control tissue sample. Preferably, the test tissue sample and the control tissue sample are of the same tissue type. The cancer can be a metastatic cancer.

Another aspect of the invention is a method for detecting metastatic cancer in a tissue sample comprising detecting cancer stem cells in the tissue sample by performing a nucleic acid amplification assay on RNA isolated from the tissue sample using amplification primers that are complementary to a human rex-1 nucleic acid having SEQ ID NO:2, and detecting whether a rex-1 nucleic acid amplification product is present in substantially or significantly different levels in cells in the test tissue sample relative to a control tissue sample; wherein the tissue sample is obtained from a site in the patient that is distinct from a primary cancer site. For example, the amplification primers can have SEQ ID NO:7, 8, 12 or 13.

Another aspect of the invention is a method for treating cancer in a patient comprising administering to the patient an effective amount of an agent that can modulate rex-1 expression or REX-1 activity. Examples of agents that can modulate rex-1 expression include small interfering RNAs (siRNAs), ribozymes, or antisense nucleic acids that can hybridize to a nucleic acid comprising SEQ ID NO:2. For example, the small interfering RNA (siRNA) can be a double stranded RNA comprising SEQ ID NO:3, 4 or 5. Moreover, the agent that can modulate rex-1 expression can be an oligonucleotide that binds to REX-1, wherein the oligonucleotide is linked to a cytotoxin. Such an oligonucleotide that binds to REX-1 can include the sequence CCATNTTNNNA (SEQ ID NO:6), where N is any nucleotide (A, C, G or T).

Another aspect of the invention is a method for identifying an anti-cancer agent comprising contacting a cancerous cell that expresses rex-1 with a test agent and determining whether the cell expresses substantially different levels of rex-1 after incubation of the cell with the test agent than when the cancerous cell is not incubated with the test agent. For example, the expression of rex-1 can be detected using an anti-REX-1 antibody. One example of an anti-REX-1 antibody is one that binds to a REX-1 peptide having amino acid sequence SNNLKAHILTHANTNKNEQEGK (SEQ ID NO:9). Moreover, the expression of rex-1 can be detected and/or quantified using nucleic acid amplification of a rex-1 mRNA. For example, amplification primers having SEQ ID NO:7, 8, 12 or 13 can be employed in the nucleic acid amplification.

Another aspect of the invention is a method for maintaining a cell in an undifferentiated state comprising modulating rex-1 expression or REX-1 activity in the cell. For example, the REX-1 protein can have the sequence SEQ ID NO:1. A nucleic acid having SEQ ID NO:2 can be introduced into the cell to permit expression, or over-expression of REX-1. Alternatively, small interfering RNAs (siRNAs), ribozymes, or antisense nucleic acids that can hybridize to a nucleic acid comprising SEQ ID NO:2 can be administered or introduced to the cell.

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 6:
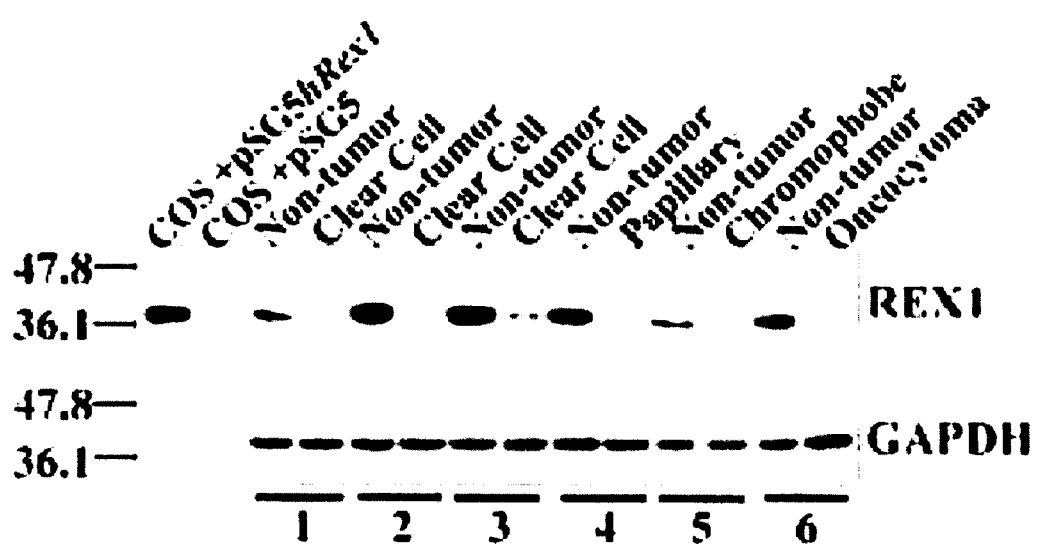

FIG. 6 illustrates expression of human REX-1 protein in renal tumors and adjacent, non-tumorous renal parenchyma from six patients as determined by Western blot analysis. Results from six patients are shown. Pairs 1-3, non-tumor and adjacent clear cell carcinoma; Pair 4, non-tumor and adjacent papillary carcinoma; Pair 5, non-tumor and adjacent chromophobe carcinoma; and Pair 6, non-tumor and an adjacent oncocytoma renal tumor. COS cells transiently transfected with a vector expressing Rex-1 or an empty vector were used as positive and negative controls, respectively. GAPDH was used to confirm the integrity of proteins. Ten micrograms of COS cell protein extract (positive and negative control), and 100 μg of extracted protein for each patient sample was used. Products were separated on a 10% SDS-acrylamide gel. Molecular masses from protein molecular weight markers are indicated on the left. All Western blots were performed in triplicate with identical results. One experiment is shown.

FIG. 7A-L illustrate expression of REX-1 protein in formalin-fixed, paraffin-embedded sections as well as frozen sections from human renal specimens as observed by immunohistochemistry. Three patient samples with renal cell carcinoma and adjacent, non-tumor renal parenchyma were stained with the affinity-purified, polyclonal rabbit anti-human REX-1 antibody. The two formalin-fixed sections were from clear cell carcinoma specimens, and the frozen section was from a papillary carcinoma specimen. Panels A-D and panels E-H were from the two patients with clear cell carcinoma, and panels I-L were from the patient with papillary carcinoma. In normal renal tissue, the REX-1 antibody predominantly stained the cytoplasmic region of a small percentage (~1-2%) of epithelial cells of the proximal convoluted tubules (A, E, and I). This staining was not observed in negative controls (C, G, and K). There was an absence of REX-1 immunostaining in all three carcinoma specimens (B, F, and J) and respective negative control (D, H, and L). 600× magnification.

Figure 8A:
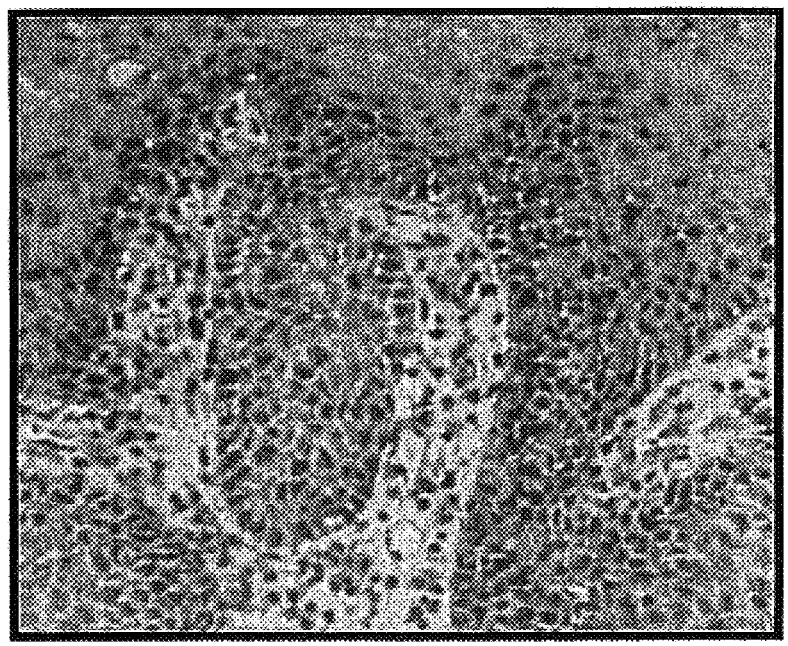

FIG. 8A illustrates decreased expression of REX-1 protein in cancerous human laryngeal cells relative to normal laryngeal cells. The cancerous laryngeal cells were moderately differentiated and could be readily distinguished from normal cells in the same microscopic field by their phenotype. Such moderately differentiated cancer cells exhibited substantially no or only low levels of REX-1 expression while phenotypically normal cells exhibited substantial REX-1 expression, as indicated by the darker stained normal cells in this section.

Figure 8B:
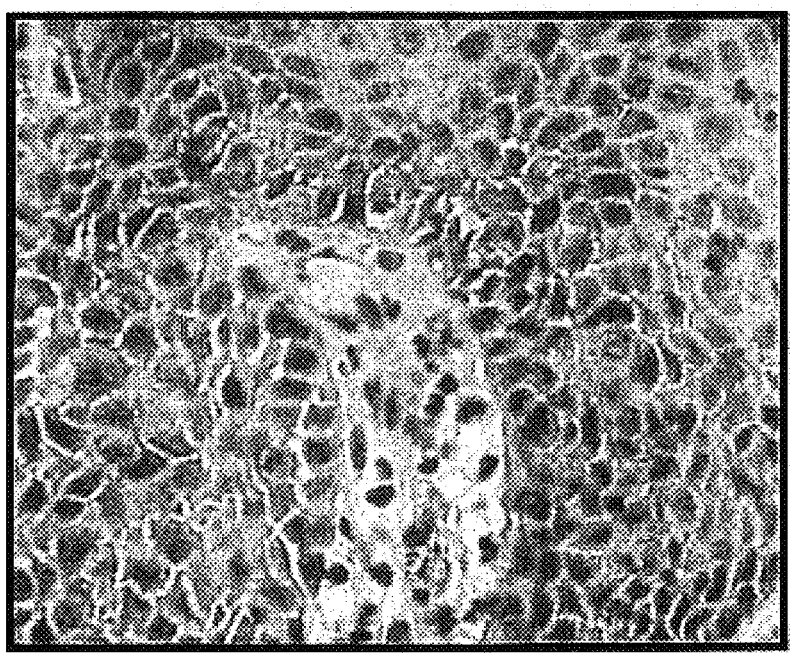

FIG. 8B provides a view of a portion of the section shown in FIG. 8A under higher magnification.

Figure 8C:
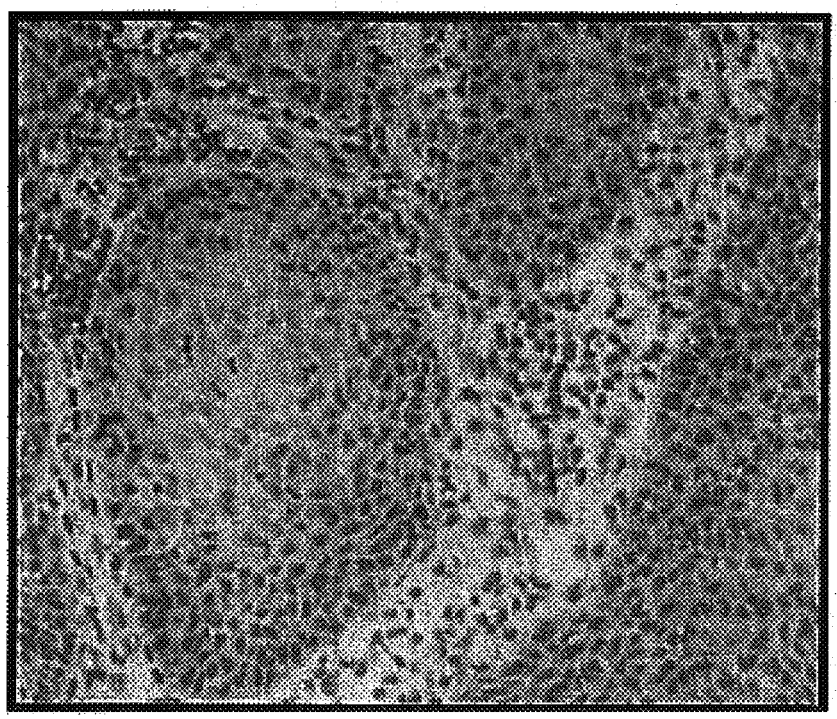

FIG. 8C shows a section of cancerous laryngeal tissue that was not stained with anti-REX-1 antibodies, as a control for FIGS. 8A-B.

Figure 9A:
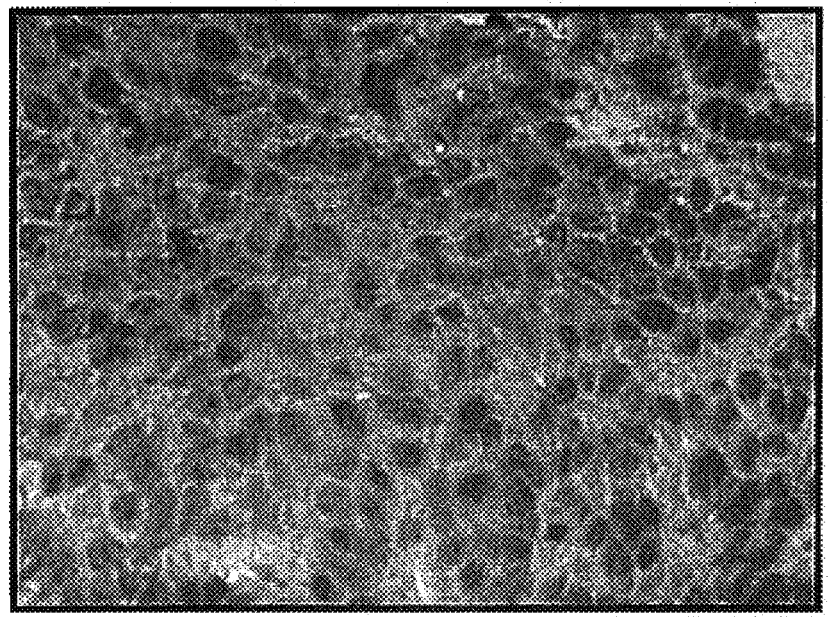

FIG. 9A illustrates decreased expression of REX-1 protein in cancerous cells of a floor of the mouth tissue specimen. The cancerous cells comprised an invasive, moderately differentiated form of squamous cell carcinoma (SCC). The moderately differentiated phenotypically cancerous SCC cells stained weakly with the anti-REX-1 antibody.

Figure 9B:
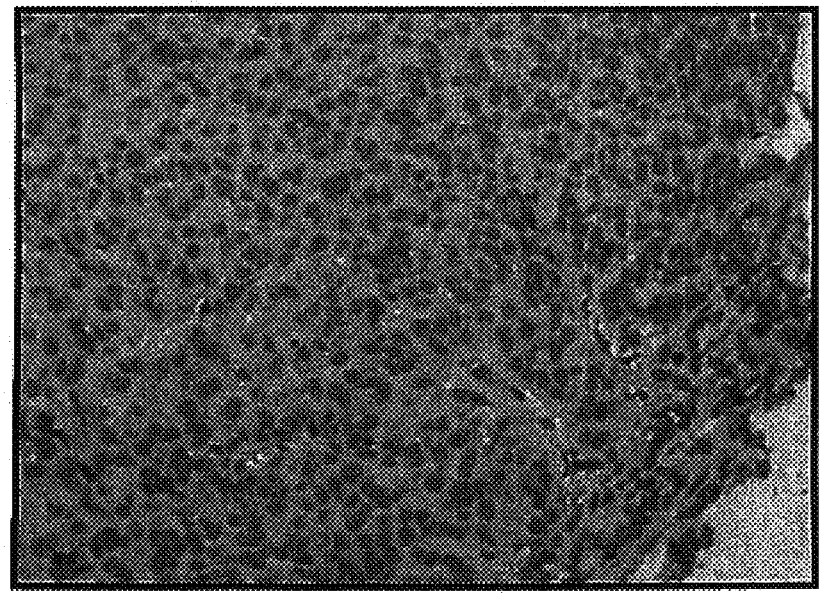

FIG. 9B shows a section of mouth tissue from the same specimen that was not stained with anti-REX-1 antibodies. This section provides a control for FIG. 9A.

Figure 10A:
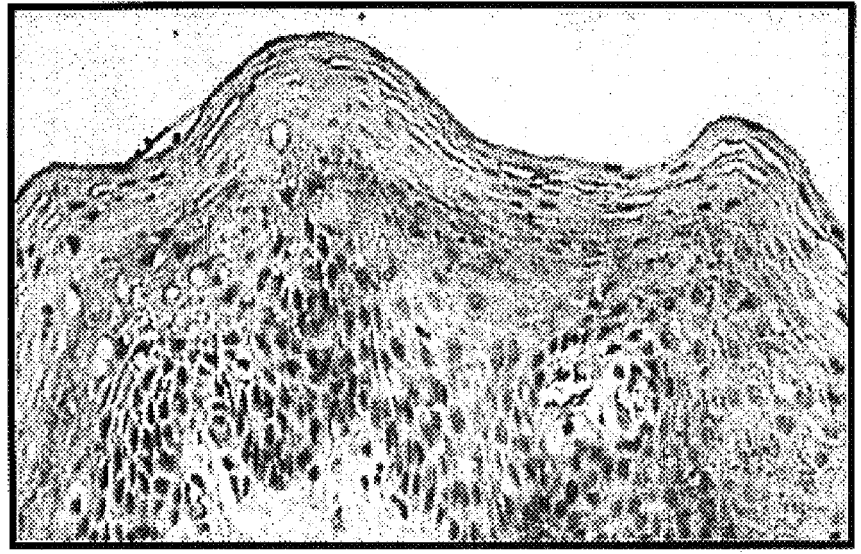

FIG. 10A illustrates decreased expression of REX-1 protein in moderately differentiated cancer cells from a specimen of the floor of the mouth. The cancer cells were invasive and moderately differentiated and were readily identified as cancerous by their phenotype. REX-1 expression was observed in many phenotypically normal cells as indicated by the darker stained cells in this section.

Figure 10B:
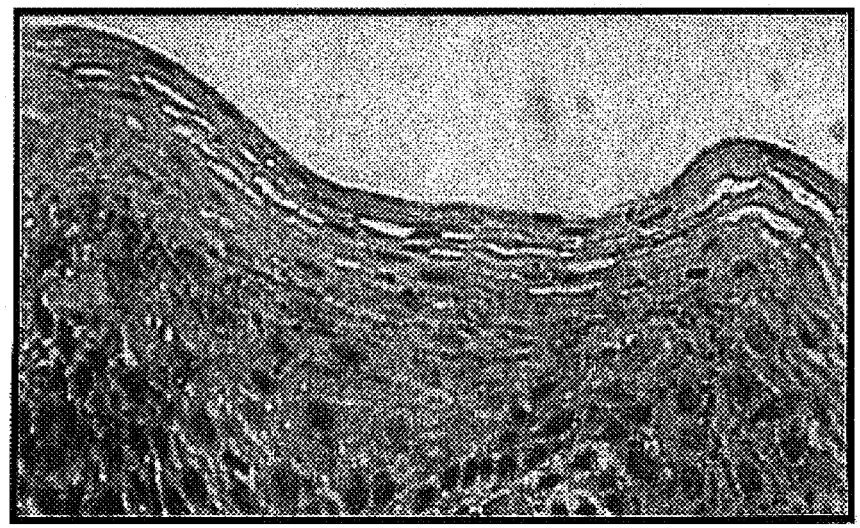

FIG. 10B provides a view of a portion of the section shown in FIG. 10A under higher magnification.

Figure 10C:
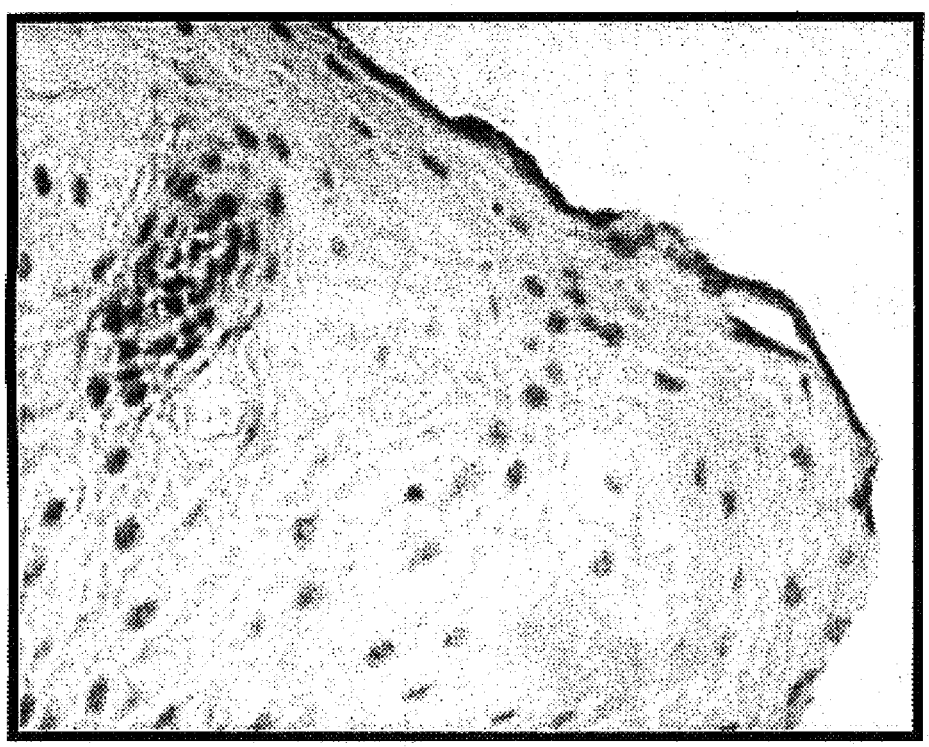

FIG. 10C shows a section of normal overlying epithelium that was not stained with anti-REX-1 antibodies. This section provides a control for FIGS. 10A-B.

DETAILED DESCRIPTION OF THE INVENTION

According to the invention, cancer stem cells express different levels of rex-1 than normal stem cells or normal cells in the same tissue. The invention provides compositions and methods for detecting and treating cancer that involve detecting cells that express different levels of rex-1 and targeting agents to those cells that can modulate rex-1 expression or the activity of REX-1 protein.

Cancer Stem Cells

Stem cells are functionally characterized by the ability to self renew and differentiate into distinct cell lineages. It has been established that embryonic stem (ES) cells, derived from the inner cell mass of the developing blastocyst, are pluripotent, undifferentiated cells with the potential to proliferate, self-renew, and generate new tissues. Such ES cells have now been isolated from both mouse and human embryos. In addition, stem cells have been identified within adult, differentiated tissues. These adult stem cells, sometimes also termed multi-potent adult progenitor cells (MAPCs), are believed to play essential roles in growth and tissue regeneration and have been identified in certain tissues, including the brain, epidermis, lung, breast, hematopoietic and neural systems. Gage, Science (2000) 287:1433-1438; Abeyta et al. Hum Mol Gen (2004) In press (online); Tumbar et al. Science (2004) 303; Zepeda et al. Somat Cell Mol Genet (1995) 21:61-73; Dontu et al. Genes Dev (2003) 17:1253-1270; Welm et al. Developmental Biology (2002) 245:42-56; Gudjonsson et al. Genes Dev (2002) 16:693-706; Lagasse et al. Immunity (2001) 14:425-436. Ramalho-Santos et al. Science (2002) 298:597-600.

There is evidence that many common cancers, including skin and breast cancers, in addition to leukemias, can result from transforming events that occur in adult stem cells. Perez-Losada & Balmain Nat Rev Cancer 2003; 3:434-443; Al-Hajj et al. Proc Natl Acad Sci USA 2003; 100:3983-3988; Reya et al. Nature 2001; 414:105-111. Indeed, functional parallels exist between tumorigenic and normal stem cells. Both cell types demonstrate significant proliferative potential, the ability to self-renew, and the ability to generate new tissues. However, tumorigenic stem cells lack the normal growth regulatory mechanisms that limit the uncontrolled proliferation of stem cells. Reya et al. Nature 2001; 414:105-111.

Tumorigenic stem cells arise in normal adult stem cell populations through the accumulation of multiple transforming mutations. As adult stem cells can persist and self-renew for the lifespan of the individual, these cells are more likely to accrue the genetic lesions necessary for malignant transformation. Such transformed tumorigenic stem cells, arising in normal adult stem cell populations, can initiate cancer development. Reya et al. Nature 2001; 414:105-111. Furthermore, tumorigenic stem cells may also play important roles in tumor evolution, metastatic invasion and local recurrence following treatment.

Cancer stem cells constitute only a small proportion of a tumor or a cancerous tissue. But the cancer stem cells have a unique ability to establish new colonies of cancer cells. For example, when mouse myeloma cells are obtained from mouse ascites, separated from normal hematopoietic cells, and put into in vitro colony-forming assays, only 1 in 10,000 to 1 in 100 cancer cells were able to form colonies. Park et al. *J. Natl Cancer Inst.* 46, 411-422 (1971). Even when leukemic cells were transplanted in vivo, only 1-4% of cells could form spleen colonies. Bruce et al. *Nature* 199, 79-80 (1963); Wodinsky et al. *Cancer Chemother. Rep.* 51, 415-421 (1967); Bergsagel et al. *Cancer Res.* 28, 2187-2196 (1968). Moreover it has been shown that a subset of cells from a population of seemingly homogeneous cancer cells is capable of proliferation and is clonogenic, while the remainder of cancer cells cannot undergo significant proliferation. Thus, workers have purified such a proliferative subset of leukemia cells as $CD34^+CD38^-$ cells from patient samples. Bonnet & Dick, *Nature Med.* 3, 730-737 (1997). Despite the fact that these cells represented a small and variable proportion of acute myelogenic leukemia cells (0.2% in one patient), they were the only cells capable of transferring acute myelogenic leukemia (AML) from human patients to NOD/SCID mice in the vast majority of cases. Thus, not all AML cells had a similar clonogenic capacity. Only a small, identifiable subset was consistently enriched for the ability to proliferate and transfer disease.

As used herein, a cancer stem cell is a stem cell that has a cancerous phenotype. Cancer stem cells lack the normal growth regulatory mechanisms that limit the uncontrolled proliferation of stem cells. Cancer stem cells constitute only a subset of cells from a population of seemingly homogeneous cancer cells. While cancer stem cells are capable of proliferation and are clonogenic, most cancer cells in a population of seemingly homogeneous cancer cells cannot undergo significant proliferation.

According to the invention, rex-1 is a marker for cancer stem cells. Thus, rex-1 is a cancer stem cell marker that can be used to identify and target cancer stem cells for treatment. Moreover, rex-1 is a marker of cancer stem cells for a variety of cancers. Use of rex-1 is therefore not restricted to just one type of cancer. The cancerous phenotype of the cancer stem cell can be further detected and characterized using available cancer markers.

Rex-1

Rex-1, also termed zinc-fingered protein-42 (zfp-42), has emerged as a stem cell marker in both human and mouse embryonic stem cells. The REX-1 protein binds to DNA and acts as a transcription factor. The inventors have shown that the REX-1 protein can bind to a transcriptional regulatory element having the sequence CCA TNTTNNNA (SEQ ID NO:6), where N is any nucleotide (A, C, G or T).

The Rex-1 gene was first identified in mouse F9 teratocarcinoma cells and its expression was found to decrease during cellular differentiation. Expression of Rex-1 has subsequently been detected only in a limited number of mouse cell types, including the blastocyst, undifferentiated embryonic stem cells, meiotic germ cells of the adult mouse testis, and $CD34^+$ hematopoietic progenitor cells, all of which possess multipotent differentiation capacity. For these reasons, expression of Rex-1 is believed to be characteristic of pluripotent stem cells. Brivanlou et al. Science 2003; 300:913-916; Ramalho-Santos et al. Science 2002; 298:597-600; Rogers et al. Development 1991; 113:815-824.

The human Rex-1 gene encodes an approximate 310 amino acid protein with the following sequence (SEQ ID NO:1):

```
  1 MSQQLKKRAK TRHQKGLGGR APSGAKPRQG KSSQDLQAEI

41 EPVSAVWALC DGYVCYEPGP QALGGDDFSD CYIECVIRGE

81 FSQPILEGDS LFESLEYLKK GSEQQLSQKV FEASSLECSL

121 EYMKKGVKKE LPQKIVGENS LEYSEYMTGK KLPPGGIPGI

161 DLSDPKQLAE FARKKPPINK EYDSLSAIAC PQSGCTRKLR

201 NRAALRKHLL IHGPRDHVCA ECGKAFVESS KLKRHFLVHT

241 GEKPFRCTFE GCGKRFSLDF NLRTHVRIHT GEKRFVCPFQ

281 GCNRRFIQSN NLKAHILTHA NTNKNEQEGK
```

One example of a nucleotide sequence encoding the human REX-1 protein is as follows (SEQ ID NO:2):

```
   1 AGTTTCTCCT TTGTTTTACG TTTGGGAGGA GGTGGCATTG

41 GAAATAGCAG AGTGCTTCGC GGTAACAGGG GTTGGAGTGC

81 AATGGTGTGA TCTCAGCTCA CTGCAACCCC TGCCTCCCAG

121 GCTCCAGCGA TCCTCCCACC TCAGCCTCCT GAATAGCTGA

161 CCACCAGCAC ACTAGGCAAA CCCACCCCAC TCACCGCCTC

201 CCTTGGGAAT TCAGACCTAA CCATCGCTGA GCTGAAACAA

241 ATGTACTGAG GCTGGAGCCT GTGTGAACAG AACAGAAGAG

281 GCCTTCACTC TAGTAGTGCT CACAGTCCAG CAGGTGTTTG

321 CTGAAGACAG CTTACTCAGA TCACTACTGC CTGGAGGTGG

361 TTGATATATC CTGGTGTAAA CCTTCAAGAA GGGCACAGGC

401 AGGAAAACAT GAGCCAGCAA CTGAAGAAAC GGGCAAAGAC

441 AAGACACCAG AAAGGCCTGG GTGGAAGAGC CCCCAGTGGG

481 GCTAAGCCCA GGCAAGGCAA GTCAAGCCAA GACCTGCAGG

521 CGGAAATAGA ACCTGTCAGC GCGGTGTGGG CCTTATGTGA

561 TGGCTATGTG TGCTATGAGC CTGGCCCTCA GGCTCTCGGA

601 GGGGATGATT TCTCAGACTG TTACATAGAA TGCGTCATAA

641 GGGGTGAGTT TTCTCAACCC ATCCTGGAAG GGGACTCACT

681 TTTTGAGTCC TTGGAATACC TAAAGAAAGG ATCAGAACAA

721 CAGCTTTCTC AAAAGGTTTT CGAAGCAAGC TCCCTTGAAT

761 GTTCTTTGGA ATACATGAAA AAAGGGGTAA AGAAAGAGCT

801 TCCACAAAAG ATAGTTGGAG AGAATTCGCT TGAGTATTCT

841 GAGTACATGA CAGGCAAGAA GCTTCCGCCT GGAGGAATAC

881 CTGGCATTGA CCTATCAGAT CCTAAACAGC TCGCAGAATT

921 TGCTAGAAAG AAGCCCCCCA TAAATAAAGA ATATGACAGT

961 CTGAGCGCAA TCGCTTGTCC TCAGAGTGGA TGCACTAGGA

1001 AGTTGAGGAA TAGAGCTGCC CTGAGAAAGC ATCTCCTCAT

1041 TCATGGTCCC CGAGACCACG TCTGTGCGGA ATGTGGGAAA
```

```
-continued
1081 GCGTTCGTTG AGAGCTCAAA ACTAAAGAGA CATTTCCTGG

1121 TTCATACTGG AGAGAAGCCG TTTCGGTGCA CTTTTGAAGG

1161 GTGCGGAAAG CGCTTCTCTC TGGACTTTAA TTTGCGTACG

1201 CACGTGCGCA TCCACACGGG GGAGAAACGT TTCGTGTGTC

1241 CCTTTCAAGG CTGCAACAGG AGGTTTATTC AGTCAAATAA

1281 CCTGAAAGCC CACATCCTAA CGCATGCAAA TACGAACAAG

1321 AATGAACAAG AGGGAAAGTA GTCCTCCAAC AGGATGAAGC

1361 AGATTAACAG AAGAGTGATC AGTGACAAAC ATGCCTCATT

1401 GATTATTGTT TCTAGGAAGG AATTTTTAAA TCAATATTGC

1441 AACCCCAAAA GCGGTTATAA TTTGGTGTTA CTAAGATGCT

1481 CCTACACTTT GTGATACCGT TTTAAGGACA TGGTGCATTT

1521 TTTTTTCTTT TATTTGTTTT ATTTAGAACT TTTTTTATTT

1561 GTTTTATTTA GAACTTTGTG TGTTCTTAAA GTGTGCTTCC

1601 AACAGGAAGG TCAGTGATAA ATTGACTTCA AAAGCATAAC

1641 CTTCAATATA TTATCTGTTG GATTATTGGA TATAAGACTT

1681 ATTTTCATGT ACTATAAATA TGAAATAAC TTTGATTTTT

1721 AATTGTGTAG TTTCCATTTC TTAGCTTTTG CCTTTTAAAT

1761 TTATACTTCA GCCAGGCATA GTGACTGATG CCTGTAATCC

1801 CAACACTTTG TTGGGAGGCC AAAGCAGGAG GATAGCTTGA

1841 GGCCAGGAGT TCCAGACCAG CCTGGGCAAC ATAGTGAGAT

1881 CCTGTCTCTA CAAAAAAAT TGTTTTATT TGTATTTATA

1921 TATTTTTATT TTTGTTTTTG TTGGTAGGCG TCTCGCTCTG

1961 TCACCCAGGC TGGAGTCTAG TGTCGTGATC TTGGCTCACT

2001 GCAACCTCCA CCTCCCGGGT TCAAGTGATT CTCTGGCCTC

2041 AGCCTCCCAA GTAGCTGGGA CTACAGGTGT GTGTCACCAC

2081 GCCCGGCTAA TTTTTGTATT TTTAGTAGAG ATGGGGTTTC

2121 ACCATGTTGG CCAGGCTAGT CTCAAACTCC TGACCTCCAG

2161 TGATCTGCCC ACCTCGGCCT CCCAAAGTGC TGGGATTACA

2201 GGTGTGAGCC ACTGTGCCTG GCCCCCACA ACATGTTTAA

2241 ACTTAGCTAG GCCTGGTTGC ATACACCTGT GTTCCCAGCT

2281 ACTCAGGAGG CTGAAGCAGG AGGATAGCTT GAGCCCAGGA

2321 GTTTGAGGCT ACAGTGAGCT GTGATTGCAC CACTGTACTC

2361 CAGACTGGAT AACAGCAAGA GCCCATCTTT TAAAAAAGT

2401 AAAAATTAAA AATATACTTC ATGGTTCATG TCATAGCCCT

2441 AGAGAATGAA AAATTTGCAG TAGATAGTCA ATAAATGAAT

2481 CAGTAGTTAA ATATTCCTTA AAGTCAACTG TATTTCATTG

2521 TGATTTTTGT TTTCTTTTTA TCATTGTATC AAACTATATG

2561 GAAATCATAT GGTTAGATGT GATTATTTGA TAATGTTAGT

2601 CCATTTGAAT CCATTTTAGA TATTTCACAA TTAAAGAATA

2641 TGAAACTTC
```

Although the roles of epidermal stem cells in skin and hair follicle renewal are established and epidermal keratinocyte stem cells have been isolated in long term cell cultures, expression of hRex-1 mRNA and REX-1 protein has not previously been examined in normal human epidermal keratinocyte cells. However, as described herein, reverse transcription-polymerase chain reaction and Western analyses indicate that human Rex-1 is expressed in normal human keratinocytes, as well as in bronchial and small airway epithelial cells and normal human prostate epithelial cells (FIGS. 2D and 3B).

Cancer Detection and Treatment

According to the invention, rex-1 is a marker for cancer stem cells. Moreover, rex-1 is a marker of cancer stem cells for a variety of cancers and is not restricted to just one type of cancer. Detection and targeting of cancer stem cells according to the teachings of the current invention can enable a variety of new treatments, diagnostic protocols, and drug screening assays for many forms of cancer including breast cancer, skin cancer, head cancer, neck cancers and various types of carcinomas. Currently, treatment of such cancers may involve high dose chemotherapy or radiation. Such treatment can have many negative side effects. The methods of the invention can help avoid or minimize these side effects.

As illustrated herein, rex-1 is expressed in substantially or significantly different amounts in cancerous tissues compared to normal, non-cancerous tissues of the same tissue type. As used herein, "significantly different" means that there is at least about a two-fold difference in expression, at least about a three-fold difference in expression, at least about a four-fold difference in expression, at least about a five-fold difference in expression, at least about a ten-fold difference in expression, at least about a fifteen-fold difference in expression, at least about a twenty-fold difference in expression, or at least about a fifty-fold difference in rex-1 expression, whether measured at the mRNA level or at the protein level. In some embodiments, "significantly different" is assessed statistically, wherein a p value of at least $p<0.10$ is considered significantly different, or a p value of at least $p<0.05$ is considered significantly different, or a p value of at least $p<0.01$ is considered significantly different, or a p value of at least $p<0.001$ is considered significantly different.

As used herein, "substantially different" means that there is at least about a five-fold difference in expression, at least about a ten-fold difference in expression, at least about a fifteen-fold difference in expression, at least about a twenty-fold difference in expression, or at least about a fifty-fold difference in expression, whether measured at the mRNA level or at the protein level. In some embodiments, "substantially different" is assessed statistically, wherein a p value of at least $p<0.05$ is considered substantially different, or a p value of at least $p<0.01$ is considered substantially different, or a p value of at least $p<0.001$ is considered significantly different.

While levels of rex-1 expression are generally quantified to assess whether a tissue sample or a collection of cells is cancerous. The quantification of rex-1 expression need not necessarily yield a numerical value. Thus, for example, an assessment of rex-1 expression levels can be performed by any convenient method including reverse transcription-polymerase chain reaction (RT-PCR), immunoassay, histoimmunochemistry and the like. For example, when histoimmunochemistry is used, some cells in a tissue section may express rex-1 and other cells may not. However, when test and control levels of rex-1 expression are compared, one of skill in the art can conclude that the test sample contains cancer cells when a significantly or substantially different number of cells express rex-1 in the test sample relative to the control sample that is known to contain no cancer cells. Thus, for example, microscopic examination of a test sample tissue section may have five or ten cells that express rex-1, whereas a control sample tissue section may have none or one cell that expresses rex-1. In other cases, the number of cells that express rex-1 may not be immediately ascertainable but one of skill in the art can obtain a general understanding that many more cells express rex-1 in the test or control sample, than in the respective control or test sample.

Thus, as shown herein, reverse transcription-polymerase chain reaction (RT-PCR) analysis indicates that significant levels of human rex-1 expression occur in MDA-MB-468 mammary carcinoma cells, SCC-15 squamous cell carcinoma cells and NTERA2 teratocarcinoma cells. Other types of cancer cells that express rex-1 also include breast, head, mouth, neck, larynx, teratocarcinoma and skin cancer cells.

Similarly, RT-PCR and anti-REX-1 antibody staining experiments indicate that renal carcinoma cells have significantly reduced levels of rex-1 expression relative to normal renal cells. Further experiments indicate that increased levels of REX-1 protein are present in laryngeal tumor cells relative to normal laryngeal cells, and skin cancer cells relative to normal skin cells Hence, the invention contemplates detecting cancer by detecting levels of rex-1 mRNA or REX-1 protein. In some embodiments, rex-1 mRNA can be detected by comparative or quantitative nucleic acid amplification of RNA isolated from a test sample. This method is described in more detail below. In another embodiment, REX-1 protein levels in a test sample are detected using, for example, an anti-REX-1 antibody. Such assays are also described in more detail below.

If one of skill in the art desires, the cancer cell expressing rex-1 can be further characterized by detecting whether markers of a given cancerous cells type are present. Such markers are available to one of skill in the art.

In another embodiment, the invention provides methods for treating or preventing cancer in a mammal by administering to the mammal an agent that can modulate rex-1 expression or REX-1 activity.

According to the invention, a variety of cancers can be treated or prevented from growing/spreading including, but not limited to: carcinomas such as breast, bladder, colon, kidney, larynx, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma. In some embodiments, the cancer is a carcinoma. In other embodiments, the cancer is a breast, skin, neck, head or brain cancer.

Thus, the invention provides a variety of methods for treating cancer. In one embodiment, cancer cells are treated by targeting rex-1 expressing cells with agents that can modulate the expression of rex-1, or the activity of REX-1. In another embodiment, cancer cells are treated by increasing rex-1 expression in tumor cells with agents that can modulate the expression of rex-1, or the activity of REX-1.

Any agent that inhibits or increases rex-1 expression or activity can be used in the methods of the invention. For example, agents that inhibit rex-1 expression or REX-1 activity include small interfering RNAs (siRNAs), ribozymes, antisense nucleic acids, oligonucleotides that bind to REX-1, anti-REX-1 antibodies, anti-Oct3/4 antibodies, small molecules, peptides, mutant REX-1 polypeptides and the like.

In some embodiments, the expression or activity of Oct-3/4 is modulated in order to modulate rex-1 expression. As illustrated by the inventors, the Oct-3/4 transcription factor regulates rex-1 expression. Ben-Shushan, E., Thompson, J. R., Gudas, L. J., and Bergman, Y. (1998) Rex-1, a gene encoding a transcription factor expressed in the early embryo, is regulated via Oct-3/4 and Oct-6 binding to an octamer site and a novel protein, Rox-1, binding to an adjacent site. MOL. CELL. BIOL., 18: 1866-1878.

Oct-3/4 is a POU/Homeodomain transcription factor having a sequence disclosed in Genbank Access No. NM 013633. Oct-3/4 (also called POU5F1) is expressed in undifferentiated cells early in development and later becomes restricted to oocytes, Okamoto, et al., Cell 60:461-472 (1990); Scholer, et al., Nature (London) 344:435-439 (1990); Rosner, et al., Nature (London) 345:686-692 (1990); and Scholer, et al., EMBO J. 9:2185-2195 (1990). Sequence for Oct-3/4 can be found in the database provided by the National Center for Biotechnology Information (website at ncbi.nlm.nih.gov/). For example, one sequence for human Oct-3/4 is as follows (SEQ ID NO:14).

```
  1 MCKLRPLLQK WVEEADNNEN LQEICKAETL VQARKRKRTS

41 IENRVRGNLE NLFLQCPKPT LQQISHIAQQ LGLEKDVVRV

81 WFCNRRQKGK RSSSDYAQRE DFEAAGSPFS GGPVSFPLAP

121 GPHFGTPGYG SPHFTALYSS VPFPEGEAFP PVSVTTLGSP

161 MHSN
```

Thus, agents that block Oct-3/4 transcriptional activity can be used to modulate the expression of rex-1. For example, antibodies directed against Oct-3/4 can be used to block, increase or otherwise modulate the expression of rex-1.

In other embodiments, cancer cells are treated with cytotoxic agents linked to proteins, nucleic acids or ligands that can bind to REX-1. For example, anti-REX-1 antibodies or oligonucleotides having the sequence CCATNTTNNNA (SEQ ID NO:6), where N is any nucleotide (A, C, G or T), can be used to deliver a cytotoxic agent to a cancer cell that expresses REX-1. Examples of cytotoxic agents that can be employed include aldesleukin, asparaginase, bleomycin sulfate, camptothecin, carboplatin, carmustine, cisplatin, cladribine, lyophilized cyclophosphamide, non-lyophilized cyclophosphamide, cytarabine, dacarbazine, dactinomycin, daunorubicin, diethylstilbestrol, doxorubicin, epoetin alfa, esperamycin, etidronate, etoposide, filgrastim, floxuridine, fludarabine phosphate, fluorouracil, goserelin, granisetron hydrochloride, idarubicin, ifosfamide, immune globulin, interferon alpha-2a, interferon alpha-2b, leucovorin calcium, leuprolide, levamisole, mechiorethamine, medroxyprogesterone, melphalan, methotrexate, mitomycin, mitoxantrone, octreotide, ondansetron hydrochloride, paclitaxel, pamidronate, disodium, pegaspargase, plicamycin, sargramostim, streptozocin, taxol, thiotepa, teniposide, vinblastine, vincristine, and the like.

In one embodiment, the mammal (e.g. a human patient) is treated with such agents and then given an autologous or allogenic bone marrow or stem cell transplant. In this strategy, bone marrow or mobilized peripheral blood is harvested before high dose chemotherapy or radiation and after any surgery to remove as much of a malignant tumor as possible from a patient. High doses of cytotoxic agents linked to agents capable of binding to REX-1 and/or chemotherapeutic agents and/or radiation are then administered, with patient recovery made possible by subsequent injection of the bone marrow or stem cells to reconstitute the patient's immune system, which was ablated by the intense doses of chemotherapy and/or radiation. This therapy has seen some success in the treatment of a variety of cancers, for example breast cancer and hematopoietic cancers, at cancer centers across the United States.

According to the invention, it may also be beneficial to increase rex-1 expression or REX-1 activity in cancer cells or tissues. Rex-1 expression or activity can be increased by administration of rex-1 nucleic acids or REX-1 protein. In some embodiments, a rex-1 expression cassette is administered that includes a nucleic acid encoding a REX-1 protein that is operably linked to expression control sequences (e.g. a promoter). In other embodiments, a therapeutically effective amount of REX-1 protein is administered. Administration of rex-1 nucleic acids or REX-1 protein can be localized to a tumor, organ or tissue. In other embodiments, administration of rex-1 nucleic acids or REX-1 protein can be systemic.

Nucleic Acids that Inhibit rex-1 RNA Functioning

Thus, in one embodiment, cancer can be treated by administering to a mammal a nucleic acid that can inhibit the functioning of a rex-1 RNA. Nucleic acids that can inhibit the function of a rex-1 RNA can be generated from coding and non-coding regions of the rex-1 gene. However, nucleic acids that can inhibit the function of rex-1 RNA are often selected to be complementary to sequences near the 5' end of the coding region. Hence, in some embodiments, the nucleic acid that can inhibit the functioning of rex-1 RNA can be complementary to sequences near the 5' end of SEQ ID NO:2. In other embodiments, nucleic acids that can inhibit the function of a rex-1 RNA having SEQ ID NO:2 can be complementary to rex-1 RNAs from other species (e.g., mouse, rat, cat, dog, goat, pig or a monkey rex-1 RNA).

A nucleic acid that can inhibit the functioning of rex-1 RNA need not be 100% complementary to a selected region of SEQ ID NO:2. Instead, some variability the sequence of the nucleic acid that can inhibit the functioning of rex-1 RNA is permitted. For example, a nucleic acid that can inhibit the functioning of a human rex-1 RNA can be complementary to a nucleic acid encoding a mouse or rat rex-1 gene product. Nucleic acids encoding the mouse rex-1 gene product, for example, can be found in the NCBI database at GenBank Accession No. NT 039460 and NM 009556; a mouse REX-1 polypeptide sequence has GenBank Accession No. NP 0033582. Sequences of other species of rex-1 are available in the database provided by the National Center for Biotechnology Information.

Moreover, nucleic acids that can hybridize under moderately or highly stringent hybridization conditions are sufficiently complementary to inhibit the functioning of rex-1 RNA and can be utilized in the compositions of the invention. Generally, stringent hybridization conditions are selected to be about 5° C. lower than the thermal melting point ($T_m$) for the specific sequence at a defined ionic strength and pH. However, stringent conditions encompass temperatures in the range of about 1° C. to about 20° C. lower than the thermal pointing point of the selected sequence, depending upon the desired degree of stringency as otherwise qualified herein. In some embodiments, the nucleic acids that can inhibit the functioning of rex-1 RNA can hybridize to a rex-1 RNA under physiological conditions, for example, physiological temperatures and salt concentrations.

Precise complementarity is therefore not required for successful duplex formation between a nucleic acid that can inhibit a rex-1 RNA and the complementary coding sequence of a rex-1 RNA. Inhibitory nucleic acid molecules that comprise, for example, 2, 3, 4, or 5 or more stretches of contiguous nucleotides that are precisely complementary to a rex-1 coding sequence, each separated by a stretch of contiguous nucleotides that are not complementary to adjacent rex-1 coding sequences, can inhibit the function of rex-1 mRNA. In general, each stretch of contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of a nucleic acid hybridized to a sense nucleic acid to estimate the degree of mismatching that will be tolerated between a particular nucleic acid for inhibiting expression of a particular rex-1 RNA.

In some embodiments a nucleic acid that can inhibit the function of an endogenous rex-1 RNA is an anti-sense oligonucleotide. The anti-sense oligonucleotide can be complementary to at least a portion of the coding sequence of a gene comprising SEQ ID NO:2. Such anti-sense oligonucleotides are generally at least six nucleotides in length, but can be about 8, 12, 15, 20, 25, 30, 35, 40, 45, or 50 nucleotides long. Longer oligonucleotides can also be used. Rex-1 anti-sense oligonucleotides can be provided in a DNA construct, or expression cassette and introduced into any cell, for example, into cells that express rex-1, such as stem cells, cancer cells or immortalized cell lines.

In one embodiment of the invention, expression of a rex-1 gene is decreased using a ribozyme. A ribozyme is an RNA molecule with catalytic activity. See, e.g., Cech, 1987, Science 236: 1532-1539; Cech, 1990, Ann. Rev. Biochem. 59:543-568; Cech, 1992, Curr. Opin. Struct. Biol. 2: 605-609; Couture and Stinchcomb, 1996, Trends Genet. 12: 510-515. Ribozymes can be used to inhibit gene function by cleaving an RNA sequence, as is known in the art (see, e.g., Haseloff et al., U.S. Pat. No. 5,641,673).

Nucleic acids complementary to SEQ ID NO:2 can be used to generate ribozymes that will specifically bind to mRNA transcribed from a rex-1 gene. Methods of designing and constructing ribozymes that can cleave other RNA molecules in trans in a highly sequence specific manner have been developed and described in the art (see Haseloff et al. (1988), Nature 334:585-591). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201). The target sequence can be a segment of about 10, 12, 15, 20, or 50 contiguous nucleotides selected from a nucleotide sequence having SEQ ID NO:2. Longer complementary sequences can be used to increase the affinity of the hybridization sequence for the target. The hybridizing and cleavage regions of the ribozyme can be integrally related; thus, upon hybridizing to the target RNA through the complementary regions, the catalytic region of the ribozyme can cleave the target.

RNA interference (RNAi) involves post-transcriptional gene silencing (PTGS) induced by the direct introduction of dsRNA. Small interfering RNAs (siRNAs) are generally 21-23 nucleotide dsRNAs that mediate post-transcriptional gene silencing. Introduction of siRNAs can induce post-transcriptional gene silencing in mammalian cells. siRNAs can also be produced in vivo by cleavage of dsRNA introduced directly or via a transgene or virus. Amplification by an RNA-dependent RNA polymerase may occur in some organisms. siRNAs are incorporated into the RNA-induced silencing complex, guiding the complex to the homologous endogenous mRNA where the complex cleaves the transcript.

Rules for designing siRNAs are available. See, e.g., Elbashir S M, Harborth J, Lendeckel W, Yalcin A, Weber K, Tuschl T (2001). Duplexes of 21-nucleotide RNAs mediate RNA interference in mammalian cell culture. Nature 411: 494-498; J. Harborth, S. M. Elbashir, K. Vandenburgh, H. Manninga, S. A. Scaringe, K. Weber and T. Tuschl (2003). Sequence, chemical, and structural variation of small interfering RNAs and short hairpin RNAs and the effect on mammalian gene silencing, *Antisense Nucleic Acid Drug Dev.* 13: 83-106.

Thus, an effective siRNA can be made by selecting target sites within SEQ ID NO:2 that begin with AA, that have 3' UU overhangs for both the sense and antisense siRNA strands, and that have an approximate 50% G/C content. For example, a siRNA of the invention can have one of the following sequences:

```
AAAUAGCAGAGUGCUUCGCGGUU     (SEQ ID NO: 3)

AAUGGUGUGAUCUCAGCUCACUU     (SEQ ID NO: 4)

AAACCCACCCCACUCACCGCCUCUU   (SEQ ID NO: 5)
```

Nucleic acids that can decrease rex-1 expression or translation can hybridize to a nucleic acid comprising SEQ ID NO:2 under physiological conditions. In other embodiments, these nucleic acids can hybridize to a nucleic acid comprising SEQ ID NO:2 under stringent hybridization conditions. Examples of nucleic acids that can modulate the expression or translation of a REX-1 polypeptide include a siRNA that consists essentially of a double-stranded RNA with any one of SEQ ID NO:3, 4 or 5.

In another embodiment, the invention provides oligonucleotides that can modulate rex-1 expression because those oligonucleotides bind to REX-1 polypeptide and divert or inhibit the REX-1 from acting as a transcription factor. While REX-1 is bound to an oligonucleotide it cannot operate on a gene that would normally be under its control. An oligonucleotide that binds to REX-1 can include the sequence CCAT-NTTNNNA (SEQ ID NO:6), where N is any nucleotide (A, C, G or T).

Identifying Anti-Cancer Agents

The invention also provides methods for identifying an anti-cancer agent. These methods are based on the observation provided herein that rex-1 is expressed at different levels in cancer cells than in normal cells of the same cell type. Thus, the invention provides methods for identifying agents that can modulate rex-1 expression or REX-1 protein activity in cancer cells.

In one embodiment, the method involves providing a cancer cell whose rex-1 expression is higher than in normal cells of the same cell type, contacting the cancer cell with a test agent, and observing whether rex-1 expression decreases after exposure to a test agent. In this embodiment, sustained expression of rex-1 after exposure to a test agent is an indicator of a cancerous phenotype that has not been altered by the test agent. Agents that can reduce rex-1 expression in cancer cells that over-express REX-1 are good anti-cancer candidates.

Examples of cancerous cells that express rex-1 include MDA-MB-468 breast cancer cells. Methods for detecting rex-1 expression include nucleic acid amplification and immunoassays and are described in more detail below.

In another embodiment, the method involves providing a cancer cell whose rex-1 expression is lower than in normal cells of the same cell type, contacting the cancer cell with a test agent, and observing whether rex-1 expression increases after exposure to a test agent. In this embodiment, sustained expression of rex-1 after exposure to a test agent is an indicator of a cancerous phenotype that has been altered by the test agent. Thus, agents that can increase rex-1 expression in cancer cells lacking REX-1 are good anti-cancer candidates.

Examples of cancerous cells that under-express rex-1 include renal carcinoma cells. Methods for detecting rex-1 expression include nucleic acid amplification and immunoassays and are described in more detail below.

Assays for rex-1 Expression or REX-1 Polypeptides

Any assay available to one of skill in the art can be used for detecting rex-1 expression or REX-1 polypeptides including, for example, nucleic acid amplification assays and immunoassays.

Assays can be used to detect rex-1 expression or REX-1 polypeptides in test samples obtained from a variety of sources including, for example, biopsies, blood, lymph, tissues, and other biological samples from a mammal. In some embodiments, the test sample is a tissue sample, for example, a tissue sample suspected of having cancer cells. Evaluation of such samples from mammalian subjects permits detection of cancerous cells.

In one embodiment, nucleic acid amplification is used to detect rex-1 expression. Any procedure that amplifies RNA can be used, for example, reverse transcription-polymerase chain reaction (RT-PCR) assays, strand displacement amplification and other amplification procedures. Strand displacement amplification can be used as described in Walker et al (1992) Nucl. Acids Res. 20, 1691-1696. The term "polymerase chain reaction" ("PCR") refers to the method of K. B. Mullis U.S. Pat. Nos. 4,683,195; 4,683,202; and 4,965,188, hereby incorporated by reference, which describe a method for increasing the concentration of target nucleic acid in a mixture of genomic DNA or other DNA or RNA without cloning or purification.

The steps involved in PCR nucleic acid amplification method are described in more detail below. For ease of discussion, the nucleic acid to be amplified is described as being double-stranded. However, the process is equally useful for amplifying a single-stranded nucleic acid, such as a rex-1 mRNA. In the amplification of a single-stranded nucleic acid, the first step involves the synthesis of a complementary strand, for example, by reverse transcription so that two complementary target strands are available for amplification.

When PCR is performed on a rex-1 double-stranded DNA or cDNA target, two primers are employed, each primer hybridizing to a different DNA strand at opposite ends of the DNA target. For example, oligonucleotide primers are provided herein useful for amplifying a human rex-1 cDNA to yield a 302 bp rex-1 product or amplicon. These rex-1 primers for were designed to span two intron-exon boundaries and thereby prevent amplification of any contaminating genomic DNA. The forward primer (located in exon II) was 5'-gct gac cac cag cac act agg c-3' (SEQ ID NO:7) and the reverse primer (located in exon IV) was 5'-ttt ctg gtg tct tgt ctt tgc ccg-3' (SEQ ID NO:8).

The PCR process for amplifying a target nucleic acid consists of introducing a large excess of the two primers to a mixture that may contain the rex-1 expression target nucleic acid, followed by a precise sequence of thermal cycling in the presence of a nucleic acid polymerase. For PCR amplification, each of the two primers is complementary to a distinct region in one of the two strands of the double stranded target sequence. Primers are selected so that they hybridize just outside the region of interest to be amplified and so that, upon primer extension, one primer will be extended towards the hybridization site of a second primer hybridized on the opposite target strand.

To effect amplification, the nucleic acid that may contain the rex-1 cDNA target is denatured to open up double-stranded target sites and the temperature is lowered so that the primers anneal to their complementary sequences within the target molecule. Following annealing, the primers are extended with a polymerase. Such primer extension forms a new pair of complementary strands that likely have different ends than the original target. Such complementary strands can hybridize together to form an "amplicon" that can also be a target for amplification. The steps of denaturation, primer annealing and primer extension can be repeated many times. Each round of denaturation, annealing and extension constitutes one "cycle." There can be numerous cycles, and the amount of amplified DNA produced increases with the number of cycles. Hence, to obtain a high concentration of an amplified target (rex-1) nucleic acid, many cycles are performed.

The following steps are generally employed during nucleic acid amplification with the inhibitors of the invention:

(a) Each target nucleic acid strand is contacted with four different nucleoside triphosphates and one oligonucleotide primer, wherein each primer is selected to be substantially complementary to a portion the nucleic acid strand to be amplified (rex-1), such that the extension product synthesized from one primer, when it is separated from its complement, can serve as a template for synthesis of the extension product of the other primer. To promote the proper annealing of primer(s) and the nucleic acid strands to be amplified, a selected primer-hybridization temperature is used that allows hybridization of each primer to a complementary nucleic acid strand. The inhibitors of the invention can be added or included in this melting/annealing reaction.

(b) After primer annealing, a nucleic acid polymerase is used for primer extension. The nucleic acid polymerase incorporates the nucleoside triphosphates into a growing nucleic acid strand to form a new strand that is complementary to the template strand hybridized by the primer. In general, this primer extension reaction is performed at a temperature and for a time effective to promote the activity of the nucleic acid enzyme and to synthesize a "full length" complementary nucleic acid strand that extends into and through a complete second primer binding site. However, the temperature is not so high as to separate each extension product from its nucleic acid template strand. The polymerase may be added after the first melting/annealing reaction.

(c) The mixture from step (b) is then heated for a time and at a temperature sufficient to separate the primer extension products from their complementary templates. The temperature chosen is not so high as to irreversibly denature the nucleic acid polymerase present in the mixture.

(d) The mixture from (c) is cooled for a time and at a temperature effective to promote hybridization of a primer to each of the single-stranded molecules produced in step (b).

(e) The mixture from step (d) is maintained at a temperature and for a time sufficient to promote primer extension by the polymerase to produce a "full length" extension product. The temperature used is not so high as to separate each extension product from the complementary strand template. Steps (c)-(e) are repeated until the desired level of amplification is obtained.

The present invention therefore includes a method for detecting rex-1 expression that involves nucleic acid amplification, wherein a sample containing a target nucleic acid that is to be amplified is mixed with 1) primers that are complementary to sequences within the rex-1 target sequence to be amplified, 2) a thermostable polymerase, and 3) four different nucleoside triphosphates. The normal steps of nucleic acid amplification are then followed—melting, annealing and synthesis—by thermal cycling of the mixture.

In some embodiments, an immunoassay is employed. Such an immunoassay can involve any immunological assay method available to one of skill in the art. Examples of immunoassays include immunohistochemistry, radioimmunoassays, competitive binding assays, sandwich assays, and immunoprecipitation assays. Antibodies or binding entities of the invention can be combined or attached to a detectable label as described herein. The choice of label used will vary depending upon the application and can be made by one skilled in the art.

In the practice of this invention the detectable label may be an enzyme such as horseradish peroxidase or alkaline phosphatase, a paramagnetic ion, a chelate of a paramagnetic ion, biotin, a fluorophore, a chromophore, a heavy metal, a chelate of a heavy metal, a compound or element which is opaque to X-rays, a radioisotope, or a chelate of a radioisotope.

Radioisotopes useful as detectable labels include such isotopes as iodine-123, iodine-125, iodine-128, iodine-131, or a chelated metal ion of chromium-51, cobalt-57, gallium-67, indium-111, indium-113m, mercury-197, selenium-75, thallium-201, technetium-99m, lead-203, strontium-85, strontium-87, gallium-68, samarium-153, europium-157, ytterbium-169, zinc-62, or rhenium-188.

Paramagnetic ions useful as detectable label s include such ions as chromium (III), manganese (II), iron (III), iron (II), cobalt (II), nickel (II), copper (II), praseodymium (III), neodymium (III), samarium (III), gadolinium (III), terbium (III), dysprosium (III), holmium (III), erbium (III), or ytterbium (III).

Radioimmunoassays typically use radioactivity in the measurement of complexes between binding entities (e.g. antibodies) and REX-1 polypeptides. In such a method, the binding entity is radio-labeled. The binding entity is reacted with unlabeled REX-1 polypeptides. The radio-labeled complex is then separated from unbound material, for example, by precipitation followed by centrifugation. Once the complex between the radio-labeled binding entity and the REX-1 polypeptide is separated from the unbound material, the amount of complex is quantified either by measuring the radiation directly or by observing the effect that the radiolabel has on a fluorescent molecule, such as dephenyloxazole (DPO). The latter approach requires less radioactivity and is more sensitive. This approach, termed scintillation, measures the fluorescent transmission of a dye solution that has been excited by a radiolabel, such as $^3$H or $^{32}$P. The extent of binding is determined by measuring the intensity of the fluorescence released from the fluorescent particles. This method, termed scintillation proximity assay (SPA), has the advantage of being able to measure binding entity complexes formed in situ without the need for washing off unbound radioactive binding entity.

Competitive binding assays rely on the ability of a labeled standard to compete with the test sample analyte for binding with a limited amount of binding entity. The labeled standard may be a REX-1 polypeptide, variant or derivative thereof.

The amount of test sample is inversely proportional to the amount of standard that becomes bound to the binding entities. To facilitate determining the amount of standard that becomes bound, the binding entities employed are generally made insoluble either before or after the competition. This is done so that the standard and analyte that are bound to the binding entities may be conveniently separated from the standard and analyte that remain unbound.

Sandwich assays involve the use of two binding entities, each capable of binding to a different immunogenic portion, or epitope, of the product to be detected. In a sandwich assay, the test sample analyte is bound by a first binding entity which is immobilized on a solid support, and thereafter a second binding entity binds to the analyte, thus forming an insoluble three part complex (David & Greene, U.S. Pat. No. 4,376,110). The second binding entity may itself by labeled with a detectable moiety (direct sandwich assays) or may be measured using a third binding entity that binds the second bonding entity and is labeled with a detectable moiety (indirect sandwich assay). For example, one type of sandwich assay is an ELISA assay, in which case the detectable moiety is an enzyme.

Typically, sandwich assays include "forward" assays in which the binding entity bound to the solid phase is first contacted with the sample being tested to extract the REX-1 polypeptides or cells expressing REX-1 polypeptides from the sample by formation of a binary solid phase complex between the immobilized binding entity and the REX-1 polypeptides. After a suitable incubation period, the solid support is washed to remove unbound fluid sample, including unreacted REX-1 polypeptide, if any. The solid support is then contacted with the solution containing an unknown quantity of labeled binding entity (which functions as a label or reporter molecule). After a second incubation period to permit the labeled binding entity to react with the complex between the immobilized binding entity and the REX-1 polypeptide, the solid support is washed a second time to remove the unreacted labeled binding entity. This type of forward sandwich assay may be a simple "yes/no" assay to determine whether a REX-1 polypeptide is present in the test sample.

Other types of sandwich assays that may be used include the so-called "simultaneous" and "reverse" assays. A simultaneous assay involves a single incubation step wherein the labeled and unlabeled binding entities are, at the same time, both exposed to the sample being tested. The unlabeled binding entity is immobilized onto a solid support, while the labeled binding entity is free in solution with the test sample. After the incubation is completed, the solid support is washed to remove unreacted sample and uncomplexed labeled binding entity. The presence of labeled binding entity associated with the solid support is then determined as it would be in a conventional "forward" sandwich assay.

In a "reverse" assay, stepwise addition is utilized, first of a solution of labeled binding entity to a test sample, followed by incubation, and then later by addition of an unlabeled binding entity bound to a solid support. After a second incubation, the solid phase is washed in conventional fashion to free it of the residue of the sample being tested and the solution of unreacted labeled binding entity. The determination of labeled binding entity associated with a solid support is then determined as in the "simultaneous" and "forward" assays.

In addition to their diagnostic utility, the binding entities of the present invention are useful for monitoring the progression of cancer in a subject by examining the levels of REX-1 polypeptides in tissues, biopsies, cells or other samples over time. Changes in the levels of REX-1 polypeptides or rex-1 expression over time may indicate further progression of the cancer in the subject.

Anti-REX-1 Antibodies and Binding Entities

The invention also provides antibodies and binding entities that preferentially bind to REX-1 protein. The anti-REX-1 antibodies and binding entities of the invention can bind to any epitope on the REX-1 protein. However, in some embodiments, the anti-REX-1 antibodies bind to a peptide having amino acid sequence SNNLKAHILTHANTNKNEQEGK (SEQ ID NO:9). Such anti-REX-1 antibodies are useful for detecting REX-1 both in vitro and in vivo. For example, in some embodiments, the anti-REX-1 antibodies can be used to detect REX-1 in tissue samples, various cell types and in isolated cell preparations. In other embodiments, the anti-REX-1 antibodies can be used to detect cancer by in vivo imaging procedures using live patients. Observing aberrant levels of REX-1 is indicative of the presence of stem cells or cancerous cells.

The invention therefore provides antibodies made by available procedures that can bind REX-1. The binding domains of such antibodies, for example, the CDR regions of these antibodies, can be transferred into or utilized with any convenient binding entity backbone.

Antibody molecules belong to a family of plasma proteins called immunoglobulins, whose basic building block, the immunoglobulin fold or domain, is used in various forms in many molecules of the immune system and other biological recognition systems. A standard antibody is a tetrameric structure consisting of two identical immunoglobulin heavy chains and two identical light chains and has a molecular weight of about 150,000 daltons.

The heavy and light chains of an antibody consist of different domains. Each light chain has one variable domain (VL) and one constant domain (CL), while each heavy chain has one variable domain (VH) and three or four constant domains (CH). See, e.g., Alzari, P. N., Lascombe, M.-B. & Poljak, R. J. (1988) *Three-dimensional structure of antibodies*. Annu. Rev. Immunol. 6, 555-580. Each domain, consisting of about 10 amino acid residues, is folded into a characteristic β-sandwich structure formed from two β-sheets packed against each other, the immunoglobulin fold. The VH and VL domains each have three complementarity determining regions (CDR1-3) that are loops, or turns, connecting β-strands at one end of the domains. The variable regions of both the light and heavy chains generally contribute to antigen specificity, although the contribution of the individual chains to specificity is not always equal. Antibody molecules have evolved to bind to a large number of molecules by using six randomized loops (CDRs).

Immunoglobulins can be assigned to different classes depending on the amino acid sequences of the constant domain of their heavy chains. There are at least five (5) major classes of immunoglobulins: IgA, IgD, IgE, IgG and IgM. Several of these may be further divided into subclasses (isotypes), for example, IgG-1, IgG-2, IgG-3 and IgG-4; IgA-1 and IgA-2. The heavy chain constant domains that correspond to the IgA, IgD, IgE, IgG and IgM classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies, refers to the fact that certain portions of variable domains differ extensively in sequence from one antibody to the next. The variable domains are for binding and determine the specificity of each particular antibody for its particular antigen. However, the variability is not evenly distributed through the variable domains of antibodies. Instead, the variability is concentrated in three segments called complementarity determining regions (CDRs), also known as hypervariable regions in both the light chain and the heavy chain variable domains.

The more highly conserved portions of variable domains are called framework (FR) regions. The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from another chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific REX-1 polypeptide or derivative thereof.

Moreover, the binding regions, or CDR, of antibodies can be placed within the backbone of any convenient binding entity polypeptide. In preferred embodiments, in the context of methods described herein, an antibody, binding entity or fragment thereof is used that is immunospecific for REX-1, as well as the variants and derivatives thereof.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called Fab fragments, each with a single antigen binding site, and a residual Fc fragment. Fab fragments thus have an intact light chain and a portion of one heavy chain. Pepsin treatment yields an F(ab')$_2$ fragment that has two antigen binding fragments that are capable of cross-linking antigen, and a residual fragment that is termed a pFc' fragment. Fab' fragments are obtained after reduction of a pepsin digested antibody, and consist of an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site. As used herein, "functional fragment" with respect to antibodies, refers to Fv, F(ab) and F(ab')$_2$ fragments.

Additional fragments can include diabodies, linear antibodies, single-chain antibody molecules, and multispecific antibodies formed from antibody fragments. Single chain antibodies are genetically engineered molecules containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies, vol. 113, Rosenburg and Moore eds. Springer-Verlag, N.Y., pp. 269-315 (1994).

The term "diabodies" refers to a small antibody fragments with two antigen-binding sites, where the fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad. Sci. USA 90: 6444-6448 (1993).

Antibody fragments contemplated by the invention are therefore not full-length antibodies. However, such antibody fragments can have similar or improved immunological properties relative to a full-length antibody. Such antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more.

In general, an antibody fragment of the invention can have any upper size limit so long as it is has similar or improved immunological properties relative to an antibody that binds with specificity to a REX-1 polypeptide. For example, smaller binding entities and light chain antibody fragments can have less than about 200 amino acids, less than about 175 amino acids, less than about 150 amino acids, or less than about 120 amino acids if the antibody fragment is related to a light chain antibody subunit. Moreover, larger binding entities and heavy chain antibody fragments can have less than about 425 amino acids, less than about 400 amino acids, less than about 375 amino acids, less than about 350 amino acids, less than about 325 amino acids or less than about 300 amino acids if the antibody fragment is related to a heavy chain antibody subunit.

Antibodies directed against REX-1 can be made by any available procedure. Methods for the preparation of polyclonal antibodies are available to those skilled in the art. See, for example, Green, et al., Production of Polyclonal Antisera, in: *Immunochemical Protocols* (Manson, ed.), pages 1-5 (Humana Press); Coligan, et al., Production of Polyclonal Antisera in Rabbits, Rats Mice and Hamsters, in: *Current Protocols in Immunology*, section 2.4.1 (1992), which are hereby incorporated by reference.

Monoclonal antibodies can also be employed in the invention. The term "monoclonal antibody" as used herein refers to an antibody obtained from a population of substantially homogeneous antibodies. In other words, the individual antibodies comprising the population are identical except for occasional naturally occurring mutations in some antibodies that may be present in minor amounts. Monoclonal antibodies are highly specific, being directed against a single antigenic site. Furthermore, in contrast to polyclonal antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates that the antibody is obtained from a substantially homogeneous population of antibodies, and is not to be construed as requiring production of the antibody by any particular method.

The monoclonal antibodies herein specifically include "chimeric" antibodies in which a portion of the heavy and/or light chain is identical or homologous to corresponding sequences in antibodies derived from a particular species or belonging to a particular antibody class or subclass, while the remainder of the chain(s) is identical or homologous to corresponding sequences in antibodies derived from another species or belonging to another antibody class or subclass. Fragments of such antibodies can also be used, so long as they exhibit the desired biological activity. See U.S. Pat. No. 4,816,567; Morrison et al. Proc. Natl. Acad. Sci. 81, 6851-55 (1984).

The preparation of monoclonal antibodies likewise is conventional. See, for example, Kohler & Milstein, Nature, 256: 495 (1975); Coligan, et al., sections 2.5.1-2.6.7; and Harlow, et al., in: *Antibodies: A Laboratory Manual*, page 726 (Cold Spring Harbor Pub. (1988)), which are hereby incorporated by reference. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG), in: *Methods in Molecular Biology*, Vol. 10, pages 79-104 (Humana Press (1992).

Methods of in vitro and in vivo manipulation of antibodies are available to those skilled in the art. For example, the monoclonal antibodies to be used in accordance with the present invention may be made by the hybridoma method as described above or may be made by recombinant methods, e.g., as described in U.S. Pat. No. 4,816,567. Monoclonal antibodies for use with the present invention may also be isolated from phage antibody libraries using the techniques described in Clackson et al. Nature 352: 624-628 (1991), as well as in Marks et al., J. Mol. Biol. 222: 581-597 (1991).

Methods of making antibody fragments are also known in the art (see for example, Harlow and Lane, *Antibodies: A Laboratory Manual*, Cold Spring Harbor Laboratory, New York, (1988), incorporated herein by reference). Antibody fragments of the present invention can be prepared by proteolytic hydrolysis of the antibody or by expression of nucleic acids encoding the antibody fragment in a suitable host. Antibody fragments can be obtained by pepsin or papain digestion of whole antibodies conventional methods. For example, antibody fragments can be produced by enzymatic cleavage of antibodies with pepsin to provide a 5S fragment described as F(ab')$_2$. This fragment can be further cleaved using a thiol reducing agent, and optionally using a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. These methods are described, for example, in U.S. Pat. No. 4,036,945 and No. 4,331,647, and references contained therein. These patents are hereby incorporated by reference in their entireties.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., Science 242:423-426 (1988); Ladner, et al, U.S. Pat. No. 4,946,778; and Pack, et al., *Bio/Technology* 11:1271-77 (1993).

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., Nature 321, 522-525 (1986); Reichmann et al., Nature 332, 323-329 (1988); Presta, Curr. Op. Struct. Biol. 2, 593-596 (1992); Holmes, et al., J. Immunol., 158:2192-2201 (1997) and Vaswani, et al., Annals Allergy, Asthma & Immunol., 81:105-115 (1998).

While standardized procedures are available to generate antibodies, the size of antibodies, the multi-stranded structure of antibodies and the complexity of six binding loops present in antibodies constitute a hurdle to the improvement and the manufacture of large quantities of antibodies. Hence, the invention further contemplates using binding entities, which comprise polypeptides that can recognize and bind to a REX-1 polypeptide.

A number of proteins can serve as protein scaffolds to which binding domains for REX-1 can be attached and thereby form a suitable binding entity. The binding domains bind or interact with REX-1 while the protein scaffold merely holds and stabilizes the binding domains so that they can bind. A number of protein scaffolds can be used. For example, phage capsid proteins can be used. See Review in Clackson & Wells, Trends Biotechnol. 12:173-184 (1994). Phage capsid proteins have been used as scaffolds for displaying random peptide sequences, including bovine pancreatic trypsin inhibitor (Roberts et al., PNAS 89:2429-2433 (1992)), human growth hormone (Lowman et al., Biochemistry 30:10832-10838 (1991)), Venturini et al., Protein Peptide Letters 1:70-75 (1994)), and the IgG binding domain of *Streptococcus* (O'Neil et al., Techniques in Protein Chemistry V (Crabb, L,. ed.) pp. 517-524, Academic Press, San Diego (1994)). These scaffolds have displayed a single randomized loop or region that can be modified to include binding domains for REX-1.

Researchers have also used the small 74 amino acid α-amylase inhibitor Tendamistat as a presentation scaffold on the filamentous phage M13. McConnell, S. J., & Hoess, R. H., J. Mol. Biol. 250:460-470 (1995). Tendamistat is a β-sheet protein from *Streptomyces tendae*. It has a number of features that make it an attractive scaffold for binding peptides, including its small size, stability, and the availability of high resolution NMR and X-ray structural data. The overall topology of Tendamistat is similar to that of an immunoglobulin domain, with two β-sheets connected by a series of loops. In contrast to immunoglobulin domains, the β-sheets of Tendamistat are held together with two rather than one disulfide bond, accounting for the considerable stability of the protein. The loops of Tendamistat can serve a similar function to the CDR loops found in immunoglobulins and can be easily randomized by in vitro mutagenesis. Tendamistat is derived from *Streptomyces tendae* and may be antigenic in humans. Hence, binding entities that employ Tendamistat are preferably employed in vitro.

Fibronectin type III domain has also been used as a protein scaffold to which binding entities can be attached. Fibronectin type III is part of a large subfamily (Fn3 family or s-type Ig family) of the immunoglobulin superfamily. Sequences, vectors and cloning procedures for using such a fibronectin type III domain as a protein scaffold for binding entities (e.g. CDR peptides) are provided, for example, in U.S. Patent Application Publication 20020019517. See also, Bork, P. & Doolittle, R. F. (1992) Proposed acquisition of an animal protein domain by bacteria. Proc. Natl. Acad. Sci. USA 89, 8990-8994; Jones, E. Y. (1993) The immunoglobulin superfamily Curr. Opinion Struct. Biol. 3, 846-852; Bork, P., Hom, L. & Sander, C. (1994) The immunoglobulin fold. Structural classification, sequence patterns and common core. J. Mol. Biol. 242, 309-320; Campbell, 1. D. & Spitzfaden, C. (1994) Building proteins with fibronectin type III modules Structure 2, 233-337; Harpez, Y. & Chothia, C. (1994).

In the immune system, specific antibodies are selected and amplified from a large library (affinity maturation). The combinatorial techniques employed in immune cells can be mimicked by mutagenesis and generation of combinatorial libraries of binding entities. Variant binding entities, antibody fragments and antibodies therefore can also be generated through display-type technologies. Such display-type technologies include, for example, phage display, retroviral display, ribosomal display, and other techniques. Techniques available in the art can be used for generating libraries of binding entities, for screening those libraries and the selected binding entities can be subjected to additional maturation, such as affinity maturation. Wright and Harris, supra., Hanes and Plucthau PNAS USA 94:4937-4942 (1997) (ribosomal display), Parmley and Smith Gene 73:305-318 (1988) (phage display), Scott TIBS 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH 10:80-84 (1992), and U.S. Pat. No. 5,733,743.

The invention therefore also provides methods of mutating antibodies, CDRs or binding domains to optimize their affinity, selectivity, binding strength and/or other desirable properties. A mutant binding domain refers to an amino acid sequence variant of a selected binding domain (e.g. a CDR). In general, one or more of the amino acid residues in the mutant binding domain is different from what is present in the reference binding domain. Such mutant antibodies necessarily have less than 100% sequence identity or similarity with the reference amino acid sequence. In general, mutant binding domains have at least 75% amino acid sequence identity or similarity with the amino acid sequence of the reference binding domain. Preferably, mutant binding domains have at least 80%, more preferably at least 85%, even more preferably at least 90%, and most preferably at least 95% amino acid sequence identity or similarity with the amino acid sequence of the reference binding domain.

For example, affinity maturation using phage display can be utilized as one method for generating mutant binding domains. Affinity maturation using phage display refers to a process described in Lowman et al., Biochemistry 30(45): 10832-10838 (1991), see also Hawkins et al., J. Mol. Biol. 254: 889-896 (1992). While not strictly limited to the following description, this process can be described briefly as involving mutation of several binding domains or antibody hypervariable regions at a number of different sites with the goal of generating all possible amino acid substitutions at each site. The binding domain mutants thus generated are displayed in a monovalent fashion from filamentous phage particles as fusion proteins. Fusions are generally made to the gene III product of M13. The phage expressing the various mutants can be cycled through several rounds of selection for the trait of interest, e.g. binding affinity or selectivity. The mutants of interest are isolated and sequenced. Such methods are described in more detail in U.S. Pat. No. 5,750,373, U.S. Pat. No. 6,290,957 and Cunningham, B. C. et al., EMBO J. 13(11), 2508-2515 (1994).

Therefore, in one embodiment, the invention provides methods of manipulating binding entity or antibody polypeptides or the nucleic acids encoding them to generate binding entities, antibodies and antibody fragments with improved binding properties that recognize REX-1.

Such methods of mutating portions of an existing binding entity or antibody involve fusing a nucleic acid encoding a polypeptide that encodes a binding domain for REX-1 to a nucleic acid encoding a phage coat protein to generate a recombinant nucleic acid encoding a fusion protein, mutating the recombinant nucleic acid encoding the fusion protein to generate a mutant nucleic acid encoding a mutant fusion protein, expressing the mutant fusion protein on the surface of a phage, and selecting phage that bind to REX-1.

Accordingly, the invention provides antibodies, antibody fragments, and binding entity polypeptides that can recognize and bind to a REX-1 polypeptide. The invention further provides methods of manipulating those antibodies, antibody fragments, and binding entity polypeptides to optimize their binding properties or other desirable properties (e.g., stability, size, ease of use).

Such antibodies, antibody fragments, and binding entity polypeptides can be modified to include a label or reporter molecule useful for detecting the presence of the antibody. The labeled antibody can then be used for detection of REX-1.

As used herein, a label or reporter molecule is any molecule that can be associated with an antibody, directly or indirectly, and that results in a measurable, detectable signal, either directly or indirectly. Many such labels can be incorporated into or coupled onto an antibody or binding entity are available to those of skill in the art. Examples of labels suitable for use with the antibodies and binding entities of the invention include radioactive isotopes, fluorescent molecules, phosphorescent molecules, enzymes, secondary antibodies, and ligands.

Examples of suitable fluorescent labels include fluorescein (FITC), 5, 6-carboxymethyl fluorescein, Texas Red™, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. In some embodiments, the fluorescent label is fluorescein (5-carboxyfluorescein-N-hydroxysuccinimide ester) or rhodamine (5,6-tetramethyl rhodamine). Fluorescent labels for combinatorial multicolor used in some embodiments include FITC and the cyanine dyes Cy3, Cy3.5, Cy5, Cy5.5 and Cy7. The absorption and emission maxima, respectively, for these fluors are: FITC (490 nm; 520 mm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Such fluorescent labels can be obtained from a variety of commercial sources, including Molecular Probes, Eugene. OR and Research Organics, Cleveland, OH.

Detection labels that are incorporated into an antibody or binding entity, such as biotin, can be subsequently detected using sensitive methods available in the art. For example, biotin can be detected using streptavidin-alkaline phosphatase conjugate (Tropix., Inc.) that binds to the biotin and subsequently can be detected by chemiluminescence of suitable substrates (for example, the chemiluminescent substrate CSPD: disodium, 3-(4-methoxyspiro-[1,2,-dioxetane-3-2'-(5'-chloro)tricyclo [3.3.1.1.sup.3,7]decane]-4-yl) phenyl phosphate; Tropix, Inc.).

Molecules that combine two or more of these reporter molecules or detection labels can also be used in the invention. Any of the known detection labels can be used with the disclosed antibodies, antibody fragments, binding entities, and methods. Methods for detecting and measuring signals generated by detection labels are also available to those of skill in the art. For example, radioactive isotopes can be detected by scintillation counting or direct visualization; fluorescent molecules can be detected with fluorescent spectrophotometers; phosphorescent molecules can be detected with a scanner or spectrophotometer, or directly visualized with a camera; enzymes can be detected by visualization of the product of a reaction catalyzed by the enzyme. Such methods can be used directly in methods for detecting REX-1.

Expression of rex-1 Sense and Anti-Sense Nucleic Acids

The invention is directed to expression of rex-1 sense and anti-sense nucleic acids, including wild type rex-1 and nucleic acids that can decrease rex-1 expression or translation.

The present invention provides isolated nucleic acid segments that encode REX-1 proteins. An example of such a REX-1 protein is a protein with SEQ ID NO:1. A nucleic acid segment of the invention can also include mutations of the sequence listed in SEQ ID NO:2 that encode the same amino acids due to the degeneracy of the genetic code. For example, the amino acid threonine is encoded by ACU, ACC, ACA and ACG. It is intended that the invention includes all variations of the nucleic acid segments of SEQ ID NO:2 that encode the same amino acids. Such mutations are known in the art (Watson et al, Molecular Biology of the Gene, Benjamin Cummings 1987).

Mutations also include alteration of a nucleic acid segment to encode REX-1 proteins having conservative amino acid changes. Such amino acid changes are exemplified by the following five groups which contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur containing: Methionine (M), Cysteine (C); Basic: Arginine (R), Lysine (K), Histidine (H); Acidic: Aspartic acid (D), Glutamic acid (E), Asparagine (N), Glutamine (Q). Thus, the genes and nucleotide sequences of the invention include both the naturally occurring sequences as well as mutant forms.

The invention also provides an expression cassette which contains a DNA sequence capable of directing expression of a particular nucleic acid segment of the invention either in vitro or in a host cell. An example of such a nucleic acid segment is that having SEQ ID NO:2, or nucleic acid sequences encoding the same amino acid sequence as SEQ ID NO:1 due to the degeneracy of the genetic code, or conservative mutations thereof. The expression cassette is an isolatable unit such that the expression cassette may be in linear form and functional during in vitro transcription and translation assays. The materials and procedures to conduct these assays are commercially available from Promega Corp. (Madison, Wis.). For example, an in vitro transcript may be produced by placing a nucleic acid sequence under the control of a T7 promoter and then using T7 RNA polymerase to produce an in vitro transcript. This transcript may then be translated in vitro through use of a rabbit reticulocyte lysate. Alternatively, the expression cassette can be incorporated into a vector allowing for replication and amplification of the expression cassette within a host cell or also in vitro transcription and translation of a nucleic acid sequence.

Such an expression cassette may contain one or a plurality of restriction sites allowing for placement of the nucleic acid segment under the regulation of a regulatory sequence. The expression cassette can also contain a termination signal operably linked to the nucleic acid segment as well as regulatory sequences required for proper translation of the nucleic acid segment. The expression cassette containing the nucleic acid segment may be chimeric, meaning that at least one of its components is heterologous with respect to at least one of its other components. The expression cassette may also be one which is naturally occurring but has been obtained in a recombinant form useful for heterologous expression. Expression of the nucleic acid segment in the expression cassette may be under the control of a constitutive promoter or an inducible promoter which initiates transcription only when the host cell is exposed to some particular external stimulus.

The expression cassette may include in the 5'-3' direction of transcription, a transcriptional and translational initiation region, a nucleic acid segment and a transcriptional and translational termination region functional in vivo and/or in vitro. The termination region may be native with the transcriptional initiation region, may be native with the nucleic acid segment, or may be derived from another source.

The regulatory sequence can be a nucleic acid sequence located upstream (5' non-coding sequences), within, or downstream (3' non-coding sequences) of a coding sequence, and which influences the transcription, RNA processing or stability, or translation of the associated coding sequence. Regulatory sequences can include, but are not limited to, enhancers, promoters, repressor binding sites, translation leader sequences, introns, and polyadenylation signal sequences. They may include natural and synthetic sequences as well as sequences which may be a combination of synthetic and natural sequences. While regulatory sequences are not limited to promoters, some useful regulatory sequences include constitutive promoters, inducible promoters, regulated promoters, tissue-specific promoters, viral promoters and synthetic promoters.

A promoter is a nucleotide sequence which controls the expression of the coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be derived entirely from a native gene, or be composed of different elements derived from different promoters found in nature, or even be comprised of synthetic DNA segments. A promoter may contain DNA sequences that are involved in the binding of protein factors which control the effectiveness of transcription initiation in response to physiological or developmental conditions. A promoter may also include a minimal promoter plus a regulatory element or elements that are capable of controlling the expression of a coding sequence or functional RNA. This type of promoter sequence consists of proximal and more distal elements, the latter elements are often referred to as enhancers. The promoter may also be inducible.

An enhancer is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects.

The expression cassette can contain a 5' non-coding sequence which is a nucleotide sequence located 5' (upstream) to the coding sequence. It is present in the fully processed mRNA upstream of the initiation codon and may affect processing of the primary transcript to mRNA, stability of the mRNA or translation efficiency.

The expression cassette may also contain a 3' non-coding sequence which is a nucleotide sequence located 3' (downstream) to a coding sequence and includes polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

A nucleic acid segment of the invention may be contained within a vector. A vector may include, but is not limited to, any plasmid, phagemid, F-factor, virus, cosmid, or phage in double or single stranded linear or circular form which may or may not be self transmissible or mobilizable. The vector can also transform a prokaryotic or eukaryotic host either by integration into the cellular genome or exist extra chromosomally (e.g. autonomous replicating plasmid with an origin of replication).

Preferably the nucleic acid in the vector is under the control of, and operably linked to, an appropriate promoter or other regulatory element for transcription in vitro or in a host cell such as a eukaryotic cell or microbe, e.g. bacteria. The vector may be a bi-functional expression vector which functions in multiple hosts. In the case of genomic DNA, this may contain its own promoter or other regulatory elements and in the case of cDNA this may be under the control of a promoter or other regulatory sequences for expression in a host cell.

Shuttle vectors are included and are DNA vehicles capable, naturally or by design, of replication in two different host organisms. The vector may also be a cloning vector which typically contains one or a small number of restriction endonuclease recognition sites at which foreign DNA sequences can be inserted in a determinable fashion. Such insertion can occur without loss of essential biological function of the cloning vector. A cloning vector may also contain a marker gene that is suitable for use in the identification and selection of cells transformed with the cloning vector. Examples of marker genes are tetracycline resistance or ampicillin resistance. Many cloning vectors are commercially available (Stratagene, New England Biolabs, Clonetech).

The nucleic acid segments of the invention may also be inserted into an expression vector. Typically an expression vector contains (1) prokaryotic DNA elements coding for a bacterial replication origin and an antibiotic resistance gene to provide for the amplification and selection of the expression vector in a bacterial host; (2) regulatory elements that control initiation of transcription such as a promoter; and (3) DNA elements that control the processing of transcripts such as introns, transcription termination/polyadenylation sequence.

Methods to introduce a nucleic acid segment into a vector are well known in the art (Sambrook et al., Molecular Cloning: A Laboratory Manual, 3rd edition, Cold Spring Harbor Press, Cold Spring Harbor, N.Y. (2001)). Briefly, a vector into which the nucleic acid segment is to be inserted is treated with one or more restriction enzymes (restriction endonuclease) to produce a linearized vector having a blunt end, a "sticky" end with a 5' or a 3' overhang, or any combination of the above. The vector may also be treated with a restriction enzyme and subsequently treated with another modifying enzyme, such as a polymerase, an exonuclease, a phosphatase or a kinase, to create a linearized vector that has characteristics useful for ligation of a nucleic acid segment into the vector. The nucleic acid segment that is to be inserted into the vector is treated with one or more restriction enzymes to create a linearized segment having a blunt end, a "sticky" end with a 5' or a 3' overhang, or any combination of the above. The nucleic acid segment may also be treated with a restriction enzyme and subsequently treated with another DNA modifying enzyme. Such DNA modifying enzymes include, but are not limited to, polymerase, exonuclease, phosphatase or a kinase, to create a nucleic acid segment that has characteristics useful for ligation of a nucleic acid segment into the vector. The treated vector and nucleic acid segment are then ligated together to form a construct containing a nucleic acid segment according to methods known in the art (Sambrook et al., Molecular Cloning: A Laboratory Manual, 3rd edition, Cold Spring Harbor Press, Cold Spring Harbor, N.Y. (2001)). Briefly, the treated nucleic acid fragment and the treated vector are combined in the presence of a suitable buffer and ligase. The mixture is then incubated under appropriate conditions to allow the ligase to ligate the nucleic acid fragment into the vector. It is preferred that the nucleic acid fragment and the vector each have complimentary "sticky" ends to increase ligation efficiency, as opposed to blunt-end ligation. It is more preferred that the vector and nucleic acid fragment are each treated with two different restriction enzymes to produce two different complimentary "sticky" ends. This allows for directional ligation of the nucleic acid fragment into the vector, increases ligation efficiency and avoids ligation of the ends of the vector to reform the vector without the inserted nucleic acid fragment.

The invention also provides a construct containing a vector and an expression cassette. The vector may be selected from, but not limited to, any vector described herein. Into this vector may be inserted an expression cassette containing the nucleic acid sequences of the invention through methods known in the art and previously described (Sambrook et al., Molecular Cloning: A Laboratory Manual, 3rd edition, Cold Spring Harbor Press, Cold Spring Harbor, N.Y. (2001)). In one embodiment, the regulatory sequences of the expression cassette may be derived from a source other than the vector into which the expression cassette is inserted. In another embodiment, a construct containing a vector and an expression cassette is formed upon insertion of a nucleic acid segment of the invention into a vector that itself contains regulatory sequences. Thus, an expression cassette is formed upon insertion of the nucleic acid segment into the vector. Vectors containing regulatory sequences are available commercially and methods for their use are known in the art (Clonetech, Promega, Stratagene).

The expression cassette, or a vector construct containing the expression cassette may be inserted into a cell. The expression cassette or vector construct may be carried episomally or integrated into the genome of the cell. A variety of techniques are available and known to those skilled in the art for introduction of constructs into a cellular host. Transformation of bacteria and many eukaryotic cells may be accomplished through use of polyethylene glycol, calcium chloride, viral infection, phage infection, electroporation and other methods known in the art.

The expression cassette or vector can also be administered to a tissue, for example, a tumor or cancerous tissue. Thus, for example, when a cancer is of a cancerous cell type where rex-1 is expressed at lower levels than in corresponding normal cells, rex-1 expression can be increased by administration of a rex-1 expression cassette or expression vector.

The present invention also provides for the production of a stem cell line that can overexpress rex-1. Such a cell line does not readily undergo differentiation. The overexpression of REX-1 can be transient, inducible or otherwise modulated by use of a promoter that responds to certain stimuli.

To create a stem cell line that can overexpress rex-1, a nucleic acid segment can be inserted into a germ line or stem cell using standard techniques of retroviral infection, microinjection, transfection, or microinjection into embryonic stem cells.

The present invention provides REX-1 polypeptides expressed through use of the expression cassettes and constructs described herein. Methods to purify the polypeptides include, but are not limited to, liquid chromatography, gel permeation chromatography, salt precipitation, immunopurification methods, affinity purification, and the like. Such methods are known in the art. These polypeptides can be used to identify REX-1 modulators. REX-1 polypeptides can also be administered to a mammal, for example, a human with cancer or other condition.

The following Examples further illustrate but are not intended to limit the invention.

EXAMPLE 1

Human rex-1 is a Transcription Factor Expressed in Certain Cancer Cells

Cell Culture

The following human carcinoma and leukemia cell lines were maintained as directed by the ATCC: breast cancer cells: MCF-7, MDA-MB-231, MDA-MB-453, MDA-MB-468, SK-BR3 and HS578T; prostate cancer cells: LnCAP; skin cancer cells: SCC-12, SCC-13; kidney cancer cells: SK-39; bladder cancer cells: HTB1, HT1376, HTB9; oral cavity (head and neck) cancer: SCC-4, SCC-9, SCC-25, SCC-15; leukemia cells: HL-60, NB4 and NTERA2 teratocarcinoma cells. Normal human mammary (HMEC); renal proximal tubule epithelial cells (RPTE); prostate epithelial cells (PrEC), keratinocytes (NHEK) and lung (NHBE, SAEC) epithelial cells were grown as directed by the supplier (Cambrex, Walkersville, Md.). Normal human keratinocytes were also purchased from Cascade Biologics (Portland, Oreg.) and cultured as directed. Non-tumorous bladder cancer samples were provided by Dr. Stephen Boorjian (Weill Medical College, Cornell University, NY, N.Y.) and are as described in Boorjian, S, Tickoo, S K, Mongan, N P et al. Reduced Lecithin:Retinol Acyltransferase (LRAT) Expression Correlates with Increased Pathologic Tumor Stage in Bladder Cancer. Clinical Cancer Research 2004; 10:In press. Normal and All-trans-retinoic acid (RA) (Sigma, St. Louis, Mo.) was dissolved in ethanol and used at a final concentration of 20 nM or 1 µM as indicated in the descriptions of the figures.

Identification of 5'-Untranslated Region of Human Rex-1

The BLAST tool (Altschul, S F, Gish, W, Miller, W et al. Basic local alignment search tool. J Mol Biol 1990; 215:403-410) was used to identify an expressed sequence tag (EST) (Genbank accession no: BX103592) with homology to the published hRex-1 coding sequence (AF450454). The EST was isolated from a cDNA library prepared from human placental tissue (a trophoblast derived tissue) and was provided by the RZPD IMAGE cDNA clone collection. The complete sequence of hRex-1 (Genbank accession no. NM_174900) subsequently became available and matches the sequence employed here.

Reverse Transcription-Polymerase Chain Reaction

Total RNA was isolated from cells using Trizol™ (Invitrogen, Carlsbad, Calif.) as directed by the manufacturer. First strand cDNA was synthesized from 3-5 µg total RNA using Superscript™ reverse transcriptase (Invitrogen) according to the manufacturer's instructions, and the synthesized cDNA was diluted to 100 µl with sterile, ultrapure water. Primers specific for the β-actin cDNA (Genbank accession no. NM_001101) were used to confirm cDNA integrity. The primers for β-actin (379 bp product) were: 5'-gct cgt cgt cga caa cgg ctc-3' (forward) (SEQ ID NO:10) and 5'-gta cat ggc tgg ggt gtt gaa gg-3' (reverse) (SEQ ID NO:11). Oligonucleotide primers were designed to amplify the hRex-1 cDNA (302 bp product). Primers for hRex-1 were designed to span two intron-exon boundaries and thereby prevent amplification of any contaminating genomic DNA. The forward primer (located in exon II) was 5'-gct gac cac cag cac act agg c-3' (SEQ ID NO:7) and the reverse primer (located in exon IV) was 5'-ttt ctg gtg tct tgt ctt tgc ccg-3' (SEQ ID NO:8). Each PCR contained: 0.4 ng of each oligonucleotide, 1 µl cDNA, $2.5 \times 10^{-2}$ units (U) Taq DNA polymerase and accompanying 1× buffer (Invitrogen), 1.5 mM $MgCl_2$, 0.2 mM dNTPs. Thermal cycling was performed as follows: 95° C. for 5 min; followed by 35-40 cycles of 94° C. for 30 s (template denaturation); 58° C. for 30 s (oligonucleotide annealing), 72° C. for 45 s (product extension). Negative control PCRs using reverse-osmosis grade water in the place of template were incorporated in every PCR experiment. PCR products were analyzed by electrophoresis through 1.5% TAE-agarose gels and were stained with ethidium bromide. PCR experiments were repeated on at least two occasions. The identity of the amplified band was confirmed by automated DNA sequencing.

Generation and Affinity Purification of a Human Anti-REX-1 Antibody.

A C-terminal peptide of human REX-1 (S N N L K A H I L T H A N T N K N E Q E G K, SEQ ID NO:9) was custom synthesized (Invitrogen). This peptide is located beyond the zinc finger domains, at the extreme C-terminus of the hREX-1 protein. The peptide was coupled to keyhole limpet hemocyanin (KLH) and 100 µg (1 mg/ml solution) was repeatedly injected into rabbits and guinea pigs using standard methods to generate polyclonal antisera to the human REX-1 peptide (Pocono Rabbit Farm and Laboratory Inc. Canadensis, Pa.). The IgG fraction was then purified by DEAE-Affi-Gel™ blue (Sigma) column chromatography. This was followed by affinity chromatography of the IgG fraction on a peptide affinity column made by coupling the hREX-1 peptide to cyanogen-bromide activated Sepharose. The two-step purification steps were monitored by "dot-blot" assays, with peptide spotted onto nitrocellulose discs. After incubation with column fractions, the discs were processed as described for the Western blots described below.

DNA Transfections and Western Analysis

Western analysis was performed essentially as previously described in Tighe, A P and Gudas, L J Retinoic acid inhibits leukemia inhibitory factor signaling pathways in mouse embryonic stem cells. J Cell Physiol 2004; 198:223-229. Breast cancer cells and epidermal keratinocytes and epithelial cells were cultured as described above. COS cells ($2 \times 10^6$), transiently transfected with a construct expressing hRex-1, were employed as a positive control. The hRex-1 expression plasmid was constructed by PCR amplification of the full-length protein coding region of hRex-1 using Pfx proofreading polymerase (Invitrogen, CA) from a hRex-1 EST (ATCC # 5173608). Oligonucleotides, based on the hRex-1 protein coding sequence (AF450454), were designed to contain restriction sites (forward, BamH1: 5'-cgc ggatccatg agc cag caa ctg aag aaa cgg g-3' (SEQ ID NO:12) and reverse, BglII: 5'-gaagatctt cca atg agg cat gtt tgt cac tga α-3' (SEQ ID NO:13)). The amplified product was digested with BamH1 and BglII (New England BioLabs, Beverly, Mass.) and ligated into similarly digested pSG5 vector (Stratagene, Cedar Creek, Tex.). The sequence of the entire hRex-1 coding region in pSG5 was confirmed by direct automated sequencing and compared to the wild type sequence. No mutations were found to have been introduced during PCR amplification. COS cells were transfected with pSG5-hRex-1 (5-10 µg) using the DEAE-dextran method (Lane et al. (1999) Proc. Natl. Acad. Sci. USA 96:13524-29). After 48 hours, cell monolayers were washed with ice-cold PBS and harvested in sample buffer (240 mM Tris-HCl pH 6.8, 8% SDS, 40% glycerol). Aliquots (50 µg) of whole cell lysates were separated on 6-10% SDS-acrylamide gels and proteins transferred to nitrocellulose membranes (BioRad, Hercules, Calif.). The membranes were treated with an affinity purified, polyclonal rabbit anti-human human REX-1 antibody and the secondary goat anti-rabbit IgG-horse radish peroxidase conjugated antibody [#sc-2030] (Santa Cruz Biotechnology, Santa Cruz, Calif.) in PBS containing 5% Blotto (Santa Cruz), 0.1% Tween 20. Results were visualized by enhanced chemiluminescence reaction using SuperSignal (Pierce, Rockford, Ill.) and exposure to autoradiography film.

Protein Sequence Analysis

Detailed structural classification and phylogenetic analyses have been described for the zinc finger-containing protein superfamily. Chenna, R, Sugawara, H, Koike, T et al. Multiple sequence alignment with the Clustal series of programs. Nucleic Acids Research 2003; 31:3497-3500. Members of the C2H2 sub-family of zinc finger proteins possess multiple domains containing conserved cysteine and histidine residues that coordinate the zinc ion. Iuchi, S Three classes of C2H2 zinc finger proteins. Cell Mol Life Sci 2001; 58:625-635. GAP analysis (Wisconsin Package, version 10.3, Accelrys Inc.) revealed that mouse, human and rat REX-1 were related to the YY1 sub-family of transcription factors. Although the YY1 sub-family of C2H2 zinc-finger gene family has been described (Knight & Shimeld, Genome Biology 2001; 2:0016.0011-0016.0018), REX-1 proteins were not included in the dataset. Hence, the sequence relationships among these novel members of the YY1 sub-family of C2H2 transcription factors, human, mouse and rat REX-1, were analyzed in the context of the C2H2 zinc finger gene family. A protein sequence alignment of C2H2 transcription factors was constructed using Clustal W. Chenna, R, Sugawara, H, Koike, T et al. Multiple sequence alignment with the Clustal series of programs. Nucleic Acids Research 2003; 31:3497-3500. The PHYLIP package (Phylogeny Inference Package, version 3.5c, distributed by the author, J. Felsenstein, Department of Genetics, University of Washington, Seattle, USA) was employed to determine the sequence relationship of C2H2 family transcription factors. The PROTDIST program of the PHYLIP package was used to compute a distance measurement for the protein sequences, using the Dayhoff PAM matrix as described in Mongan, N P, Jones, A K, Smith, G R et al. Novel alpha7-like nicotinic acetylcholine receptor subunits in the nematode *Caenorhabditis elegans*. Protein Sci 2002; 11:1162-1171. The Neighbor-Joining (NJ) method was then used to produce an unrooted tree by examining the distance matrix calculated by PROTDIST. Although the tree generated by the NJ method was unrooted, the inclusion of a more distantly related C2H2 transcription factor, Snail (TREMBL:O95863), in the dataset (termed the out-group), allowed the tree to be rooted and the final relationship determined. The global tree was drawn using TreeView and the YY1 sub-family was extracted from the global tree and presented in FIG. 1.

Results

REX-1 is a Member of the YY1 Sub-Family of C2H2 Zinc Finger Proteins.

Figure 1:
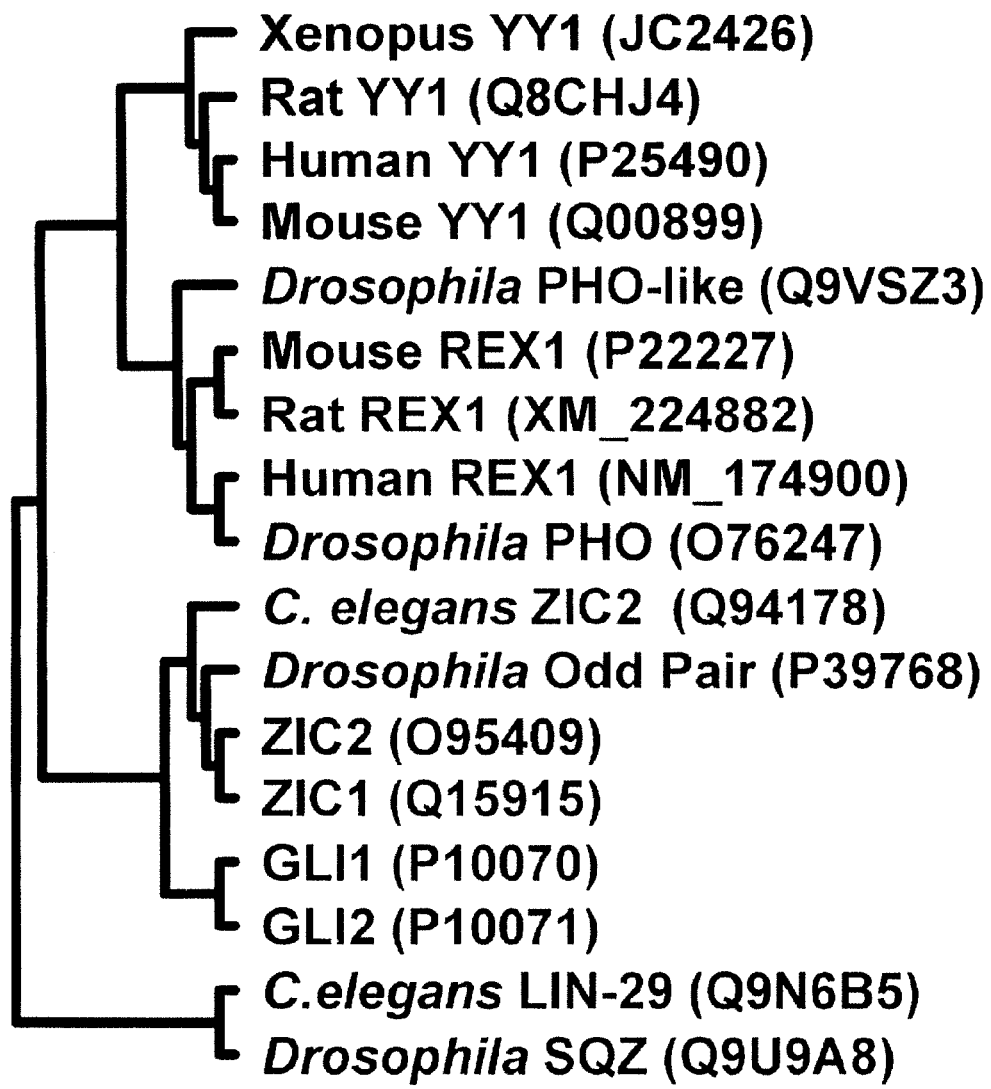
FIG. 1 provides a global tree showing the relationship of REX-1 to other members the YY1 sub-family of C2H2 zinc finger transcription factors. The YY1 sub-family of the C2H2 zinc-finger gene family has been described by Knight & Shimeld, Genome Biology 2001; 2:0016.0011-0016.0018. The inventors have now recognized that REX-1 likely belongs to the YY1 sub-family of the C2H2 zinc-finger gene family. An alignment of C2H2 family members, in addition to all known YY1 homologues (human, mouse, rat, *Danio rerio*), *Drosophila* pleiohomeotic (PHO) and REX1 (human, mouse and rat) was created using Clustal W. The global tree was constructed using the Protdist (Dayhoff PAM Distance algorithm) and Neighbor programs of the PHYLIP package. The Snail transcription factor was selected as the out-group to root the tree. The YY1 sub-family was extracted from the global tree and drawn using TREEVIEW (available at the website taxonomy.zoology.gla.ac.uk/rod/rod.html). The alignment used to generate this figure is available on request from the authors.

The TBLASTN tool was used to search the Genbank, *Drosophila* and *C. elegans* databases to identify proteins with homology to human REX-1 (AF450454). The human, mouse and rat REX1 homologues exhibited most similarity to the YY1 transcription factor sub-family of C2H2 zinc finger proteins, including the most distant member, the *Drosophila* PHO protein, which is encoded by the pleiohomeotic polycomb group gene. Brown, J L, Muscci, D, Whiteley, M et al. The *Drosophila* polycomb group gene pleiohomeotic encodes a DNA binding protein with homology to the transcription factor YY1. Mol Cell 1998; 1:1057-1064. In contrast, REX-1 homologues were not found in the *C. elegans* database. The derived amino acid sequences of known YY1 and REX-1 proteins were analyzed using pairwise Gap analysis (Wisconsin Package Version 10.3, Accelrys Inc. San Diego, Calif.) and a table of percent identity and similarity between these zinc finger proteins was compiled (Table 1). An alignment of the derived amino acid sequences of C2H2 transcription factors, including human, rat, mouse REX-1 and YY1 proteins, was determined using Clustal W. Chenna, R, Sugawara, H, Koike, T et al. Multiple sequence alignment with the Clustal series of programs. Nucleic Acids Research 2003; 31:3497-3500. A distances-matrix was created for the protein sequences using the Dayhoff PAM method of calculation in the Protdist program of the Phylip package (Felsenstein J, 1993 PHYLIP [Phylogeny Inference Package] version 3.5c, distributed by the author (Department of Genetics, University of Washington, Seattle, USA). The Neighbor-Joining method was used to generate a tree and the functionally distinct Snail protein was selected as the out-group. From these analyses the relationship between REX-1 proteins and YY1 proteins emerged (FIG. 1). Although greatest variability exists in the N-terminal regions, striking diversity between REX-1 and YY1 proteins exists at key residues in the highly conserved zinc finger domains.

protein with high sequence homology, the proposed structural model of human REX-1 possesses a conformation that is highly similar to the structure of YY1. However, sequence variability is observed in several key residues within the four zinc finger domains, which may contribute to the distinct functional properties of REX-1 and YY1.

Conserved sequence differences between the YY1 and REX-1 zinc finger domains are clustered within zinc fingers one and four; and in the loop region connecting zinc fingers three and four. It is interesting to note that residues which contribute to the third zinc finger domain are conserved in REX-1 and YY1 proteins, suggesting this domain is essential for the function of both YY1 and REX-1. In YY1, four residues of the first zinc finger domain are substituted in REX-1; H300Q; M306K; F307L and H307L. The replacement of basic histidine residues by glutamine and leucine is likely to alter the overall charge characteristic of the zinc finger. However, it is not yet possible to propose possible alterations in DNA-protein interactions based upon this. The second zinc finger possesses a single residue difference, in which the glutamine residue at position 344 in YY1 is replaced by the larger aromatic phenylalanine in REX-1. A further two residues exhibit sequence variation in the loop region connecting the third and fourth zinc fingers, an aspartate at position 380 of YY1 is replaced by the similarly charged glutamate residue in REX-1. However, the replacement of the imino residue, proline at position 382, by arginine in REX-1 may significantly alter the structural arrangement of the loop region connecting zinc fingers three and four. The fourth zinc finger domain possesses two conserved sequence differences between REX-1 and YY1 where an alanine (at position 395) and threonine (at position 398) are replaced by isoleucine and asparagine respectively.

TABLE 1

|  | Human Rex-1 | Mouse Rex-1 | Rat Rex-1 | Human YY1 | Mouse YY1 | Rat YY1 | *Danio* YY1 | *Xenopus* YY1 | *Drosophila* Pho |
| --- | --- | --- | --- | --- | --- | --- | --- | --- | --- |
| % Identity of protein sequences |  |  |  |  |  |  |  |  |  |
| Human Rex-1 | ~ | 57.45 | 58.80 | 51.48 | 52.49 | 52.49 | 54.27 | 54.58 | 41.70 |
| Mouse Rex-1 | 64.89 | ~ | 85.11 | 43.91 | 43.59 | 43.59 | 46.51 | 47.31 | 43.68 |
| Rat Rax-1 | 65.78 | 87.59 | ~ | 42.57 | 43.19 | 43.19 | 44.44 | 44.26 | 46.13 |
| Human YY1 | 57.05 | 50.92 | 50.17 | ~ | 99.52 | 98.78 | 89.01 | 91.62 | 44.48 |
| Mouse YY1 | 58.14 | 49.82 | 50.50 | 99.52 | ~ | 98.78 | 88.24 | 90.81 | 45.03 |
| Rat YY1 | 57.81 | 49.82 | 50.50 | 99.51 | 99.51 | ~ | 88.52 | 90.81 | 44.19 |
| *Danio* YY1 | 60.07 | 54.26 | 51.52 | 92.11 | 91.32 | 91.60 | ~ | 90.76 | 43.36 |
| *Xenopus* YY1 | 60.34 | 53.85 | 52.03 | 94.32 | 93.51 | 93.51 | 92.99 | ~ | 43.86 |
| *Drosophila* Pho | 49.49 | 51.26 | 53.14 | 50.87 | 52.05 | 50.58 | 50.74 | 50.88 | ~ |
| % Similarity of protein sequences |  |  |  |  |  |  |  |  |  |

Note:
Protein sequences were compared using the GAP analysis program (Wisconsin Package version 10.3, Accelrys Inc.). Figures for amino acid identify and similarity (based on a gap creation penalty of 8 and gap extension penalty of 2) are given.

Molecular Structure of Human REX-1

The human REX-1 zinc finger domains exhibits 76% identity with the human YY1 zinc finger regions (data not shown). A homology model of the three-dimensional structure of human REX was deduced using the Swiss-Model server. Schwede, T, Kopp, J, Guex, N et al. SWISS-MODEL: an automated protein homology-modeling server. Nuc Acid Res 2003; 31:3381-3385. The crystal structure of the YY1-DNA complex at 2.5 Å resolution was used as template. Houbaviy, H B, Usheva, A, Shenk, T et al. Cocrystal structure of YY1 bound to the adeno-associated virus P5 initiator. Proc Natl Acad Sci USA 1996; 93:13577-13582. As anticipated for a The BLAST tool was used to search the NCBI-Genbank human expressed sequence tag (EST) database with the human Rex-1 protein coding sequence (AF450454), to identify novel human Rex-1 homologues. Altschul, S F, Madden, T L, Schäffer, A A et al. Gapped BLAST and PSI-BLAST: a new generation of protein database search programs. Nuc Acid Res 1997; 25:3389-3402. A placental-derived EST was identified (BX103592) which demonstrated absolute homology with the 5'-region of the hRex-1 coding region, but also possessed an additional 380 bp of 5'-untranslated region not previously reported. The EST was mapped using the Genbank Entrez genome mapping function to the chromosome 4q35.2 locus, a chromosomal region syntenic with the Rex-1 locus on mouse chromosome 8. The EST was found to contain the previously unreported 5'-untranslated region and the 5'-region of the coding sequence of hRex-1 which has been described. Henderson, J K, Draper, J S, Baillie, H S et al. Preimplantation human embryos and embryonic stem cells show comparable expression of stage-specific embryonic antigens. Stem Cells 2002; 20:329-337.

The genomic structure of hRex-1 was determined by comparing the genomic and cDNA sequences (FIG. 2A). The complete hRex-1 mRNA (Genbank accession no. NM_174900) subsequently became available and matched the sequence employed here.

RT-PCR was used to detect hRex-1 expression in normal human epithelial and carcinoma cultured cell lines. Expression of hRex-1 was detected in MDA-MB-468 (FIG. 2B) mammary carcinoma cells and SCC-15 oral cavity squamous cell carcinoma cells (FIG. 2C), but was not detected in several other carcinoma cells under the conditions employed (see materials and methods). These include, breast carcinoma cells MCF-7, MDA-MB-231, MDA-MB-453, HS578T, SK-BR-3 (FIG. 2B); prostate carcinoma cells: LnCAP; renal carcinoma cells: SK-39; oral cavity squamous cell carcinoma cells: SCC-4, SCC-9, SCC-25 and acute promyelocytic leukemia cell lines: HL60 and NB-4 (FIG. 2C).

RT-PCR Detects Expression of hRex1 mRNA in Cultured Human Cells.

Figure 2:
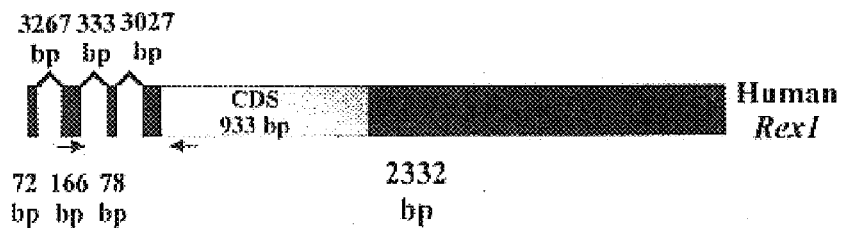
FIG. 2A schematically illustrates the genomic structure of the human Rex1 (hRex1) gene as determined by comparing the cDNA sequence with the human genome sequence. The approximate locations of oligonucleotide primers in exons II and IV, which amplify a 302 bp hRex1 fragment, are indicated.
FIG. 2B illustrates hRex1 expression in a variety of cell lines as detected by reverse transcription-polymerase chain reaction (RT-PCR). RT-PCR was performed on total RNA isolated from cultured human normal and cancer cells. Thirty five cycles of PCR were used; PCR experiments were repeated twice. Primers specific for β-actin were used to confirm the integrity of the cDNA preparation and water ($H_2O$) was employed as negative control. Cell lines examined were normal mammary epithelial cells (HMEC), and breast cancer cells MCF-7; MDA-MB-231, MDA-MB-453; HS578T; SKBR3 and MDA-MB-468. As shown, the MDA-MB-468 breast cancer cell line expresses significant Rex1 mRNA, whereas normal mammary epithelial cells and other breast cancer cell lines do not.
FIG. 2C illustrates expression of hRex1 transcripts in a variety of cell lines as detected by the RT-PCR assay. Cell lines examined were normal prostate epithelial cells (PREC), prostate cancer cells LnCAP, normal renal proximal tubule epithelial cells (RPTE), kidney cancer cells SK39; squamous cell carcinoma cells, SCC-9; SCC-25; SCC-15; and leukemic cells HL60 and NB4. As shown, the SCC-15 prostate cancer cell line expressed significant hRex1 mRNA, whereas normal prostate epithelial cells and other prostate cancer cell lines do not.
FIG. 2D illustrates expression of hRex1 transcripts in a variety of cell lines as detected by the RT-PCR assay. Cell lines examined were normal human epithelial keratinocytes (NHEK, HEKa), skin squamous cell carcinoma cells SCC-12, SCC-13, normal human bronchial (NHBE) and small airway epithelial cells (SAEC) and human teratocarcinoma cells (NTERA2). Although hRex1 expression was detectable in SAEC and NHBE cells with 35 cycles of PCR, the amplification product was more evident following forty cycles of PCR.
Figure 2:
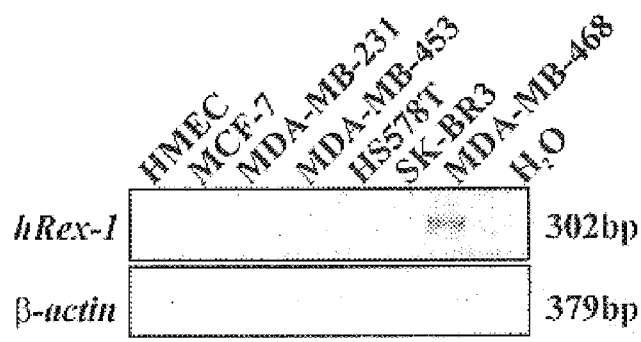
Figure 2:
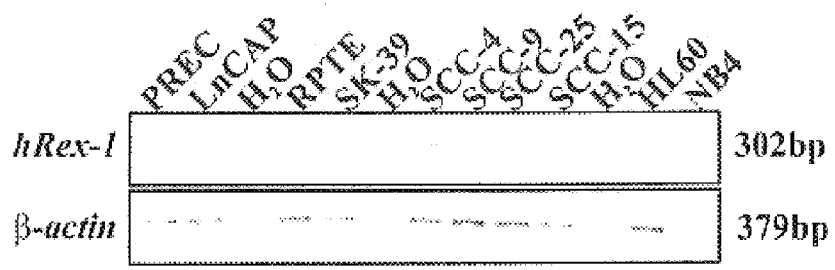
Figure 2:
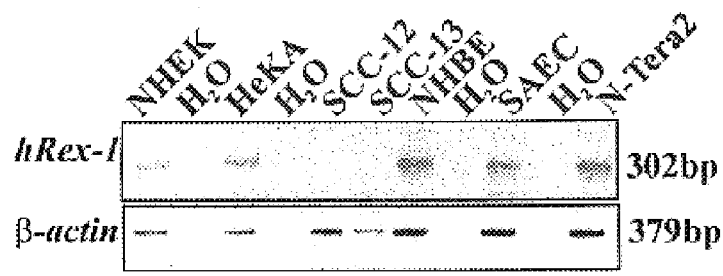
Figure 3:
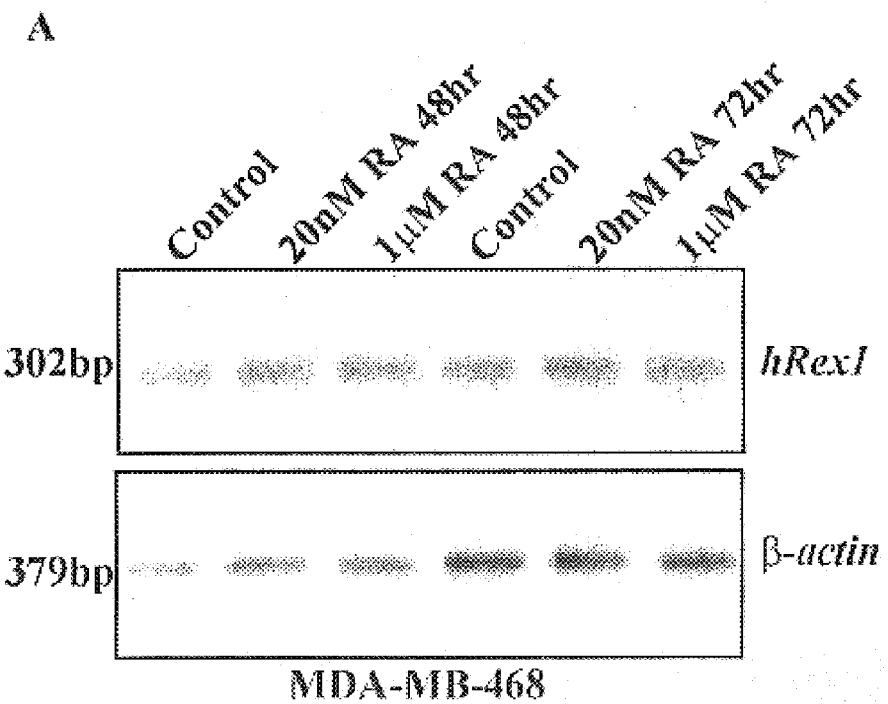
FIG. 3A shows that expression of hRex1 does not decrease following retinoic acid (RA) treatment of MDA-MB-468 cells, as detected by RT-PCR.
FIG. 3B shows that expression human REX-1 protein does not decrease significantly following treatment of MDA-MB-468 and HEKa cells with retinoic acid. Lysates (50 μg) of human breast cancer cells, MDA-MB-468 and human epidermal keratinocytes (HEKa) cells were analyzed by western blot using an affinity purified, polyclonal rabbit anti-human human REX-1 antibody as described in Example 1. COS cells transiently transfected with the hRex1 expression construct, (COS[pSG5-hRex1]), were employed as a positive control (lane 1). COS cells transfected with an empty vector (COS [pSG5]) were employed as negative control (lane 2). Levels of human REX-1 protein in MDA-MB468 (lanes 3, 4) and HEKa cells (lanes 4, 5) were unaltered following treatment with RA (1 μM) for 48 hours. Antibodies to β-actin were used as positive control. Approximate locations of molecular weight markers are indicated. Westerns were repeated three times with different cell extracts and identical results were obtained.
Figure 3:
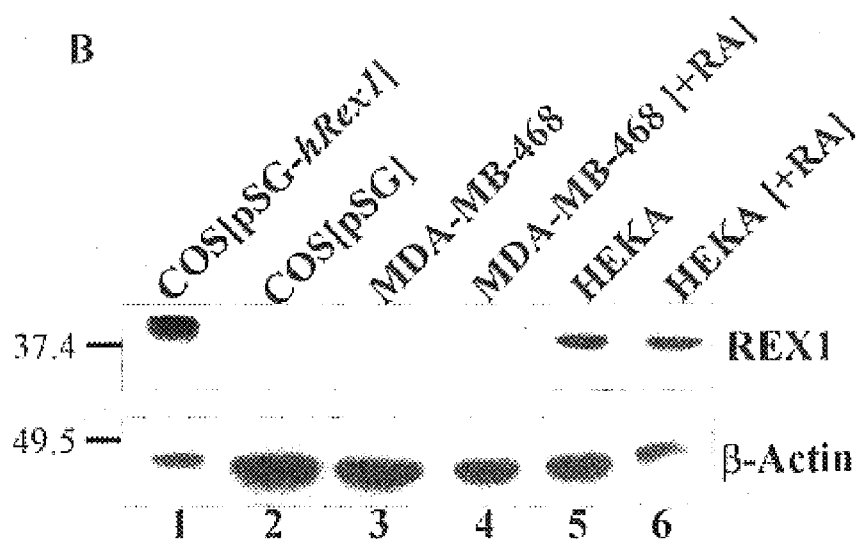

Expression of hRex-1 was detected by RT-PCR in normal human epidermal keratinocytes (NHEK) and in normal human bronchial epithelial (NHBE) and small airway epithelial cells (SAEC) (FIG. 2D). However it is important to note that SAEC also contain a small percentage of alveolar cells (Cambrex). Expression of hRex-1 was not detected in normal human mammary, prostate and renal proximal tubule (RPTE) epithelial cell cultures. Expression of hRex1 was absent in both normal and cancerous bladder samples (data not shown). As in the case of F9 mouse teratocarcinoma cells, expression of hRex-1 was detected in NTERA2 human teratocarcinoma cells (FIG. 2). Unlike the situation in murine F9 cells and ES cells (Hosler et al. (1989) Mol. Cell. Biol. 12:5623-29; Rogers et al. (1991) Development 113:815-24), expression of Rex-1 is not reduced in MDA-MB-468 (FIG. 3A) following RA-treatment (FIG. 3A). The identity of the hRex-1 PCR product was confirmed by automated DNA sequencing.

Western Analyses Detect Expression Human REX-1 Protein in Cultured Human Cells.

REX-1 protein was detected in MDA-MB-468 and HEKa cells using an affinity purified, polyclonal rabbit anti-human human REX-1 antibody. Transiently transfected COS cells that expressed human REX-1 protein were used as positive control. Treatment of MDA-MB-468 and HEKa cells with RA did not alter the level of human REX-1 protein detected (FIG. 3A,B).

The apparent molecular weight of the human REX-1 protein determined by acrylamide gel electrophoresis (FIG. 3B) is similar to the calculated molecular weight (35 kDa), suggesting the human REX-1 protein is not subject to post-translational modification.

EXAMPLE 2

Decreased Expression of Rex-1 in Renal Tumors

This Example illustrates that renal carcinoma cells have reduced levels of rex-1 expression.

Materials and Methods

Patient Tissue Collection.

Forty-two kidney specimens were obtained from 21 consecutive patients that had undergone partial or radical nephrectomy for renal tumors at the New York Presbyterian Hospital-Weill Cornell Medical Center. In 17 patients, samples were obtained from the visible tumor as well as from grossly uninvolved, adjacent renal parenchyma. Two of these 17 patients had two different areas of tumor and adjacent renal parenchyma sampled to assess for consistency within the same specimen. Four additional renal parenchymal specimens were obtained from the remaining four patients. These four specimens were procured from the opposite pole of any renal tumors and are considered to be representative of normal renal tissue. Twenty-nine of the 42 tissue specimens were equally divided such that Western blot analysis and reverse transcription-polymerase chain reaction (RTPCR) could be performed in parallel. Tissue procurement was approved by the Institutional Review Board of the New York Presbyterian Hospital. Patient and tumor demographics are listed in Table 2. Tumors were classified and staged based on final reports on the tissues submitted to the Department of Pathology, according to the 1997 American Joint Committee on Cancer-Union International Contre le Cancer (AJCC-UICC) Tumor-Node-Metastasis (TNM) classification (Guinan et al., Cancer, 80: 992-993 (1997)).

RNA Isolation and Semiquantitative Reverse Transcription-Polymerase Chain Reaction (RT-PCR).

Twenty-nine patient tissue specimens were procured and immediately placed into RNAlater™ (Ambion, Austin, Tex.). Samples were then ground using a mortar and pestle in the presence of the TRIzol reagent (Invitrogen, Carlsbad, Calif.). First strand cDNA was synthesized from 3 µg of total RNA by reverse transcription with Superscript™ III Reverse Transcriptase (Invitrogen) at 42° C. for 60 minutes, and the synthesized cDNA was diluted to 200 µl with sterile, ultra-pure water. Oligonucleotide primers were designed to amplify the human Rex-1 cDNA product. Primers were designed to span two intron-exon boundaries, thus preventing amplification of any contaminating genomic DNA. The Rex-1 primers (from GenBank accession no. NM_174900), 5'-gct gac cac cag cac act agg c-3' (forward, SEQ ID NO:7) and 5'-ttt ctg gtg tct tgt ctt tgc ccg-3' (reverse, SEQ ID NO:8), generated a 302-bp product. Conditions for PCR on the patient samples consisted of 95° C. for 5 min followed by 40 cycles of 94° C. for 30 s, 61° C. for 30 s, and 72° C. for 45 s. Each PCR contained 40 ng of each oligonucleotide primer, 2µl of cDNA, $2.5 \times 10^{-2}$ U Taq polymerase and accompanying 1× buffer (Invitrogen), 1.5 mM $MgCl_2$, and 0.2 mM deoxynucleoside triphosphates. PCR amplification of GAPDH was performed to confirm the integrity of cDNA. A 288-bp fragment of GAPDH was generated using the sense primer 5'-cgt cag aca cca tgg gga agg tg-3' (SEQ ID NO:14) and the antisense primer 5'-gct cag cgc cag cat cgc ccc act tg-3' (SEQ ID NO:15). Negative control PCR assays using reverse-osmosis grade water in the place of template were incorporated in every PCR experiment. PCR products were separated on a 1.5% agarose gel and stained with ethidium bromide. The identity of the DNA product was confirmed by comparison of the PCR-amplified DNA to the predicted fragment size, as well as automated sequencing of the PCR product and comparison to the known DNA sequences of the target gene. PCR experiments were repeated at least three times on the patient samples with similar results.

Real-Time PCR.

Real time PCR analysis was performed using a DNA Engine Opticon I system (MJ Research, Boston, Mass.) and SYBR green I Quantitect kit (Qiagen, Valencia, Calif.). The threshold cycle (CT) was set at 10-times the standard deviation above the mean baseline emission for the first 10 cycles. The oligonucleotide primer pairs for Rex-1 and GAPDH were as described above. The CT values showed linear correlation with relative DNA input for both the Rex-1 and GAPDH primer pairs employed. Reaction conditions consisted of 95° C. for 10 min to activate the polymerase followed by 50 cycles of 94° C. for 30 s, primer annealing at 60° C. for 30 s, and extension at 72° C. for 30 s; fluorescence was read after each cycle at 80° C. A standard curve was constructed for both Rex-1 and GAPDH using cDNA generated from 5 µg RNA isolated from MDA-MB-468, a breast cancer cell line that expresses Rex-1 (Example 1). Real-time analysis was performed in triplicate for each cDNA sample. Negative control PCR assays using water in place of template were performed for each experiment.

Generation of human REX-1 Antibody.

A C-terminal peptide of human REX-1 (S N N L K A H I L T H A N T N K N E Q E G K, SEQ ID NO:9) was custom synthesized (Invitrogen, Carlsbad, Calif.). This peptide is located beyond the zinc finger domains, at the extreme C-terminus of the REX-1 protein. The peptide was coupled to keyhole limpet hemocyanin (KLH) and 100 µg (1 mg/ml solution) was repeatedly injected into rabbits and guinea pigs, using standard methods, to generate polyclonal antisera to the human REX-1 peptide (Pocono Rabbit Farm and Laboratory Inc., Canadensis, Pa.). The IgG fraction was then purified by DEAE-Affigel blue (Sigma, St. Louis, Mo.) column chromatography. This was followed by affinity chromatography of the IgG fraction on a peptide affinity column made by coupling the REX-1 peptide to cyanogen-bromide activated sepharose. The two-step purification steps were monitored by "dot-blot" assays, with peptide spotted onto nitrocellulose discs. After incubation with column fractions, the discs were processed as described for the Western blots described below.

Protein Extraction and Western Blot Analysis.

Forty-two kidney tissue specimens from patients were procured and immediately placed into 2× sample buffer (100 mM Tris Cl pH 6.8, 4% sodium dodecyl sulfate, 20% glycerol). Samples were ground using a mortar and pestle, boiled for 5 min, and the supernatant was stored at −20° C. Aliquots (100 µg) of whole cell lysate were separated on a 10% SDS-acrylamide gel and proteins transferred to nitrocellulose membranes (BioRad, Hercules, Calif.). The membranes were treated with a 1:25 dilution of the rabbit anti-human REX-1 antibody overnight at 4° C., and a 1:10,000 dilution of the secondary goat anti-rabbit IgG-horse radish peroxidase conjugated antibody (#sc-2030, Santa Cruz Biotechnology, Santa Cruz, Calif.) for one hour at room temperature. All dilutions were in phosphate buffered saline (PBS) containing 5% Blotto (Santa Cruz) and 0.1% Tween-20. Results were visualized by enhanced chemiluminescence reaction using the ECL SuperSignal (Pierce, Rockford, Ill.) and exposure to autoradiography. Goat anti-human GAPDH antibody (#sc-20357, Santa Cruz Biotechnology) at a dilution of 1:1000 was used to ensure consistent loading of protein extracts. Western blot experiments were repeated at least three times on the patient samples with similar results. Intensity of the Western blot bands was quantified using NIH Image (version 1.63, National Institute of Health, Washington, D.C.).

COS cells ($2\times10^6$), transiently transfected with a construct expressing the human Rex-1, were employed as a positive control in the Western blot analyses. The Rex-1 expression plasmid was constructed by PCR amplification of the full-length protein coding region of Rex-1 using Pfx proofreading polymerase (Invitrogen) from a Rex-1 EST (ATCC # 5173608). Oligonucleotides, whose sequences were based on the Rex-1 protein coding sequence (AF450454), were designed to contain restriction sites (forward, BamH1: 5'-cgc gga tcc atg agc cag caa ctg aag aaa cgg g-3' (SEQ ID NO:12) and reverse, BglII: 5'-gaa gat ctt cca atg agg cat gtt tgt cac tga α-3' (SEQ ID NO:13).

The amplified product was digested with BamH1 and BglII (New England BioLabs, Beverly, Mass.) and ligated into similarly digested pSG5 vector (Stratagene, Cedar Creek, Tex.). The sequence of the entire human Rex-1 coding region in pSG5 was confirmed by direct automated sequencing and compared to the wild type sequence. No mutations were found to have been introduced during PCR amplification.

Immunohistochemistry.

Paraffin-embedded tissue sections from two patients and frozen sections from another patient were obtained. All three patients had Rex-1 expression confirmed by both RT-PCR and Western blot analyses, and thus were considered good candidates for attempted identification and localization of the REX-1 protein by immunohistochemistry.

Paraffin-embedded sections. Five micron tissue sections were cut from the patient blocks, and the sections were deparaffinized in Histoclear™(National Diagnostics, Atlanta, Ga.) followed by rehydration in a graded series of ethanol. Antigen retrieval was performed by heat with the Antigen Unmasking Solution (Vector Laboratories, Burlingame, Calif.) in a pressure cooker for 8 minutes. A 3% solution of $H_2O_2$ was used to quench the endogenous peroxidase activity (15 minute incubation). Slides were initially blocked with 1.5% goat serum for 30 minutes. This was followed by incubation with the affinity-purified, polyclonal rabbit antihuman REX-1 primary antibody diluted 1:5 in 1.5% goat serum for 45-60 min. at room temperature, and then with 100 µL of horseradish peroxidase (HRP) conjugated goat anti-rabbit secondary antibody (SuperPicture, Zymed, San Francisco, Calif.) for 30 minutes at room temperature. Color was developed with the 3,3'-diaminobenzidine chromogen substrate, followed by counterstaining with hematoxylin (Vector). The negative control normal and tumor sections were treated identically to all other sections, with the exception that 1.5% normal goat serum was used in place of the primary antibody. Primary antibody incubation was also performed in the presence of REX-1 free peptide (1 µg/µL) to assess for non-specific primary antibody binding. All samples were analyzed using this identical protocol with the same reagents. The staining procedures were repeated at least three times with similar results.

Frozen sections. Seven-µm tissue sections were cut from the patient's block and were stored at −80° C. until staining. Slides were thawed at room temperature for 30 minutes and were fixed in 100% acetone for two minutes. Slides were initially blocked with 10% goat serum for 20 minutes at room temperature. This was followed by incubation with the affinity-purified, polyclonal rabbit anti-human REX-1 primary antibody diluted 1:5 in 1% goat serum overnight at 4° C. The next day the slides were at incubated with 100 µL of horseradish peroxidase (HRP) conjugated goat anti-rabbit secondary antibody (SuperPicture, Zymed) for 30 minutes at room temperature. Endogenous peroxidase activity was quenched with a 0.3% solution of $H_2O_2$ for 20 minutes. Color was developed with the 3,3'-diaminobenzidine chromogen substrate, followed by counterstaining with hematoxylin (Vector). The negative control normal and tumor sections were treated identically to all other sections, with the exception that 1% goat serum was used in place of the primary antibody. The staining procedures were repeated at least three times with similar results.

Statistical Analysis.

Excel 2000 (Microsoft, Redmond, Wash.) software and SAS for Windows, version 9.1 (SAS Institute, Cary, N.C.) were used to perform all statistical calculations, where in these experiments p<0.05 was considered statistically significant. The chi-square ($\chi^2$) test was used to compare mRNA and protein expression in the normal and tumor tissue specimens.

Results

RT-PCR Analysis of Rex-1 Expression in Normal Renal Tissue Versus Renal Tumors.

Twenty-nine kidney tissue specimens obtained from 15 patients were evaluated for Rex-1 mRNA expression (Table 2). In fourteen of 15 patients both tumor and adjacent non-tumor specimens were obtained, while in one patient only normal-appearing renal tissue was procured.

TABLE 2

Patient Demographics and Tumor Characteristics of Partial or Radical Nephrectomy Specimens Used in RT-PCR and Western Blot Analyses for Rex-1

| | Patient (n = 15) Data: Rex-1 expression (RT-PCR) | Patients (n = 21) Data: REX-1 protein levels |
|---|---|---|
| Age (yr) | | |
| Mean | 60.8 | 62.1 |
| Range | 32-88 | 32-88 |
| Gender | | |
| Male | 9 | 14 |
| Female | 6 | 7 |
| Pathology | | |
| Normal | 1 | 4 |
| RCC, clear cell | 6 | 9 |
| RCC, papillary | 3 | 3 |
| RCC, chromophobe | 1 | 1 |
| RCC, unclassified | 2 | 2 |
| Renal oncocytoma | 2 | 2 |
| Tumor stage | | |
| T0 (normal) | 1 | 4 |
| T1a | 12 | 13 |
| T1b | 2 | 3 |
| T2 | 0 | 0 |
| T3 | 0 | 1 |
| T4 | 0 | 0 |
| Tumor size (cm) | | |
| Mean | 4.2 | 4.2 |
| Range | 1.1-10.5 | 1.1-10.5 |
| Tumor Location | | |
| Side (Left/Right) | 8L/7R | 11L/10R |
| Upper pole | 8 | 10 |
| Middle pole | 4 | 6 |
| Lower pole | 3 | 5 |

Figure 4:
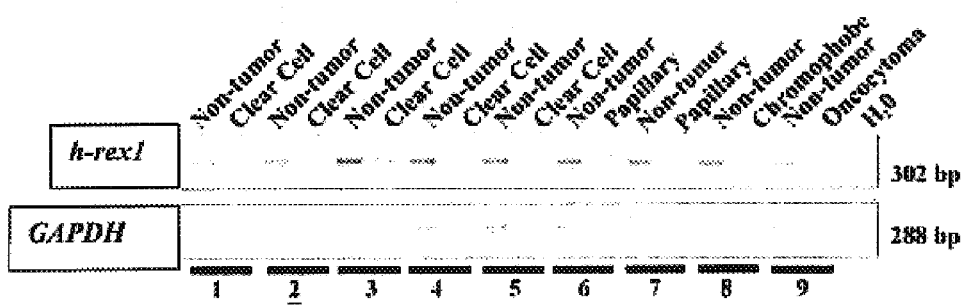
FIG. 4 illustrates expression of Rex-1 mRNA in renal tumors compared with adjacent, non-tumor renal parenchyma. Results from nine patients are shown. Pairs 1-5, non-tumor and adjacent clear cell carcinoma; Pairs 6 and 7, non-tumor and adjacent papillary carcinoma; Pair 8, non-tumor and adjacent chromophobe carcinoma; and Pair 9, non-tumor and an adjacent oncocytoma renal tumor. Amplification with PCR primers specific for GAPDH confirmed the integrity and quantity of the cDNA used. PCR for Rex-1 and GAPDH expression consisted of 40 and 30 cycles, respectively. All PCR amplifications were performed in triplicate with identical results. One experiment is shown.

In fourteen of 15 patients both tumor and adjacent non-tumor specimens were obtained, while in one patient only normal-appearing renal tissue was procured. Results from a representative semi-quantitative RT-PCR analysis are shown in FIG. 4, a summary in Table 3 of the Rex-1 expression in all 29 tissue samples. In Table 3, positive Rex-1 mRNA expression is reported for a sample when a band was detected by RT-PCR after 40 cycles using the conditions reported above in the Example. Negative Rex-1 mRNA expression was reported in Table 3 if a signal was not detected by RT-PCR under those conditions.

TABLE 3

Summary of Semi-Quantitative RT-PCR for Rex-1 mRNA Expression in Kidney Tissue Specimens

| | No. Specimens | No. Expressing Rex-1 (%) | P Value |
|---|---|---|---|
| Paired Specimens | 28 | | |
| Non-Tumor | 14 | 13 (93%) | <0.005 |
| Tumor | 14 | 5 (36%) | |
| Unpaired Specimens | 1 | | |
| Non-Tumor | 1 | 1 (100) | — |
| Tumor | 0 | 0 | |
| Total | 29 | | |
| Non-Tumor | 15 | 14 (93%) | <0.005 |
| Tumor | 14 | 5 (36%) | |

Under the conditions employed, Rex-1 mRNA expression was noted in 14/15 (93%) non-tumor renal tissue specimens compared with 5/14 (36%) renal tumor specimens (p<0.005). There was no difference in Rex-1 expression between the oncocytoma renal tumors and any of the different histologic subtypes of RCC (Table 4). One patient with clear cell carcinoma exhibited essentially no Rex-1 expression in both normal and tumor specimens. No independent correlation between Rex-1 expression and Fuhrman histologic grade, pathologic tumor stage, tumor location, or tumor size was noted (data not shown).

Real-Time PCR Analysis of Rex-1 mRNA Expression in Normal Renal Tissue and Adjacent Renal Tumors.

Figure 5:
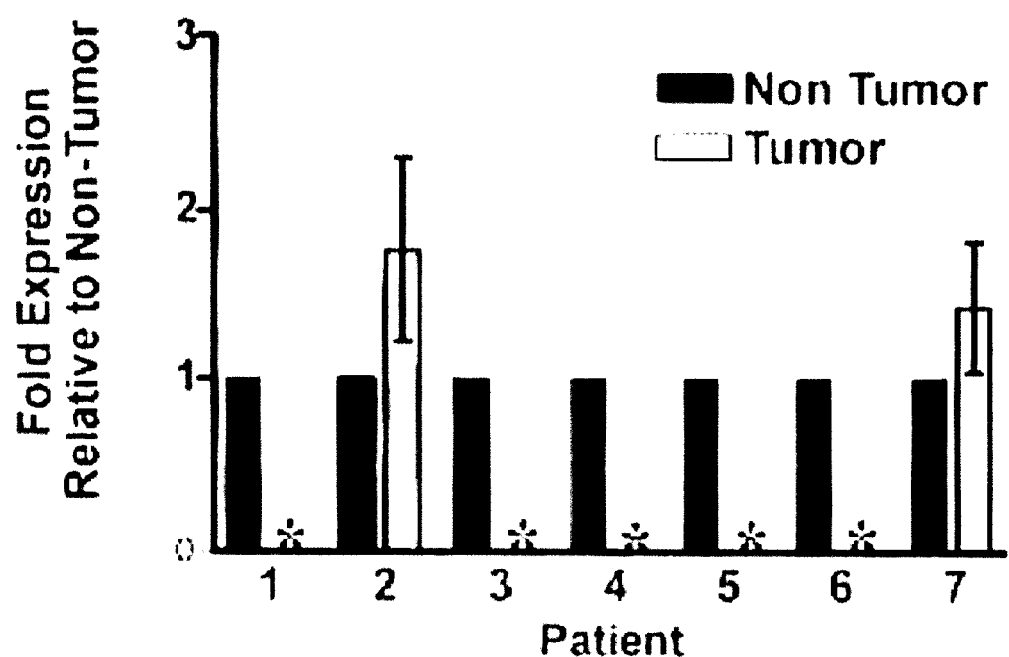
FIG. 5 graphically illustrates the fold-expression of human Rex-1 normalized to GAPDH in tumorous (light bars) and non-tumorous (dark bars) renal tissues from seven patients as determined by PCR. Real-time PCR was performed on RNA isolated from matched tumor and adjacent, non-tumor renal tissue from seven patients: two with clear cell carcinoma (patients 1 and 2); two with papillary carcinoma (patients 3 and 4); two with chromophobe carcinoma (patients 5 and 6); and one with oncocytoma (patient 7). The relative level of Rex-1 expression for each specimen was determined with reference to the internal GAPDH control. Real-time analysis was performed in triplicate for each cDNA sample. Expression is depicted as fold expression relative to adjacent, non-tumor renal samples and the mean data presented. The symbol * indicates hRex1 expression less than 0.5% of adjacent renal non-tumor sample. Bars=standard deviation. Negative control PCR assays using water in place of template were performed for each experiment.

Real-time PCR for Rex-1 expression was performed on RNA isolated from matched tumor and adjacent, non-tumor renal tissue from seven patients. The distribution of specimens included two clear cell carcinomas, two papillary carcinomas, two chromophobe carcinomas, and one oncocytoma tumor. Expression of Rex-1 mRNA was absent in five tumor samples in relation to adjacent normal renal tissue, while two tumor samples had similar levels of expression compared to normal (FIG. 5). These results support our data with semi-quantitative PCR (FIG. 4, Table 3).

Western Blot Analysis of REX-1 Protein Expression in Normal Renal Parenchyma versus Renal Tumors.

Forty-two kidney tissue specimens obtained from 21 patients were evaluated for REX-1 protein expression (Table 2). Thirty-eight of these specimens were from 19 pairs of tumor and adjacent non-tumor, while the remaining four specimens were unpaired, normal renal parenchyma. Results from a representative Western blot analysis are shown in FIG. 6, with a summary of REX-1 protein expression provided in Table 4. Transiently transfected COS cells expressing the human REX-1 protein were used as a positive control.

TABLE 4

Summary of Western Blot Analysis of REX-1 Protein Expression in Patient Tissue Specimens

|  | No. Specimens | No. Expressing REX-1 (%) | p Value |
|---|---|---|---|
| Paired Specimens |  |  |  |
| Non-Tumor | 19 | 17 (89%) | <0.001 |
| Tumor | 19 | 7 (37%) |  |
| Unpaired Specimens | 4 |  |  |
| Non-Tumor | 4 | 4 (100) | — |
| Tumor | 0 | 0 |  |
| Total | 42 |  |  |
| Non-Tumor | 23 | 21 (91%) | <0.001 |
| Tumor | 19 | 7 (37%) |  |

REX-1 protein expression was noted in 21/23 (91%) normal renal tissue specimens compared to 7/19 (37%) renal tumor specimens (p<0.001). In 6 of the 7 renal tumor specimens where REX-1 protein expression was detected, the levels were at least three-fold lower than that in adjacent normal kidney tissue. There was minimal variance in REX-1 expression in the two patients who had two different areas of tumor and adjacent renal parenchyma sampled (data not shown). Similar to the mRNA data, there was no difference in REX-1 protein expression between oncocytomas and any of the different histologic subtypes of RCC (Table 5). Two patients with RCC (one clear cell and one unclassified) exhibited no REX-1 expression in either normal or malignant renal tissue. There was no correlation between REX-1 protein expression and histologic tumor grade or stage.

TABLE 5

Summary of mRNA and Protein Expression by Histologic Subtype of Renal Tumors

| Histologic Subtype | No. Expressing Rex-1 mRNA (%) | No. Expressing REX-1 Protein (%) |
|---|---|---|
| Clear Cell | 2/6 (33%) | 4/9 (44%) |
| Papillary | 1/3 (33%) | 1/3 (33%) |
| Chromophobe | 0/1 (0%) | 0/1 (0%) |
| Unclassified | 1/2 (50%) | 1/2 (50%) |
| Oncocytoma | 1/2 (50%) | 1/2 (50%) |
| Total | 5/14 (36%) | 7/19 (37%) |

Immunohistochemical Localization of REX-1 Protein Expression in Normal Renal Parenchyma and Adjacent Carcinoma.

Figures 7A, 7B:
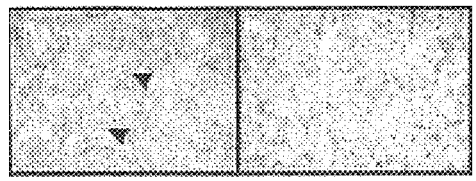
Figures 7C, 7D:
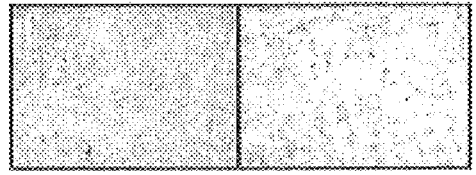
Figures 7E, 7F:
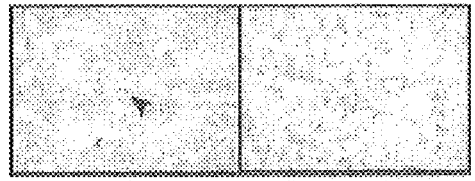
Figures 7G, 7H:
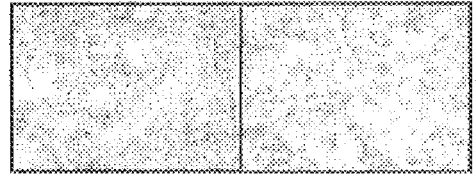
Figures 7I, 7J:
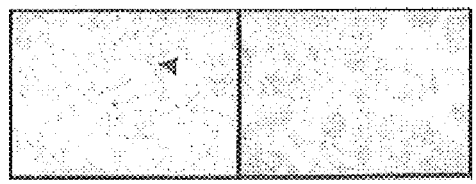
Figures 7K, 7L:
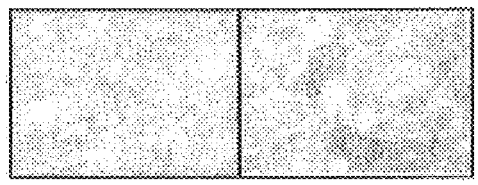

Paraffin-embedded sections were obtained from two patients (with clear cell carcinoma) and frozen sections were obtained from another patient (with papillary carcinoma) whose RT-PCR and Western blot analyses of tissue specimens revealed Rex-1 expression in normal renal parenchyma. Slides were stained to determine which cells expressed REX-1 protein (FIG. 7). FIGS. 7A, E and I show that normal renal parenchyma exhibited granular staining indicative of REX-1 protein, predominantly in the cytoplasmic region of a small percentage (~1-2%) of proximal renal tubular cells. In general, the staining was observed in most of the epithelial cells in a single tubule, but only a small percentage of tubules were stained (~1-2%). This staining was reproducible and was distinct from background staining (FIGS. 7C, G, and K). Moreover, this staining was eliminated by incubating with 1 µg/mL of free human REX-1 peptide, thus demonstrating the specificity of binding (data not shown). REX-1 immunostaining was not observed in any of the three carcinoma specimens (FIGS. 7B, F and J) or respective negative controls (FIGS. 7D, H and L).

The identification of stem cell populations in tissues with low regenerative potential has fostered interest in renal stem cells. The identification, isolation, and regulation of such stem cells may provide innovative therapeutic options for acute renal failure, end stage renal disease, and renal transplantion. Koh et al., J. Am. Soc. Nephrol. 15: 1113-1125 (2004); Hammerman, M. R. Transpl Immunol, 12: 211-218 (2004); Chang et al. Can. J. Surg. 47: 122-129 (2004).

It appears that kidney stem cells may exist in both renal tissue as well as in the peripheral circulation. In a murine renal transplantation model, Poulsom and colleagues utilized in-situ hybridization to demonstrate that circulating stem cells can engraft in the kidney and differentiate into renal parenchymal cells (J. Pathol. 195: 229-235 (2001)). Other human and rodent experimental studies have suggested that bone marrow derived mesenchymal stem cells have the capacity to participate in renal repair in injury states. Ito et al. J. Am. Soc. Nephrol. 12: 2625-2635, 2001; Gupta et al. Kidney Int. 62: 1285-1290 (2002); Rookmaaker et al. Am. J. Pathol. 163: 553-562 (2003); Kale et al. J. Clin. Invest. 112: 42-49 (2003); Morigi et al. J. Am. Soc. Nephrol. 15: 1794-1804 (2004). In these injury and regeneration models, it is the possible that extrarenal stem cells are preferentially recruited to the kidney, thus confounding identification of native renal stem cells. It is also likely that organ specific renal stem cells do exist. BrdU staining can be used to identify "label retaining cells" by virtue of the fact that these organ-specific stem cells exhibit limited cell divisions. Cotsarelis et al. Exp Dermatol, 8: 80-88 (1999).

This technique has identified diffuse labeling in the proximal, distal, and collecting tubules, as well as in the renal papilla in normal kidneys suggesting the presence of a persistent renewing stem cell population. Oliver et al. J. Clin. Invest. 114: 795-804 (2004); Maeshima et al. J. Am. Soc. Nephrol. 14: 3138-3146, 2003. In addition, isolation of epithelial cells from renal tubules of normal adult rabbit kidneys has demonstrated the capacity for self-renewal, as well as for differentiation into renal tubular structures in vitro. Humes et al. Am J Physiol, 271: F42-49 (1996).

The utilization of stem cell molecular markers can facilitate the identification of organspecific stem cells in adult tissues. In this study, the expression of the human stem cell marker, Rex-1, was investigated in normal and neoplastic adult kidney tissue specimens. A high level of Rex-1 mRNA and protein expression was observed in over 90% of normal renal parenchymal specimens. In contrast, Rex-1 mRNA and protein expression decreased by greater than three-fold in most renal tumor specimens of all histological subtypes. REX-1 protein was localized dominantly in the cytoplasmic region of approximately 1-2% of proximal renal epithelial tubules in normal renal tissue, with staining absent in three renal cell carcinoma specimens.

Proximal renal tubule epithelium is known for its capacity for regeneration in the setting of toxic or ischemic injury (Wallin et al. Lab. Invest. 66: 474-484 (1992); Toubeau et al., Exp. Nephol. 2: 229-39 (1994); Kays & Schnellmann, Toxicol. Appl. Pharmacol. 132: 273-80 (1995). While hematopoietic stem cells contribute to this regeneration (Lin et al. J. Am. Soc. Nephol. 14: 1188-99 (2003)), the data provided herein indicates that a population of renal stem cells is localized to the renal tubules.

Given that REX-1 is a transcription factor, one might expect that the staining would predominantly be nuclear, as opposed to cytoplasmic. This, however, does not appear to be the case.

The inventors have previously demonstrated that REX-1 is highly homologous to the Ying-Yang1 (YY1) transcription factor (Thompson & Gudas, Mol. Cell Endocrinol. 195: 119-33 (2002)). Recently, Palko and colleagues demonstrated that the subcellular distribution pattern of YY1 differed during the cell cycle (Palko et al. J. Cell. Sci. 117: 465-76 (2004)), reporting that YY1 is predominantly cytoplasmic in the GI phase, primarily nuclear during the early and middle S phase, and subsequently cytoplasmic later in S phase. These findings suggest that YY1, and perhaps REX-1 as well, localizes to the cytoplasm during most of the cell cycle.

While the REX-1 staining was observed in only a small percentage of proximal renal tubules (~1-2%), it appeared to involve most of the epithelial cells in a single tubule. One explanation for this pattern of staining is that some proximal tubules may possess a greater stem cell population than others. Further, while these proximal tubules in a tissue section may appear separate, distinct and unrelated, their three-dimensional orientation may actually suggest a specific location of proximal tubules containing stem cells within the kidney. Another potential hypothesis is that following injury, stem cells contribute to the regeneration of renal tubular epithelial cells. It is possible that these newly regenerated tubular cells have yet to fully differentiate and thus still possess some stem cell markers, such as Rex-1.

The cancer stem cell hypothesis suggests that only a small fraction of cells in the tumor possess the ability to proliferate and self-renew extensively. The remaining tumor cells lack this ability to proliferate and eventually evolve into a population of cells that becomes the tumor's phenotype (Singh et al., Oncogene 23: 7267-73 (2004). Given the similarity between embryonic stem cells and cancer stem cells (CSCs) (Beachy et al. Nature 432: 324-31 (2004)), it is postulated that embryonic gene markers may be a reasonable means to identify and isolate such cancer stem cells.

As shown herein, the majority of renal tumor specimens demonstrated decreased expression of the Rex-1 stem cell marker in comparison to normal adjacent renal parenchyma. There are several potential explanations for this observation. One possibility is that the absence of detectable Rex-1 expression may indicate a lower prevalence, but not the complete absence of cancer stem cells. Another possibility is that these tumors have originated from a more differentiated progenitor cell during the process of carcinogenesis (Sell, S. Environ. Health Perspect 101 Suppl. 5: 15-26 (1993)). As a consequence, these tumors may lack some or most of the gene signatures expressed in undifferentiated stem cells, including Rex-1.

Rex-1 expression was detected in just over one-third of renal tumor specimens. The earlier detection of renal cell carcinoma has resulted in most newly diagnosed tumors being confined to the kidney (stages T1a and T1b) (Russo, P. Curr. Treat Options Oncol. 2:447-455 (2001)). Increased Rex-1 expression may suggest a higher concentration of cancer stem cells within a particular tumor. A higher population of cancer stem cells may portend a more aggressive phenotypic disease and may identify a sub-population of patients who would benefit from more vigilant screening or immediate adjuvant therapy.

One therapeutic modality that has already been preliminarily explored in renal cell carcinoma is treatment with retinoids (Goldberg et al. Cancer 95: 1220-27 (2002)). Retinoids, which are known to decrease Rex-1 expression in mouse ES and F9 teratocarcinoma cells by promoting cellular differentiation (Hosler et al. Mol. Cell. Biol. 9: 5623-29 (1989)), may be particularly beneficial in patients with tumors demonstrating high Rex-1 expression.

In summary, the data provided herein demonstrate high levels of expression of the human stem cell marker, REX-1, in normal renal parenchyma with localization to the proximal renal epithelial tubules. Furthermore, both Rex-1 mRNA and protein expression are significantly decreased in most renal cell carcinoma specimens.

EXAMPLE 4

Expression of Rex-1 in Laryngeal Tumors and Oral Cavity Cancers

This Example illustrates rex-1 expression in laryngeal and oral cavity cancer cells.

Immunohistochemistry.

Paraffin-embedded tissue sections were prepared from laryngeal and oral cavity cancer tissues patients and the sections were subjected to immunohistochemistry as described in the previous Example.

Results

Sections of laryngeal and oral cancer tissues were stained to determine whether these cancer cells expressed more or less REX-1 protein than normal cells of the same tissue type. As shown in FIGS. 8A-B cancerous laryngeal tissue sections exhibited REX-1 expression. FIG. 8C provides a control section of cancerous laryngeal tissue that was not stained with anti-REX-1 antibody. These slides indicate that phenotypically normal cells exhibit higher levels of REX-1 expression than cells that were phenotypically identified as cancerous cells.

Similarly, sections from specimens containing cancerous and normal human oral cavity cells also exhibited expression of REX-1 protein in normal cells with lesser REX-1 expression in cells with an invasive, moderately differentiated SCC cancerous phenotype (FIGS. 9A, 10A-B). FIGS. 9B, 10C provide control, non-antibody stained sections of the same tissues shown in FIGS. 9A and 10A-B, respectively. Therefore, REX-1 expression is substantially different in cancerous tissues relative to normal tissues of the same tissue type.

REFERENCES

1. Fuchs, E. and Segre, J. A. Stem cells: a new lease on life. Cell, 100: 143-155, 2000.
2. Akashi, K., Traver, D., Miyamoto, T., and Weissman, I. L. A clonogenic common myeloid progenitor that gives rise to all myeloid lineages. Nature, 404: 193-197, 2000.
3. Krause, D. S., Theise, N. D., Collector, M. I., et al. Multi-organ, multi-lineage engraftment by a single bone marrow-derived stem cell. Cell, 105: 369-377, 2001.
4. Tumbar, T., Guasch, G., Greco, V., et al. Defining the epithelial stem cell niche in skin. Science, 303: 359-363, 2004.
5. Marshman, E., Booth, C., and Potten, C. S. The intestinal epithelial stem cell. Bioessays, 24: 91-98, 2002.
6. Gage, F. H. Mammalian neural stem cells. Science, 287: 1433-1438, 2000.
7. Clayton, H., Titley, I., and Vivanco, M. Growth and differentiation of progenitor/stem cells derived from the human mammary gland. Exp Cell Res, 297: 444-460, 2004.

8. Bhatt, R. I., Brown, M. D., Hart, C. A., et al. Novel method for the isolation and characterisation of the putative prostatic stem cell. Cytometry, 54A: 89-99, 2003.
9. Rookmaaker, M. B., Verhaar, M. C., van Zonneveld, A. J., and Rabelink, T. J. Progenitor cells in the kidney: biology and therapeutic perspectives. Kidney Int, 66: 518-522, 2004.
10. Oliver, J. A., Maarouf, O., Cheema, F. H., Martens, T. P., and Al-Awqati, Q. The renal papilla is a niche for adult kidney stem cells. J Clin Invest, 114: 795-804, 2004.
11. Ramalho-Santos, M., Yoon, S., Matsuzaki, Y., Mulligan, R. C., and Melton, D. A. "Stemness": transcriptional profiling of embryonic and adult stem cells. Science, 298: 597-600, 2002.
12. Brivanlou, A. H., Gage, F. H., Jaenisch, R., Jessell, T., Melton, D., and Rossant, J. Stem cells. Setting standards for human embryonic stem cells. Science, 300: 913-916, 2003.
13. Richards, M., Tan, S. P., Tan, J. H., Chan, W. K., and Bongso, A. The transcriptome profile of human embryonic stem cells as defined by SAGE. Stem Cells, 22: 51-64, 2004.
14. Rogers, M. B., Hosler, B. A., and Gudas, L. J. Specific expression of a retinoic acidregulated, zinc-finger gene, Rex-1, in preimplantation embryos, trophoblast and spermatocytes. Development, 113: 815-824, 1991.
15. Hosler, B. A., LaRosa, G. J., Grippo, J. F., and Gudas, L. J. Expression of REX-1, a gene containing zinc finger motifs, is rapidly reduced by retinoic acid in F9 teratocarcinoma cells. Mol Cell Biol, 9: 5623-5629, 1989.
16. Hosler, B. A., Rogers, M. B., Kozak, C. A., and Gudas, L. J. An octamer motif contributes to the expression of the retinoic acid-regulated zinc finger gene Rex-1 (Zfp-42) in F9 teratocarcinoma cells. Mol Cell Biol, 13: 2919-2928, 1993.
17. Chen, A. C. and Gudas, L. J. An analysis of retinoic acid-induced gene expression and metabolism in AB1 embryonic stem cells. J Biol Chem, 271: 14971-14980, 1996.
18. Ben-Shushan, E., Thompson, J. R., Gudas, L. J., and Bergman, Y. Rex-1, a gene encoding a transcription factor expressed in the early embryo, is regulated via Oct-3/4 and Oct-6 binding to an octamer site and a novel protein, Rox-1, binding to an adjacent site. Mol Cell Biol, 18: 1866-1878, 1998.
19. Henderson, J. K., Draper, J. S., Baillie, H. S., et al. Preimplantation human embryos and embryonic stem cells show comparable expression of stage-specific embryonic antigens. Stem Cells, 20: 329-337, 2002.
20. Thompson, J. R. and Gudas, L. J. Retinoic acid induces parietal endoderm but not primitive endoderm and visceral endoderm differentiation in F9 teratocarcinoma stem cells with a targeted deletion of the Rex-1 (Zfp-42) gene. Mol Cell Endocrinol, 195: 119-133, 2002.
21. Jiang, Y., Vaessen, B., Lenvik, T., Blackstad, M., Reyes, M., and Verfaillie, C. M. Multipotent progenitor cells can be isolated from postnatal murine bone marrow, muscle, and brain. Exp Hematol, 30: 896-904, 2002.
22. Jiang, Y., Jahagirdar, B. N., Reinhardt, R. L., et al. Pluripotency of mesenchymal stem cells derived from adult marrow. Nature, 418: 41-49, 2002.
23. Hanahan, D. and Weinberg, R. A. The hallmarks of cancer. Cell, 100: 57-70, 2000.
24. Reya, T., Morrison, S. J., Clarke, M. F., and Weissman, I. L. Stem cells, cancer, and cancer stem cells. Nature, 414: 105-111, 2001.
25. Al-Hajj, M. and Clarke, M. F. Self-renewal and solid tumor stem cells. Oncogene, 23: 7274-7282, 2004.
26. Jemal, A., Tiwari, R. C., Murray, T., et al. Cancer statistics, 2004. CA Cancer J Clin, 54: 8-29, 2004.
27. DeVita S E, H. S., Rosenberg, S. A. Cancer: principles and practice of oncology, 7 edition. Philadelphia: Lippincott Williams & Wilkins, 2004.
28. Tan, M. H., Rogers, C. G., Cooper, J. T., et al. Gene expression profiling of renal cell carcinoma. Clin Cancer Res, 10: 6315S-6321S, 2004.
29. Tickoo, S. K. and Amin, M. B. Discriminant nuclear features of renal oncocytoma and chromophobe renal cell carcinoma. Analysis of their potential utility in the differential diagnosis. Am J Clin Pathol, 110: 782-787, 1998.
30. Linehan, W. M., Walther, M. M., and Zbar, B. The genetic basis of cancer of the kidney. J. Urol. 170: 2163-2172, 2003.
31. Young, A. N., Amin, M. B., Moreno, C. S., et al. Expression profiling of renal epithelial neoplasms: a method for tumor classification and discovery of diagnostic molecular markers. Am J Pathol, 158: 1639-1651, 2001.
32. Takahashi, M., Yang, X. J., Sugimura, J., et al. Molecular subclassification of kidney tumors and the discovery of new diagnostic markers. Oncogene, 22: 6810-6818, 2003.
33. Jordan, C. T. Cancer stem cell biology: from leukemia to solid tumors. Curr Opin Cell Biol, 16: 708-712, 2004.
34. Guinan, P., Sobin, L. H., Algaba, F., et al. TNM staging of renal cell carcinoma: Workgroup No. 3. Union International Contre le Cancer (UICC) and the American Joint Committee on Cancer (AJCC). Cancer, 80: 992-993, 1997.
35. Koh, C. J. and Atala, A. Tissue engineering, stem cells, and cloning: opportunities for regenerative medicine. J Am Soc Nephrol, 15: 1113-1125, 2004.
36. Hammerman, M. R. Treatment for end-stage renal disease: an organogenesis/tissue engineering odyssey. Transpl Immunol, 12: 211-218, 2004.
37. Chang, E. N., Scudamore, C. H., and Chung, S. W. Transplantation: focus on kidney, liver and islet cells. Can J Surg, 47: 122-129, 2004.
38. Poulsom, R., Forbes, S. J., Hodivala-Dilke, K., et al. Bone marrow contributes to renal parenchymal turnover and regeneration. J Pathol, 195: 229-235, 2001.
39. Ito, T., Suzuki, A., Imai, E., Okabe, M., and Hori, M. Bone marrow is a reservoir of repopulating mesangial cells during glomerular remodeling. J Am Soc Nephrol, 12: 2625-2635, 2001.
40. Gupta, S., Verfaillie, C., Chmielewski, D., Kim, Y., and Rosenberg, M. E. A role for extrarenal cells in the regeneration following acute renal failure. Kidney Int, 62: 1285-1290, 2002.
41. Rookmaaker, M. B., Smits, A. M., Tolboom, H., et al. Bone-marrow-derived cells contribute to glomerular endothelial repair in experimental glomerulonephritis. Am. J. Pathol. 163: 553-562, 2003.
42. Kale, S., Karihaloo, A., Clark, P. R., Kashgarian, M., Krause, D. S., and Cantley, L. G. Bone marrow stem cells contribute to repair of the ischemically injured renal tubule. J. Clin. Invest. 112: 42-49, 2003.
43. Morigi, M., Imberti, B., Zoja, C., et al. Mesenchymal stem cells are renotropic, helping to repair the kidney and improve function in acute renal failure. J Am Soc Nephrol, 15:1794-1804, 2004.
44. Cotsarelis, G., Kaur, P., Dhouailly, D., Hengge, U., and Bickenbach, J. Epithelial stem cells in the skin: definition, markers, localization and functions. Exp Dermatol, 8: 80-88, 1999.

45. Maeshima, A., Yamashita, S., and Nojima, Y. Identification of renal progenitor-like tubular cells that participate in the regeneration processes of the kidney. J. Am. Soc. Nephrol. 14: 3138-3146, 2003.
46. Humes, H. D., Krauss, J. C., Cieslinski, D. A., and Funke, A. J. Tubulogenesis from isolated single cells of adult mammalian kidney: clonal analysis with a recombinant retrovirus. Am J Physiol, 271: F42-49, 1996.
47. Wallin, A., Zhang, G., Jones, T. W., Jaken, S., and Stevens, J. L. Mechanism of the nephrogenic repair response. Studies on proliferation and vimentin expression after 35S25 1,2-dichlorovinyl-L-cysteine nephrotoxicity in vivo and in cultured proximal tubule epithelial cells. Lab Invest, 66: 474-484, 1992.
48. Toubeau, G., Nonclercq, D., Zanen, J., Laurent, G., Schaudies, P. R., and Heuson-Stiennon, J. A. Renal tissue expression of EGF and EGF receptor after ischaemic tubular injury: an immunohistochemical study. Exp Nephrol, 2: 229-239, 1994.
49. Kays, S. E. and Schnellmann, R. G. Regeneration of renal proximal tubule cells in primary culture following toxicant injury: response to growth factors. Toxicol Appl. Pharmacol. 132: 273-280, 1995.
50. Lin, F., Cordes, K., Li, L., et al. Hematopoietic stem cells contribute to the regeneration of renal tubules after renal ischemia-reperfusion injury in mice. J Am Soc Nephrol, 14: 1188-1199, 2003.
51. Coles, B. L., Angenieux, B., Inoue, T., et al. Facile isolation and the characterization of human retinal stem cells. Proc Natl Acad Sci USA, 101: 15772-15777, 2004.
52. Chan, R. W., Schwab, K. E., and Gargett, C. E. Clonogenicity of human endometrial epithelial and stromal cells. Biol Reprod, 70: 1738-1750, 2004.
53. Palko, L., Bass, H. W., Beyrouthy, M. J., and Hurt, M. M. The Yin Yang-1 (YY1) protein undergoes a DNA-replication-associated switch in localization from the cytoplasm to the nucleus at the onset of S phase. J Cell Sci, 117: 465-476, 2004.
54. Singh, S. K., Clarke, I. D., Hide, T., and Dirks, P. B. Cancer stem cells in nervous system tumors. Oncogene, 23: 7267-7273, 2004.
55. Beachy, P. A., Karhadkar, S. S., and Berman, D. M. Tissue repair and stem cell renewal in carcinogenesis. Nature, 432: 324-331, 2004.
56. Sell, S. Cellular origin of cancer: dedifferentiation or stem cell maturation arrest? Environ Health Perspect, 101 Suppl 5: 15-26, 1993.
57. Russo, P. Localized renal cell carcinoma. Curr Treat Options Oncol, 2: 447-455, 2001.
58. Goldberg, J. S., Vargas, M., Rosmarin, A. S., et al. Phase I trial of interferon alpha2b and liposome-encapsulated all-trans retinoic acid in the treatment of patients with advanced renal cell carcinoma. Cancer, 95: 1220-1227, 2002.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method for detecting carcinoma in a tissue sample comprising contacting the tissue sample with an anti-REX-1 antibody that can bind a REX-1 protein of SEQ ID NO: 1 and detecting whether a significantly lower amount of the antibody binds to an REX-1 protein within cells in the test tissue sample relative to a control, non-cancerous tissue sample to thereby detect carcinoma in a tissue sample.

2. The method of claim 1, wherein the test sample comprises breast, head, neck, larynx, mouth, renal or skin cells.

3. The method of claim 1, wherein the carcinoma is metastatic and the test tissue sample is obtained from a site in a subject that is distinct from a primary site of the carcinoma.

4. The method of claim 1, wherein the anti-REX-1 antibody binds a REX-1 peptide consisting of amino acid sequence SNNLKAHILTHANTNK NEQEGK (SEQ ID NO:9).

* * * * *